(12) United States Patent
Katoh et al.

(10) Patent No.: US 12,213,729 B2
(45) Date of Patent: Feb. 4, 2025

(54) CATHETER AND RECANALIZATION CATHETER SYSTEM

(71) Applicant: ASAHI INTECC CO., LTD., Seto (JP)

(72) Inventors: Osamu Katoh, Seto (JP); Wayne Ogata, Seto (JP); Yukiko Hase, Seto (JP); Kensuke Sakata, Seto (JP); Takayuki Hori, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 1056 days.

(21) Appl. No.: 17/026,901

(22) Filed: Sep. 21, 2020

(65) Prior Publication Data

US 2021/0052321 A1 Feb. 25, 2021

Related U.S. Application Data

(63) Continuation of application No. PCT/US2019/024752, filed on Mar. 29, 2019.

(60) Provisional application No. 62/650,149, filed on Mar. 29, 2018.

(51) Int. Cl.
*A61B 18/14* (2006.01)
*A61M 25/00* (2006.01)
*A61M 25/09* (2006.01)
*A61B 18/00* (2006.01)

(52) U.S. Cl.
CPC ..... *A61B 18/1492* (2013.01); *A61M 25/0071* (2013.01); *A61M 25/09* (2013.01); *A61B 2018/00077* (2013.01); *A61B 2018/00214* (2013.01); *A61B 2018/00577* (2013.01); *A61B 2018/00982* (2013.01);

(Continued)

(58) Field of Classification Search
CPC .............. A61B 18/1492; A61B 18/042; A61B 2018/00214; A61B 2018/00577; A61B 2018/00982; A61B 2018/1467; A61B 2018/00285; A61B 2018/00583; A61B 2018/0022; A61B 2018/00267; A61B 2018/122; A61B 2018/144; A61B 2018/1472; A61B 2018/1475; A61B 2017/22095; A61M 25/0071; A61M 2025/0197; A61M 2025/09008
USPC ...... 606/41, 42, 46, 48–50; 607/98, 99, 102, 607/104, 105, 113, 115, 116
See application file for complete search history.

(56) References Cited

U.S. PATENT DOCUMENTS 5,833,688 A * 11/1998 Sieben ............... A61B 18/1492
606/41
6,958,062 B1 * 10/2005 Gough ................. A61B 18/148
606/41

(Continued)

FOREIGN PATENT DOCUMENTS

| JP | 2001518328 A | 10/2001 |
|---|---|---|
| JP | 2002538881 A | 11/2002 |

(Continued)

*Primary Examiner* — Thomas A Giuliani
(74) *Attorney, Agent, or Firm* — Oliff PLC

(57) ABSTRACT

A catheter comprises a shaft, an extended shaft portion, and an electrode disposed on an outer circumferential surface of the shaft. The shaft has a first lumen and a second lumen that is arranged adjacent to the first lumen. The extended shaft portion is provided on a distal end portion of the shaft, has the first lumen, and has a distal end portion located on a distal end side of a distal end portion of the second lumen, in the shaft.

20 Claims, 28 Drawing Sheets

(52) U.S. Cl.
CPC ............... *A61B 2018/1467* (2013.01); *A61M 2025/09008* (2013.01); *A61M 2205/3327* (2013.01)

(56) References Cited

U.S. PATENT DOCUMENTS

| | | | |
|---|---|---|---|
| 7,258,690 B2 * | 8/2007 | Sutton | A61B 18/18 606/41 |
| 2002/0133150 A1 * | 9/2002 | Whayne | A61B 18/1492 606/41 |
| 2003/0014047 A1 * | 1/2003 | Woloszko | A61B 18/1492 606/41 |
| 2003/0163178 A1 * | 8/2003 | Davison | A61B 18/148 607/101 |
| 2005/0010205 A1 * | 1/2005 | Hovda | A61B 18/1482 606/41 |
| 2006/0106375 A1 | 5/2006 | Werneth et al. | |
| 2012/0143099 A1 * | 6/2012 | Daniels | A61M 25/0029 606/14 |
| 2013/0072957 A1 | 3/2013 | Anderson | |
| 2014/0018788 A1 * | 1/2014 | Engelman | A61B 18/1492 606/33 |
| 2015/0196730 A1 | 7/2015 | O'Callaghan et al. | |
| 2015/0273181 A1 | 10/2015 | Leeflang et al. | |
| 2016/0000499 A1 * | 1/2016 | Lennox | A61N 7/022 606/41 |
| 2016/0045714 A1 | 2/2016 | Zhou et al. | |
| 2017/0086907 A1 * | 3/2017 | Satake | A61B 18/1492 |

FOREIGN PATENT DOCUMENTS

| | | |
|---|---|---|
| JP | 2007532265 A | 11/2007 |
| JP | 2012239571 A | 12/2012 |
| JP | 5564416 B2 | 7/2014 |
| JP | 6030655 B2 | 11/2016 |
| JP | 6118335 B2 | 4/2017 |
| JP | 6182660 B2 | 8/2017 |
| WO | 9916499 A1 | 4/1999 |
| WO | 0054683 A1 | 9/2000 |
| WO | 2005102440 A2 | 11/2005 |
| WO | 2008120209 A1 | 10/2008 |
| WO | 2010141417 A2 | 12/2010 |
| WO | 2011/060301 A1 | 5/2011 |
| WO | 2013043592 A1 | 3/2013 |
| WO | 2013086271 A1 | 6/2013 |
| WO | 2014150424 A1 | 9/2014 |
| WO | 2016134152 A1 | 8/2016 |

* cited by examiner

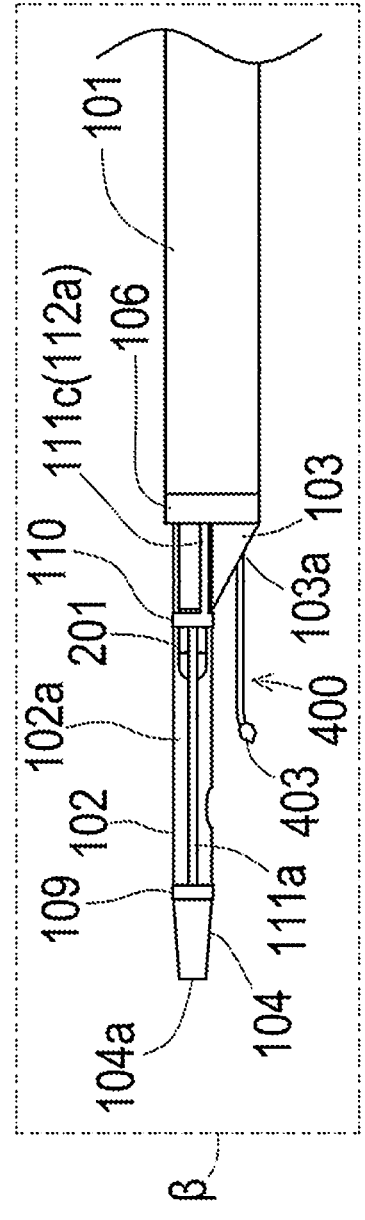
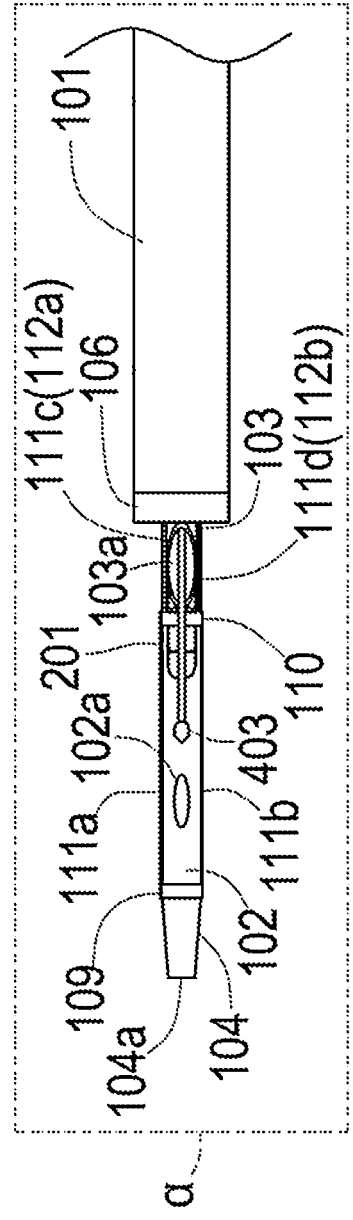
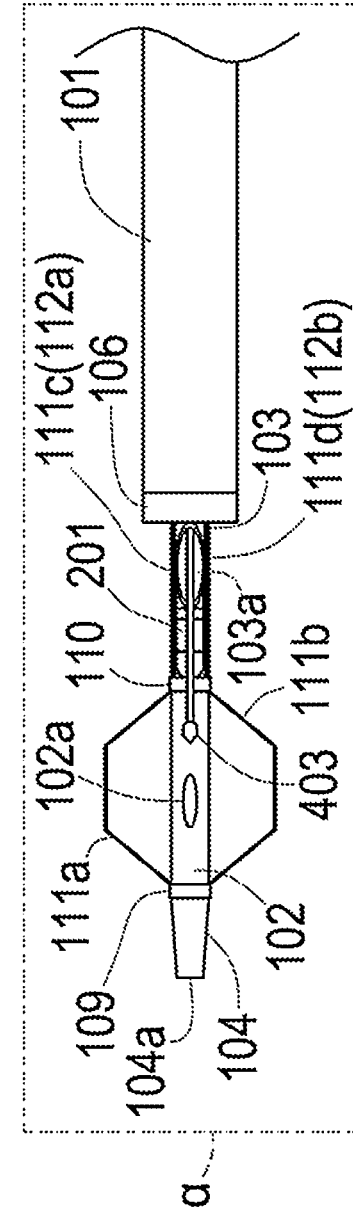
Fig. 2A
Fig. 2B
Fig. 2C

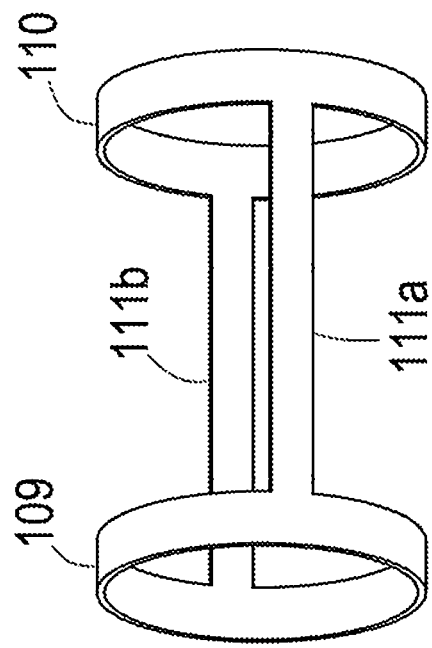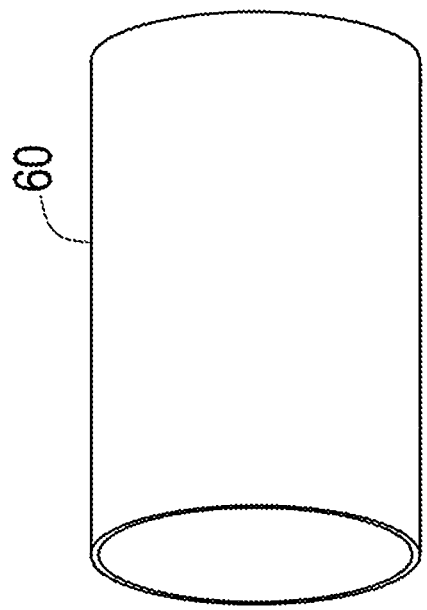
Fig. 2D
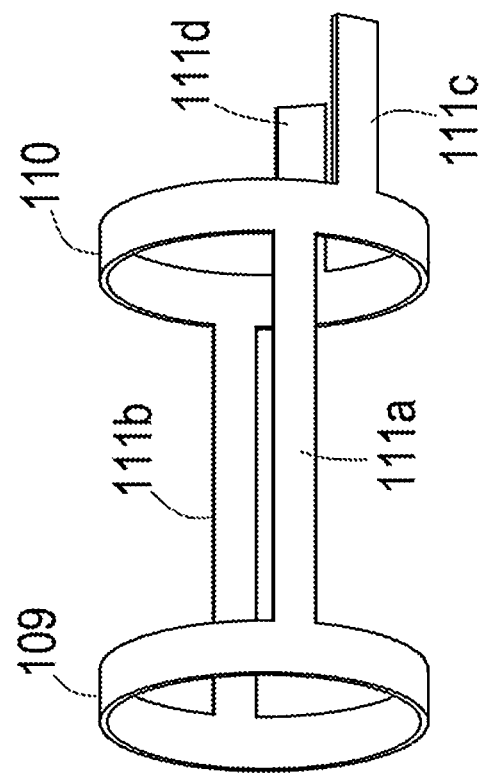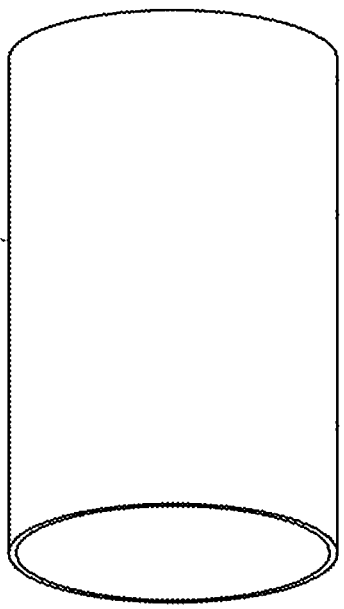
Fig. 2E

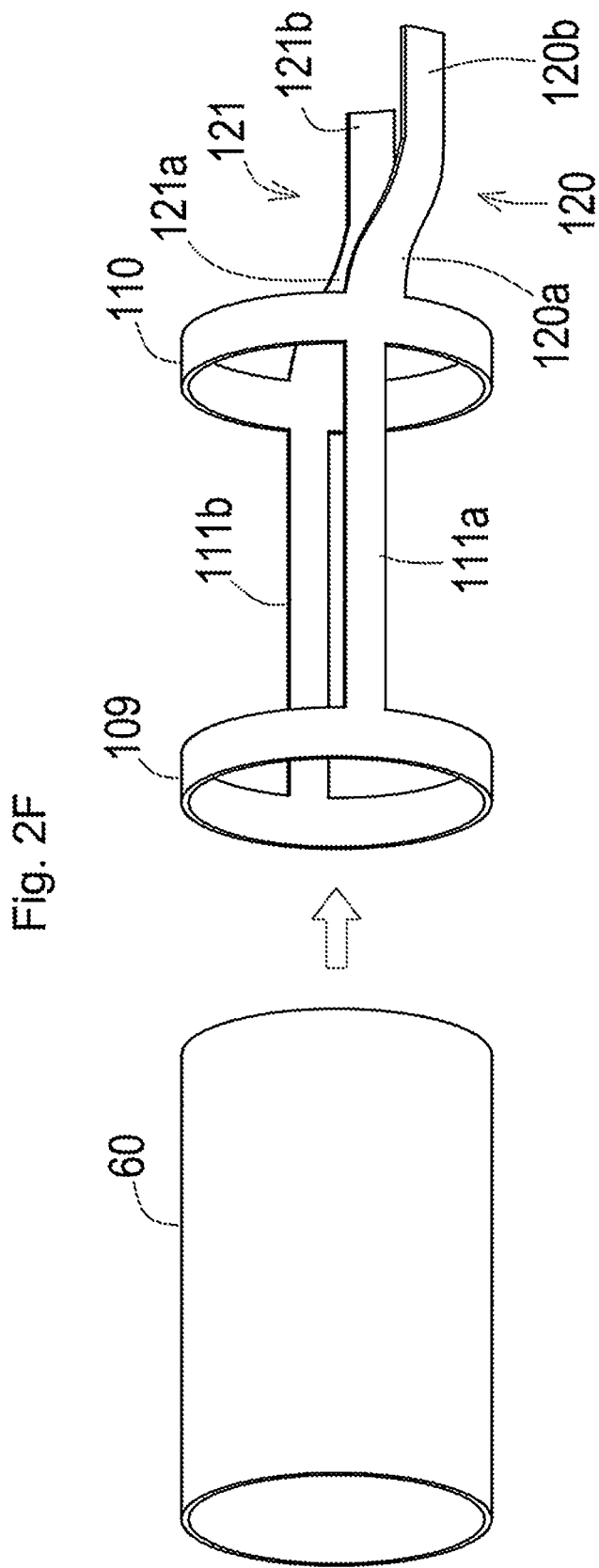

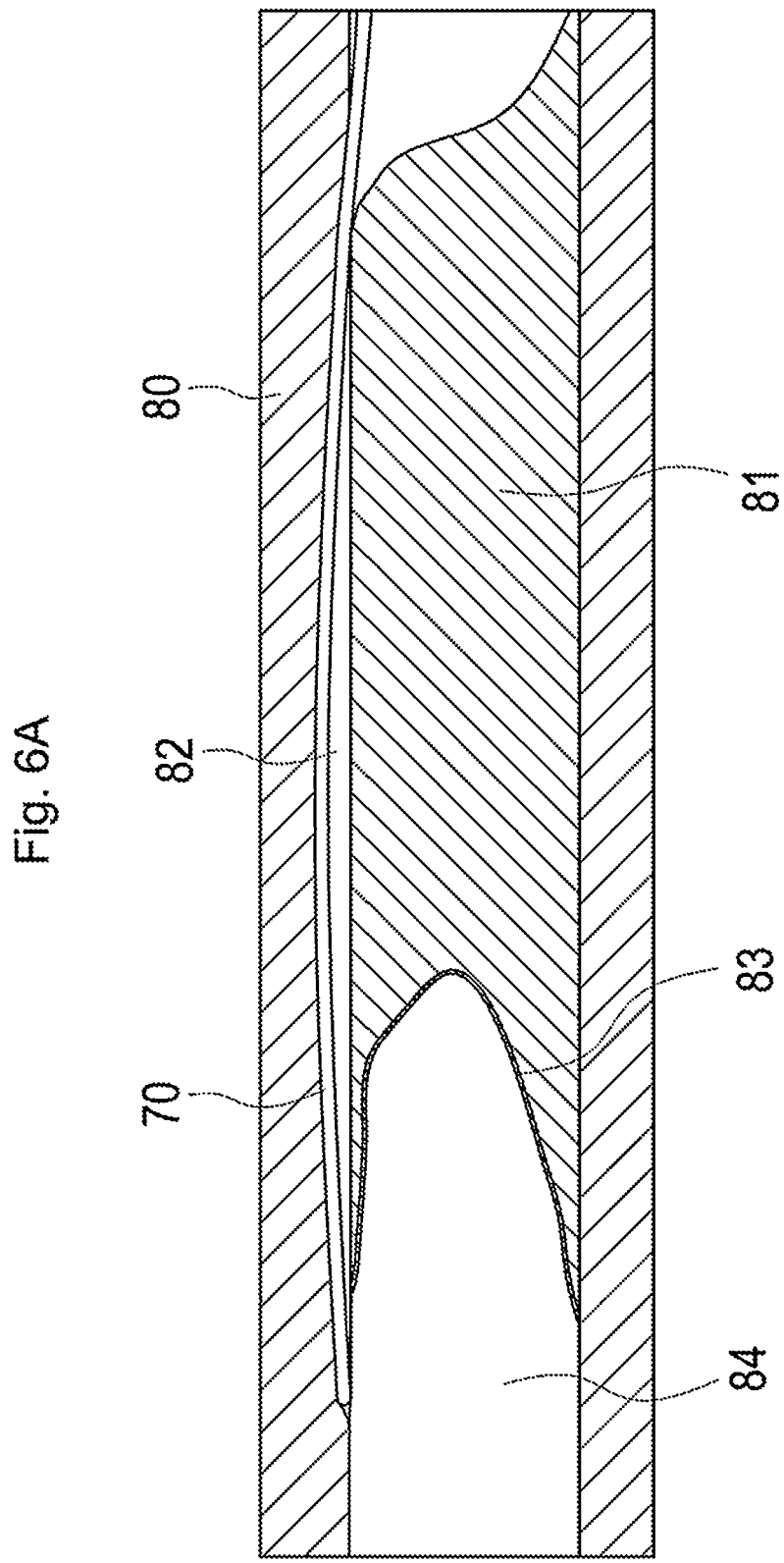

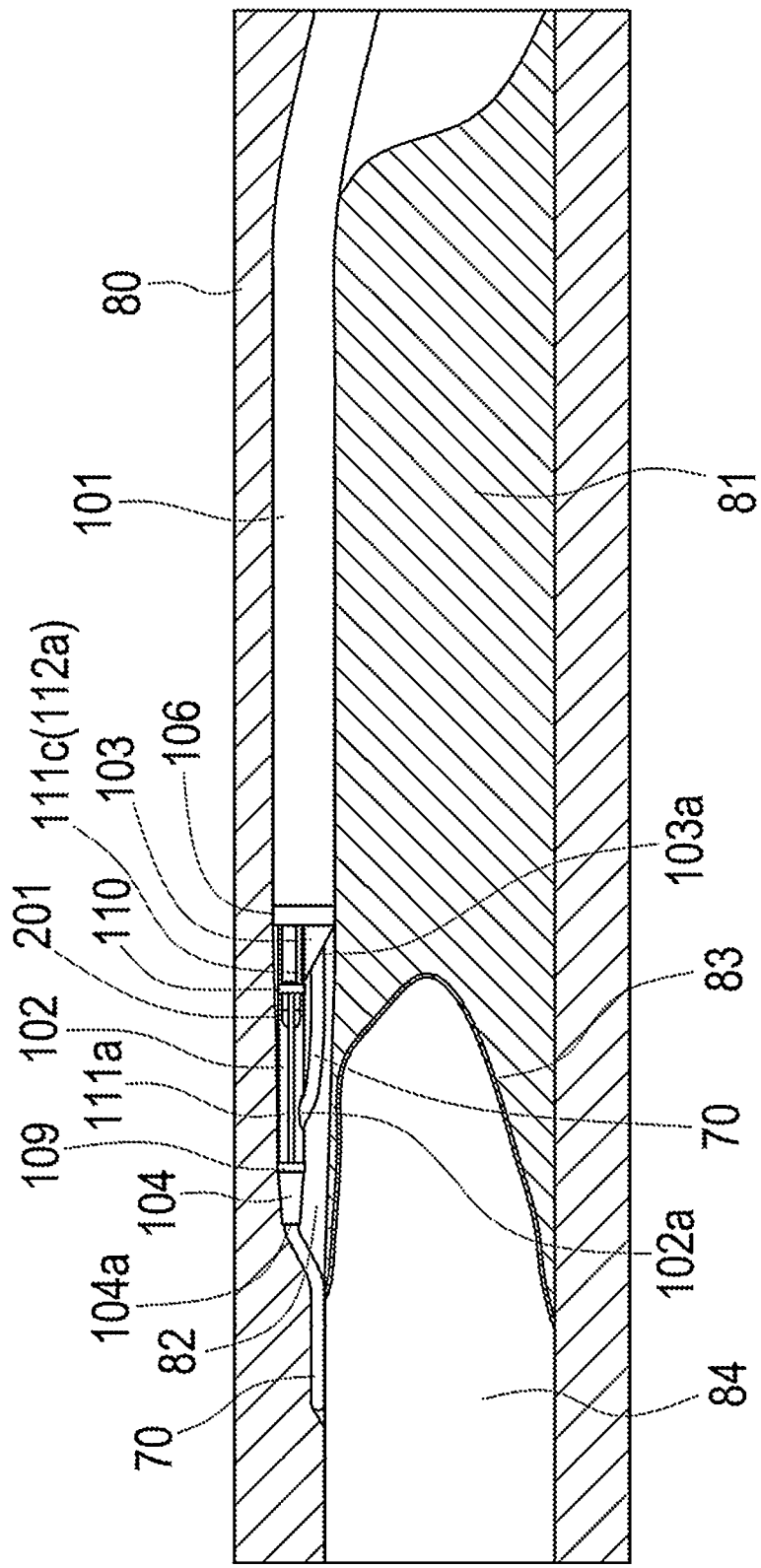

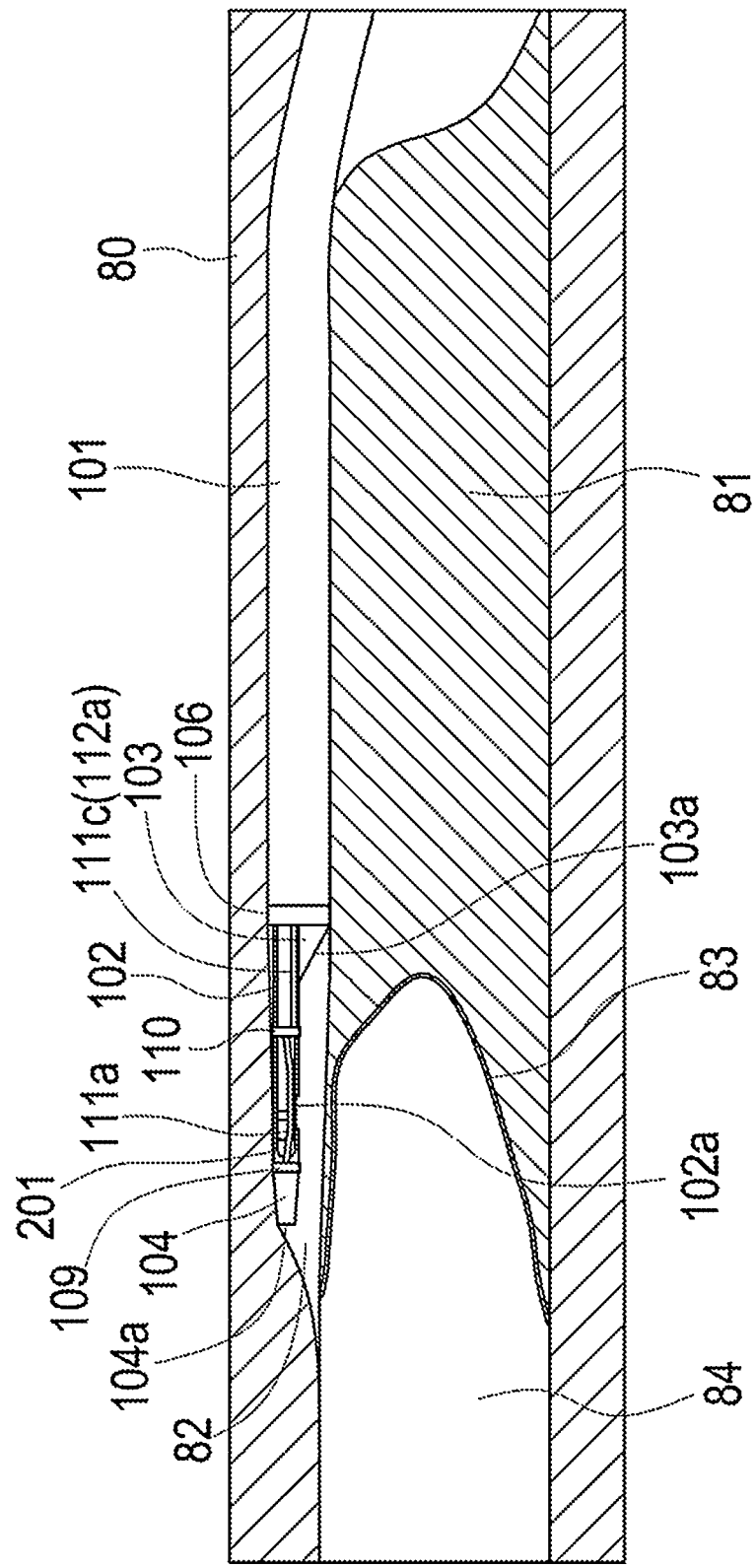

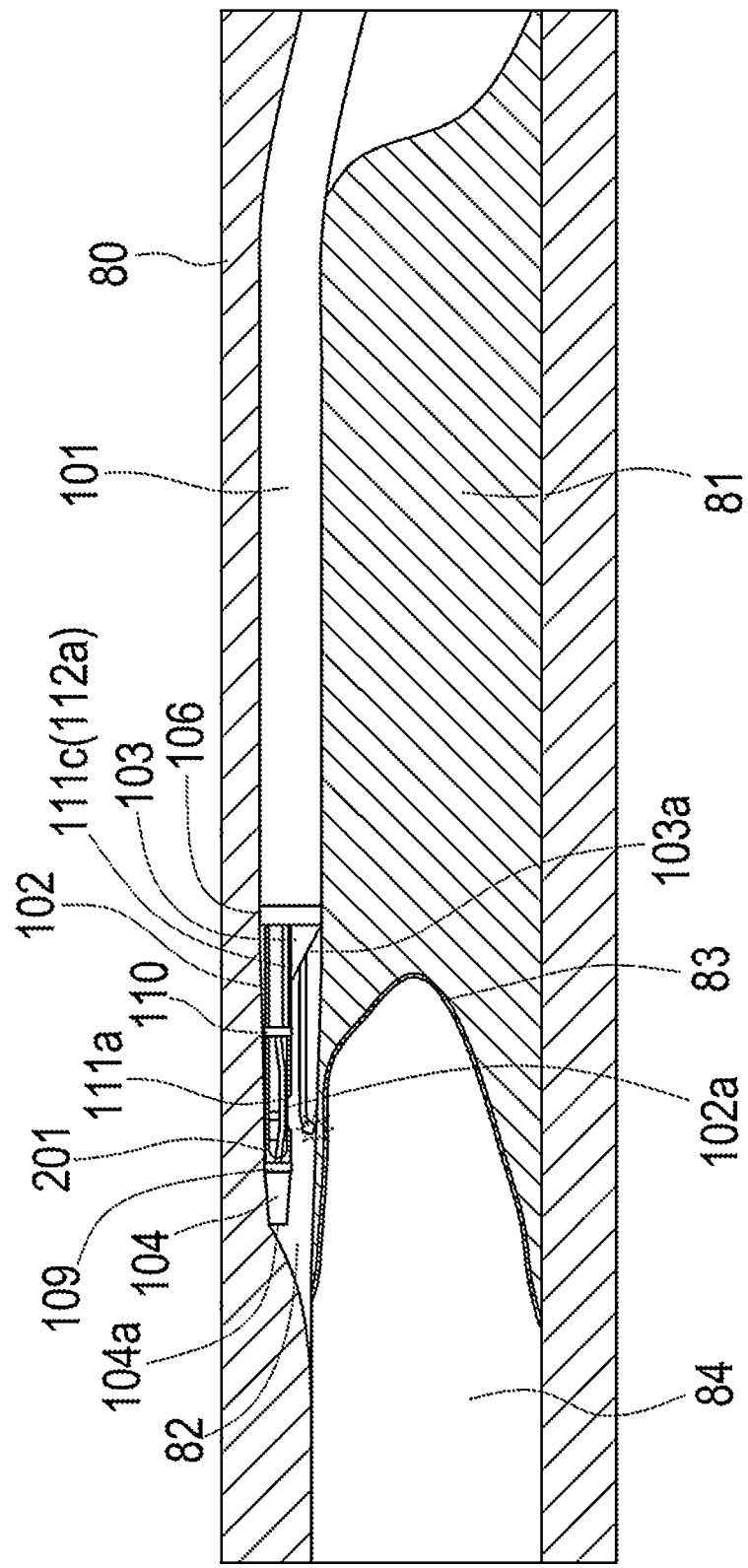

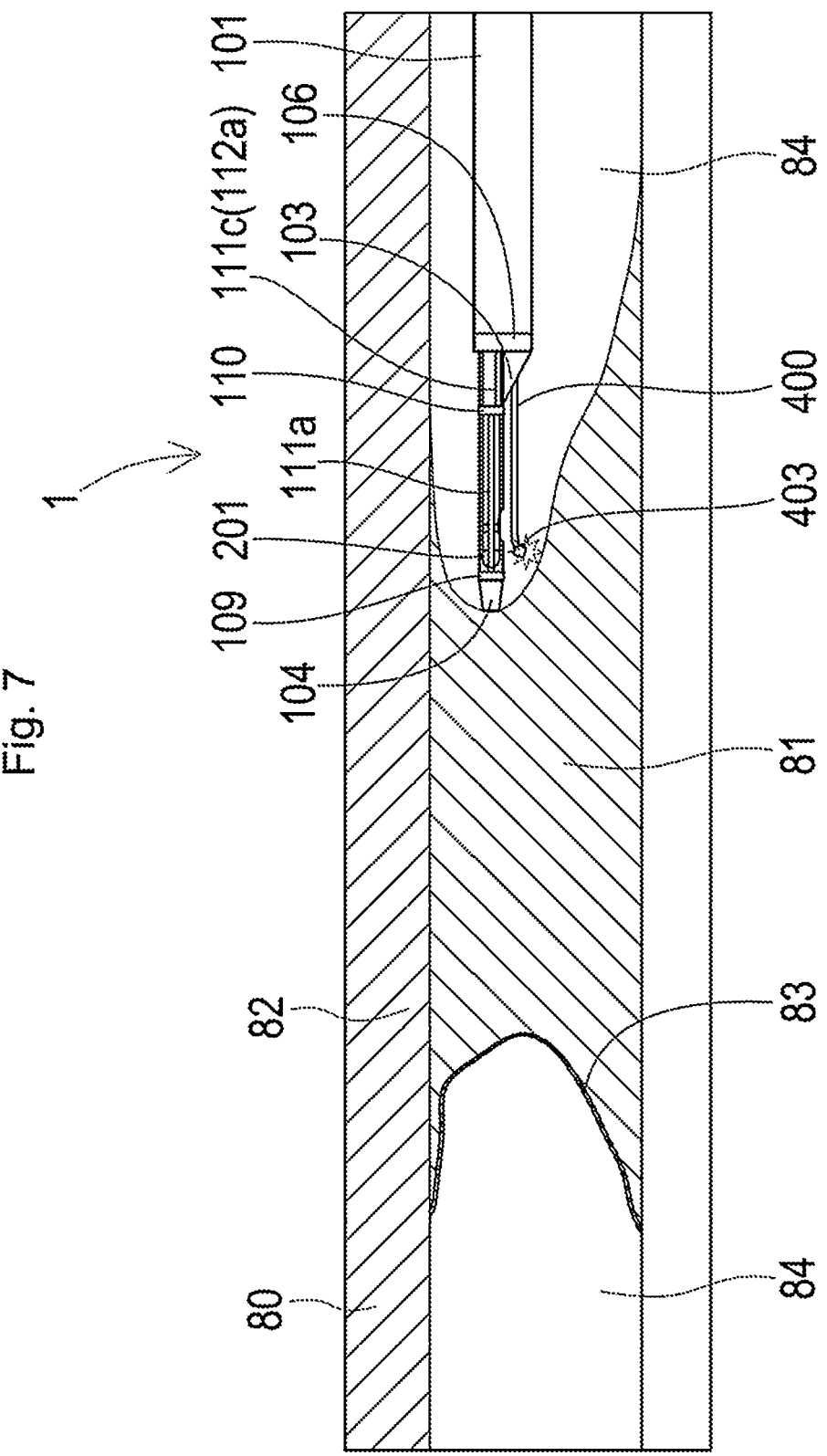

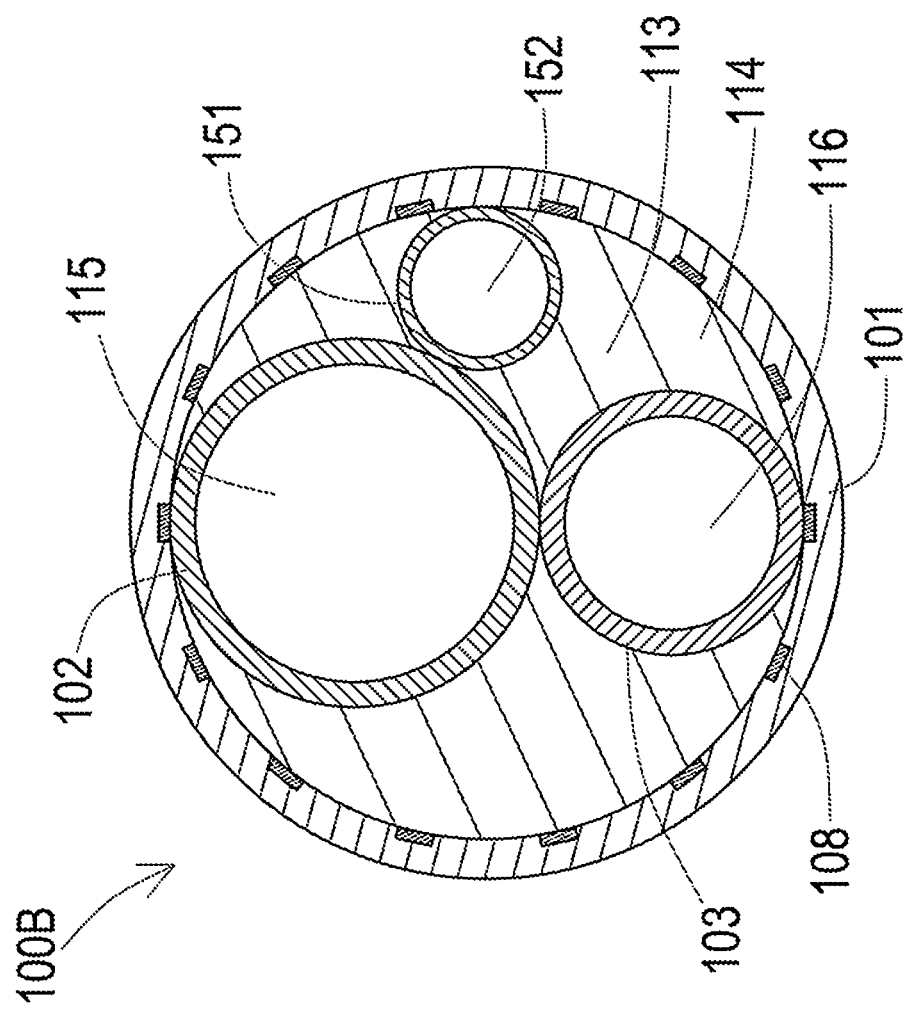

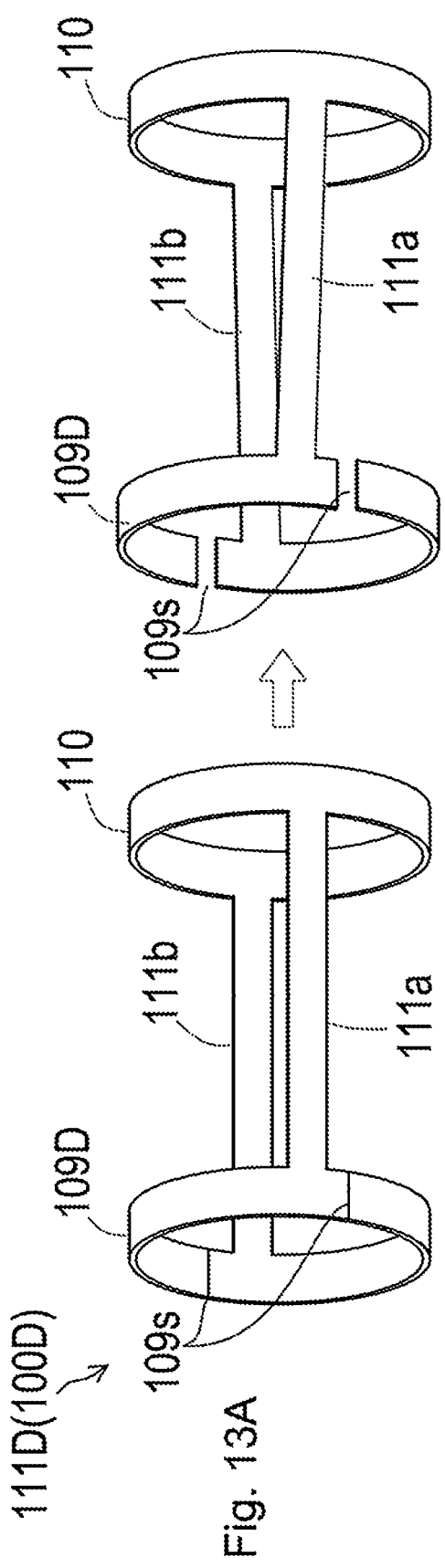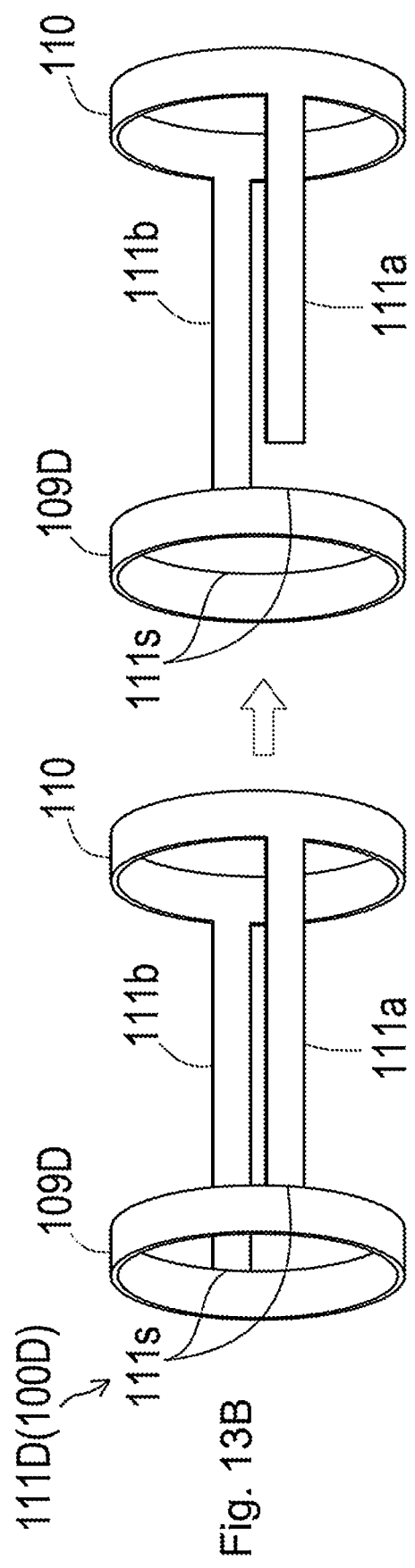

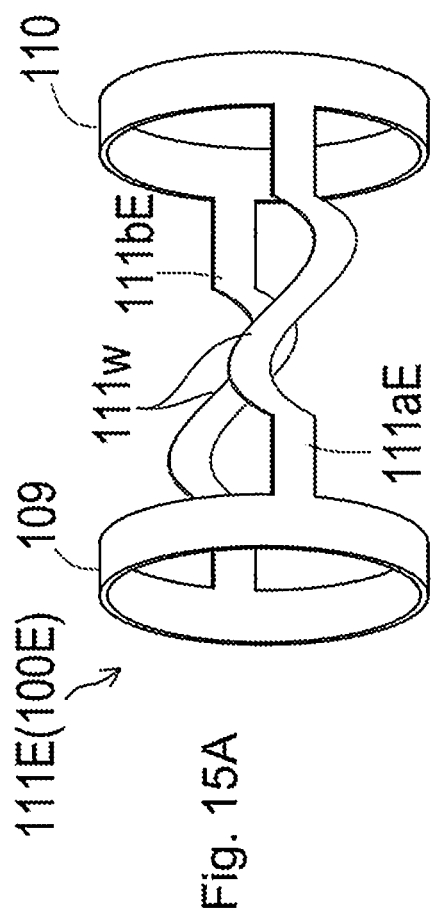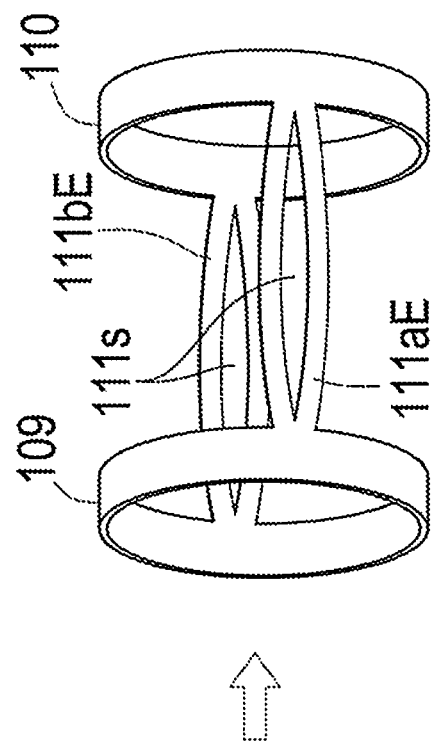

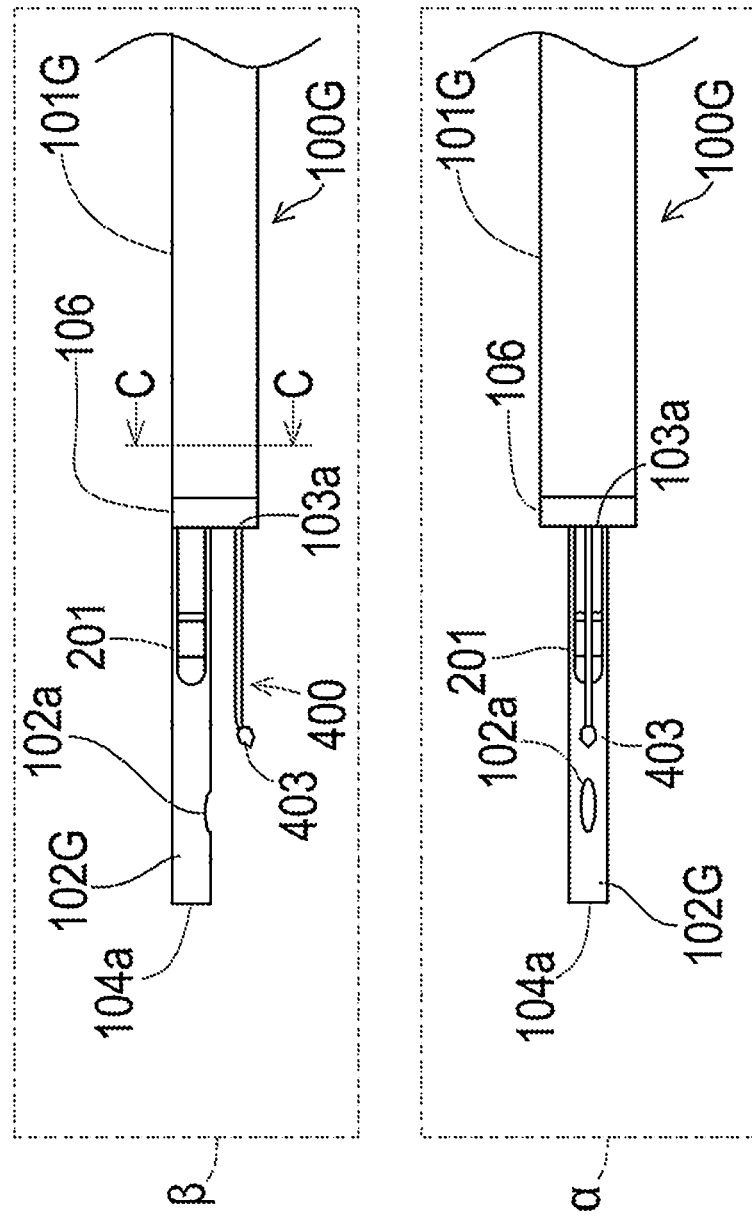

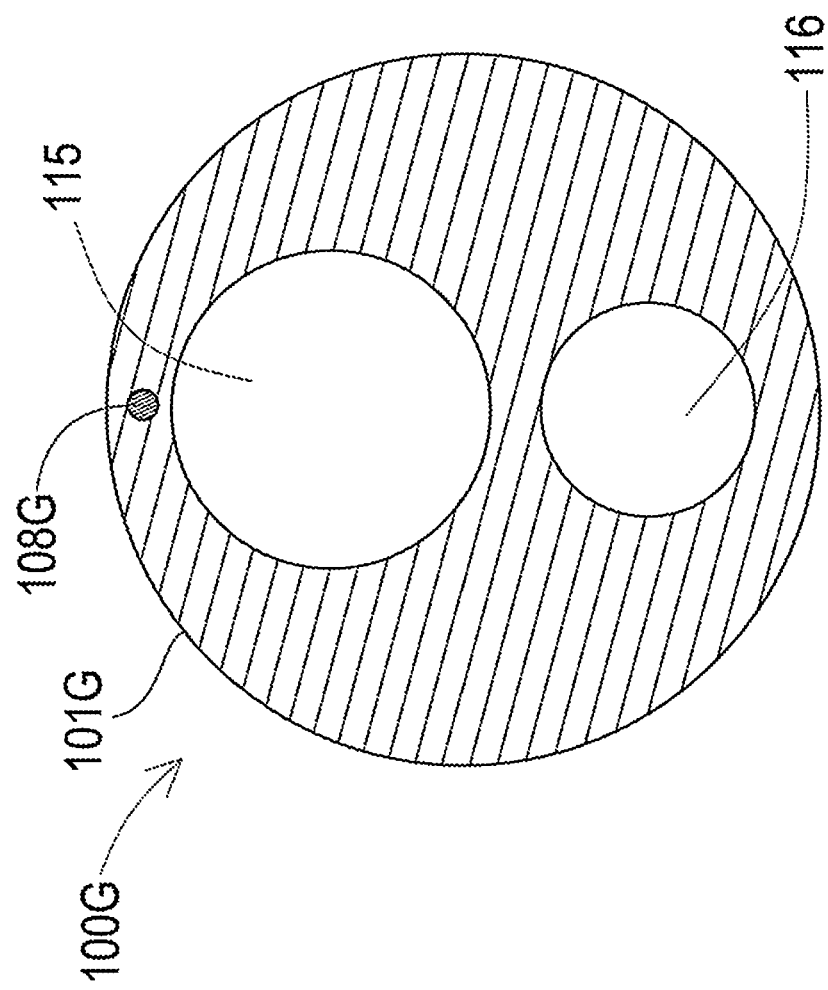

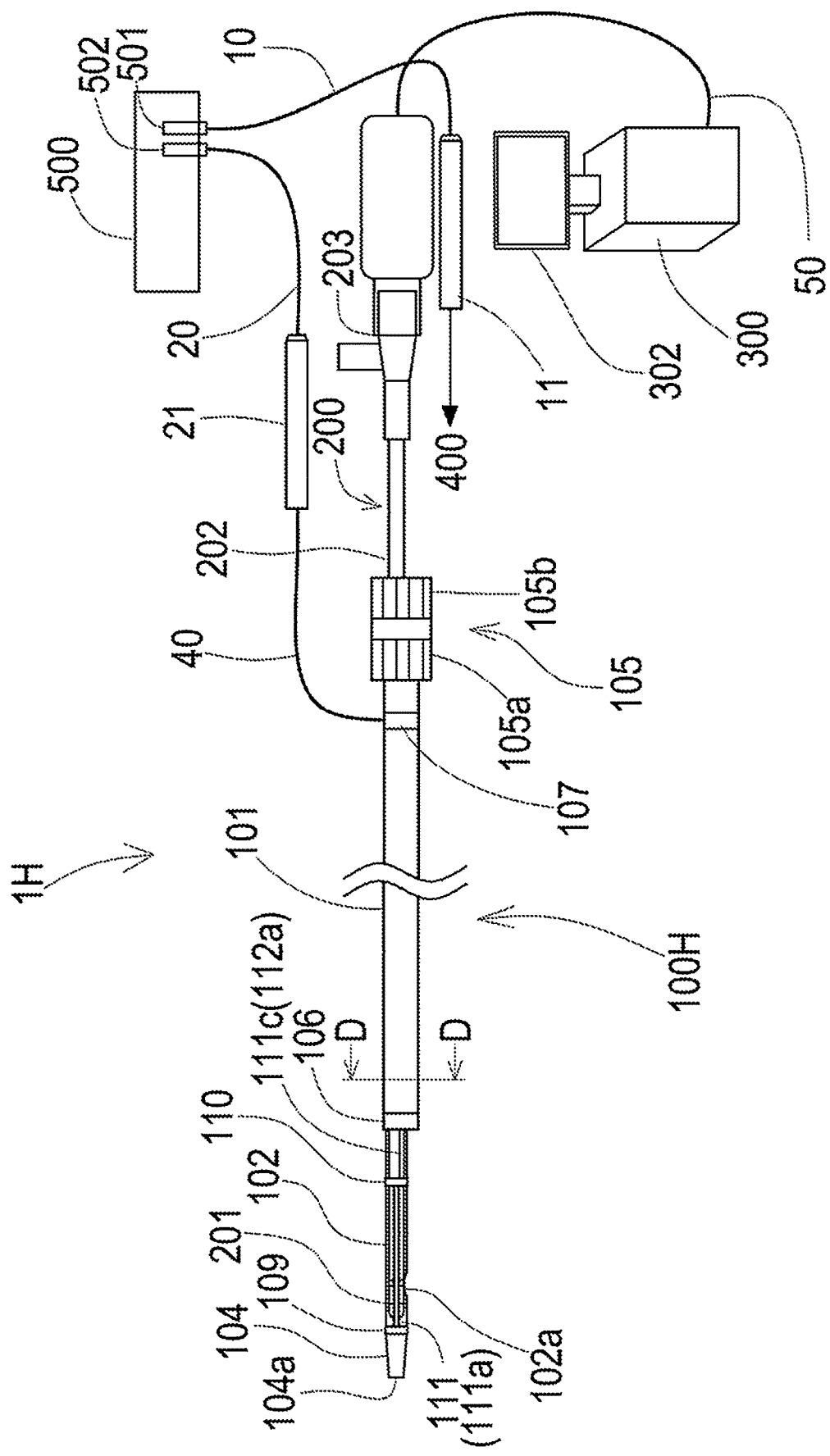

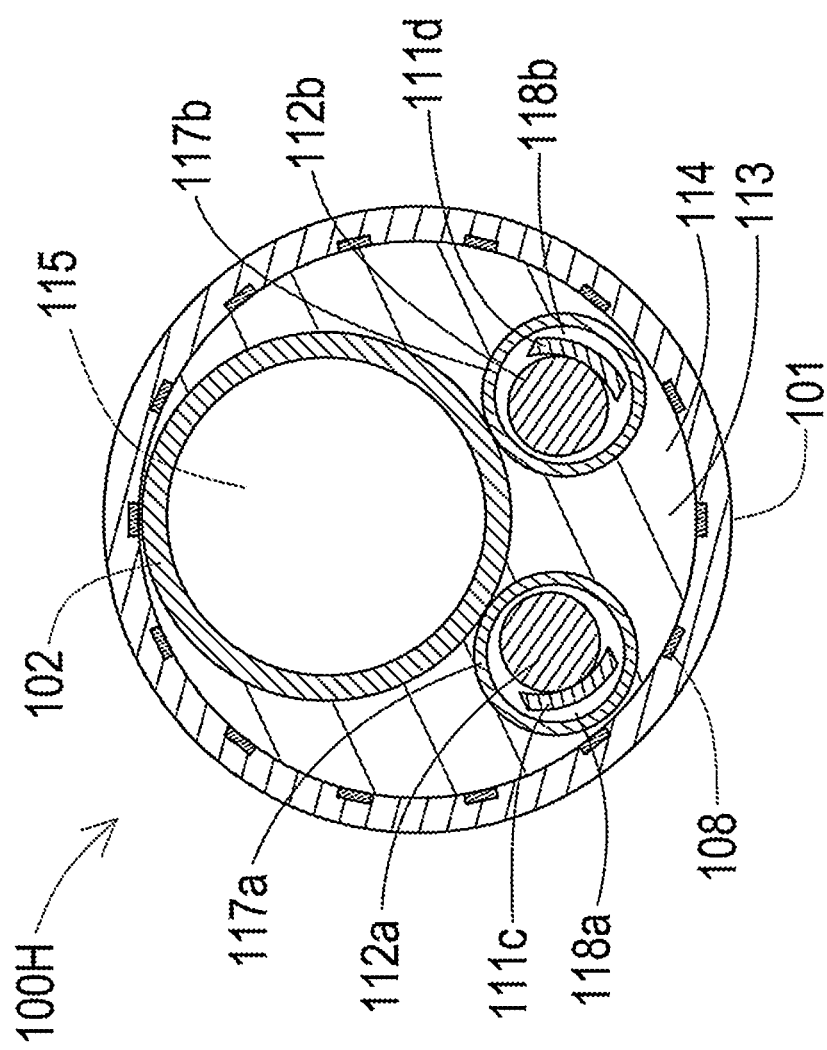

CATHETER AND RECANALIZATION CATHETER SYSTEM

CROSS REFERENCE TO RELATED APPLICATIONS

The present application is a Bypass Continuation of PCT/US2019/024752, filed Mar. 29, 2019, which is based upon and claims priority from U.S. provisional application No. 62/650,149 filed on Mar. 29, 2018, the entirety of the prior applications being hereby incorporated by reference into this application.

FIELD

The present disclosure relates to a catheter.

BACKGROUND

There may be cases of intravascular occlusion, such as chronic total occlusion (CTO). Japanese Patent No. 5564416B, No. 6030655B, No. 6118335B and No. 6182660B disclose catheters and catheter assemblies intravascularly inserted and used for canalization of CTO. JP 2002-538881A discloses a method of ablation of biological tissue by using the plasma flow.

SUMMARY

Technical Problem

A conventional antegrade approach and a retrograde approach from the peripheral side of CTO have been known as techniques for CTO canalization. The retrograde approach allows for canalization of CTO even in the case that has difficulty in antegrade canalization by a guide wire but requires the operator's knowledge and experience for the procedure. The retrograde approach is not applicable to the case that fails to detect retrograde-approachable collateral circulation.

According to the degree of calcification and fibrosis of CTO, the presence or the absence of vasoconstriction, and the anatomical conditions including the configuration of CTO such as length, bent and fragment geometry of CTO, the antegrade approach, on the other hand, may readily form a false lumen by a guide wire or may cause vascular perforation to cause a failure of recanalization or a complication. The parallel wire technique has been known as an effective technique in the antegrade approach in these cases. The parallel wire technique enables a true lumen to be retracked even in the case of aberrance of the guide wire into an inner membrane to form a false lumen and accordingly allows for canalization of CTO with the higher probability. The false lumen herein denotes any isolated cavity formed by the guide wire, other than the true lumen.

Manipulation of the guide wire under IVUS (intravascular ultrasound) guide has been performed especially in Japan, as an effective technique in the case that has difficulty in tracking a true lumen by the parallel wire technique. IVUS is an intravascular imaging tool that obtains images of vascular lumen and inside of vascular wall with a relatively high resolution in real time. Using IVUS, which has conventionally been used mainly for diagnosis, for treatment as a guide for manipulation of the guide wire (IVUS guide) allows for successful treatment in the case that is likely to fail without application of the IVUS guide.

No exclusive devices have, however, been developed for this IVUS guide-based procedure. Under existing circumstances, IVUS is separately provided intravascularly from a device for treatment, such as a (penetration) guide wire. Position information of each device and each blood vessel identified in an image obtained by IVUS indicate only a relative positional relationship to an IVUS catheter. The operator is thus required to three-dimensionally adapt the position information of each vascular site or vascular bifurcation identified in an X-ray image to the relative positional relationship of the IVUS catheter and the guide wire identified in an IVUS image in the brain of the operator. Even in an attempt for introduction of the guide wire to an optimal position by IVUS guide and for penetration of the guide wire for the purpose of CTO canalization, the IVUS catheter does not contribute to improvement of the operability of the guide wire in the false lumen. The guide wire is likely to expand a false lumen, due to the limited penetration performance of the guide wire. The conventional IVUS guide is a technique that requires a highly sophisticated device manipulation technique and three-dimensional reconstruction of vascular information and has a problem of high dependency on the operator's skill.

Such problems are not limited in canalization of CTO but are common to manipulation of medical devices such as a guide wire under guiding using a sensor such as IVUS guide. These problems are also not limited in the vascular system but are common to devices inserted in biological lumens, for example, in the lymphatic system, in the biliary system, in the urinary system, in the respiratory system, in the digestive system, in the secretory system, or in the reproductive system.

In order to solve at least part of the problems described above, an object of the present disclosure is to provide a catheter configured to hold a sensor and a medical device simultaneously.

Solution to Problem

In order to solve at least part of the problem described above, the present disclosure may be implemented by aspects described below.

(1) According to one aspect of the present disclosure, there is provided a catheter. This catheter comprises a shaft that has a first lumen and a second lumen arranged adjacent to the first lumen; an extended shaft portion that is provided in a distal end portion of the shaft, that has the first lumen, and that has a distal end portion extended toward a distal end side of a distal end portion of the second lumen in the shaft; and an electrode that is placed in an outer circumferential surface of the shaft.

This configuration enables the catheter to hold a sensor and a medical device such as a guide wire simultaneously by the shaft having the first lumen and the second lumen arranged adjacent to the first lumen.

The catheter of this aspect is provided with the extended shaft portion having the distal end portion extended toward the distal end side of the distal end portion of the second lumen in the shaft. For example, when an IVUS as a sensor is inserted into the first lumen and a transducer of the IVUS (portion configured to transmit and receive ultrasonic waves to and from biological tissue) is placed in the first lumen included in the extended shaft portion, a distal end portion of a medical device (for example, a delivery guide wire or a plasma guide wire) inserted in the second lumen can be observed by IVUS. This configuration enables the operator to recognize in real time the state of inside of a biological lumen (for example, CTO) and the position of a distal end portion of the medical device (for example, a delivery guide wire or a plasma guide wire) by only using an IVUS-based two-dimensional image. Accordingly, the catheter of this aspect allows for a procedure under guiding of the sensor (for example, under IVUS guide) without requiring the skill of separate intravascular manipulation of a plurality of devices and the skill of three-dimensional reconstruction of a sensor image and an X-ray image, which are conventionally required in the procedure under guiding of the sensor. Furthermore, the catheter of this aspect allows for a procedure only by referring to the image of the sensor and thereby reduces the frequency of obtaining X-ray images. This is expected to reduce the radiation exposure of the operator and the patient in X-ray photography and to reduce the use amount of a contrast agent in X-ray photography.

The catheter of this aspect is provided with the electrode that is placed in the outer circumferential surface of the shaft. This configuration allows for ablation of biological tissue using the plasma flow by insertion of a plasma guide wire into the second lumen. This configuration allows for more reliable penetration of the biological tissue, compared with penetration of the biological tissue using an ordinary guide wire and is thus expected to improve the success rate of CTO canalization. In other words, even in the case that conventionally requires a shift to a retrograde approach for canalization, the combined use of the catheter of this aspect with the plasma guide wire enables stable treatment by only an antegrade approach. Additionally, this antegrade approach is expected to shorten the manipulation time, compared with the retrograde approach.

As a result, the catheter of this aspect improves the convenience of the procedure under guiding of the sensor and is expected to reduce the radiation exposure, to reduce the use amount of the contrast agent, to improve the success rate of the procedure by the antegrade approach and to shortens the manipulation time.

(2) In the catheter of the above aspect, the extended shaft portion may comprise a first opening formed in the distal end portion of the extended shaft portion to communicate with the first lumen; and a second opening formed on a proximal end side of the first opening in the extended shaft portion and in a side face of the extended shaft portion on a side opposed to the second lumen to communicate with the first lumen. The shaft may comprise a third opening formed in the distal end portion of the shaft to communicate with the second lumen.

In the catheter of this aspect, the first opening that communicates with the first lumen in the distal end portion and the second opening that communicates with the first lumen in the side face on the proximal end side of the first opening and on the side opposed to the second lumen are respectively formed in the extended shaft portion. The third opening that communicates with the second lumen in the distal end portion is formed in the shaft. A delivery guide wire may be inserted from the first opening into the first lumen, led out from the second opening and then inserted from the third opening into the second lumen, so as to be fixed in the distal end portion of the shaft. Fixation of the delivery guide wire causes the delivery guide wire to be continuously located in a fixed direction on the image of the sensor. The operator moves the catheter in the longitudinal direction and rotates the catheter relative to the delivery guide wire as the basis, while referring to the image of the sensor. This controls the position of a target site for ablation by the plasma guide wire, relative to the catheter to an optimum position (optimum angle). In the catheter of this aspect, the distal end portion of the first lumen for the sensor is used for fixation of the delivery guide wire. In other words, the first lumen is shared by the delivery guide wire and the sensor. This configuration allows for reduction of the diameter of the catheter and enables the catheter to be readily inserted into a biological lumen (for example, inside of coronary artery or inside of CTO), compared with a configuration of providing a separate lumen for fixation of the delivery guide wire.

(3) In the catheter of the above aspect, the shaft may further comprise a fourth opening formed in a side face of the shaft on a proximal end side of the third opening to communicate with the second lumen.

In the catheter of this aspect, the fourth opening that communicates with the second lumen in the side face on the proximal end side of the third opening is additionally formed in the shaft. This configuration enables a proximal end side of a medical device (for example, a delivery guide wire) inserted in the second lumen to protrude out by using the fourth opening. The catheter of this aspect can thus be used as a rapid exchangeable-type catheter.

(4) The catheter of the above aspect may further comprise an expanding contracting portion placed in the extended shaft portion to be expandable and contractible in a radial direction; and an actuating portion configured to expand and contract the expanding contracting portion.

The catheter of this aspect is further provided with the expanding contracting portion that is expandable and contractible in the radial direction. After the catheter is moved in the longitudinal direction and rotated to be positioned, the expanding contracting portion is expanded, so that the catheter is fixed at the position. Fixing the catheter prior to ablation by a plasma guide wire improves the operability of the plasma guide wire in a biological lumen. The expanding contracting portion is placed in the extended shaft portion having the first lumen. Accordingly, when the expanding contracting portion is made of a material having a difference of an acoustic impedance from the acoustic impedance of biological tissue, for example, the process of expanding the expanding contracting portion is more clearly observable by IVUS as the sensor inserted in the first lumen. This configuration enables the expanding contracting portion to be expanded safely, while reducing a potential damage in a biological lumen caused by excessive expansion of the expanding contracting portion. Furthermore, even after fixation of the catheter, the IVUS is movable in the first lumen to move an image obtaining portion (transducer). Accordingly, this configuration enables a positional relationship between the distal end portion of the plasma guide wire and a target site for ablation to be observed by adjusting the image obtaining portion to the distal end portion of the plasma guide wire. As a result, this allows for penetration of the target site, while reducing the frequency of obtaining X-ray images.

(5) In the catheter of the above aspect, the expanding contracting portion may be made of a material having a larger acoustic impedance than an acoustic impedance of biological tissue.

In the catheter of this aspect, the expanding contracting portion is made of a material having a larger acoustic impedance than the acoustic impedance of the biological tissue. This enables the expanding contracting portion to be displayed more clearly, for example, on an image obtained by IVUS as the sensor inserted in the first lumen. Accordingly, the expanding contracting portion may serve as an orientation marker to check the orientation and the direction of the catheter in radioscopy.

(6) In the catheter of the above aspect, the expanding contracting portion may be made of a radiopaque material.

In the catheter of this aspect, the expanding contracting portion is made of a radiopaque material. The expanding contracting portion may serve as an orientation marker to check the orientation and the direction of the catheter by imaging of the expanding contracting portion on an X-ray image obtained by X-ray photography.

(7) In the catheter of the above aspect, the first lumen may have a larger diameter than a diameter of the second lumen.

In general, the sensor inserted in the first lumen has a larger diameter than the diameter of a medical device (for example, a delivery guide wire or a plasma guide wire) inserted in the second lumen. In the catheter of this aspect, the diameter of the first lumen is larger than the diameter of the second lumen. The respective diameters of the first lumen and the second lumen may be determined according to the diameters of the respective devices inserted into the respective lumens. This configuration reduces potential errors in insertion of the devices and reduces the diameter of the catheter, compared with a configuration that includes the first and the second lumens of an identical diameter.

(8) The catheter of the above aspect may further comprise a reinforcing member placed in a thick wall portion of the shaft. The reinforcing member may be made of a material having electrical conductivity and may be connected with the electrode to establish electrical continuity with the electrode.

The catheter of this aspect is provided with the reinforcing member placed in the thick wall portion of the shaft. This configuration improves the torque transmission performance of the catheter. The reinforcing member is made of a material having electrical conductivity and is connected with the electrode to establish electrical continuity with the electrode. This configuration reduces the diameter of the catheter, compared with a configuration provided with a separate member to establish electrical continuity with the electrode.

(9) In the catheter of the above aspect, the reinforcing member may be made of a radiopaque material.

In the catheter of this aspect, the reinforcing member is made of a radiopaque material. This allows for imaging of the reinforcing member on an X-ray image obtained by X-ray photography.

(10) According to one aspect of the present disclosure, there is provided a recanalization catheter system. This recanalization catheter system comprises the catheter of any of the above aspects, a plasma guide wire configured to perform ablation of biological tissue by using plasma; and a sensor configured to obtain information for generation of an image of the biological tissue.

This configuration provides the recanalization catheter system that improves the convenience of the procedure under guiding of the sensor configured to obtain information for generation of the image of the biological tissue and that is expected to reduce the radiation exposure, to reduce the use amount of a contrast agent, to improve the success rate of a procedure by an antegrade approach and to shortens the manipulation time.

(11) In the recanalization catheter system of the above aspect, the sensor may obtain the information for generation of the image of the biological tissue, in the first lumen. The plasma guide wire may be inserted into the second lumen such that a distal end portion of the plasma guide wire protrudes from a distal end of the second lumen, may generate plasma between the distal end portion of the plasma guide wire and the electrode, and may perform ablation of the biological tissue by using the generated plasma.

The recanalization catheter system of this aspect holds the second in the first lumen and holds the plasma guide wire in the second lumen, thus enabling the sensor and the guide wire to be held simultaneously.

(12) According to one aspect of the present disclosure, there is provided a catheter. This catheter comprises a shaft that has a lumen inside thereof; an extended shaft portion that is provided in a distal end portion of the shaft and that has the lumen; an electrode that is placed in an outer circumferential surface of the shaft; an expanding contracting portion that is placed in a distal end portion of the extended shaft portion to be expandable and contractible in a radial direction; and an actuating portion that is configured to expand and contract the expanding contracting portion.

The catheter of this aspect includes a single lumen. This configuration reduces the diameter of the catheter. The extended shaft portion is provided in the distal end portion of the shaft. This configuration enables inside of a false lumen to be observed with the higher accuracy, for example, by inserting an IVUS as the sensor into the lumen and placing a transducer of the IVUS in the first lumen in the extended shaft portion. The electrode is provided on the outer circumferential surface of the shaft. This configuration allows for ablation of biological tissue using the plasma flow by insertion of a plasma guide wire into the lumen. Additionally, the catheter has the expanding contracting portion that is expandable and contractible in the radial direction. After the catheter is moved in the longitudinal direction and is rotated to be positioned, the expanding contracting portion is expanded, so that the catheter is fixed at the position.

(13) In the catheter of the above aspect, the extended shaft portion may comprise a first opening formed in the distal end portion of the extended shaft portion to communicate with the lumen; and a second opening formed in a side face of the extended shaft portion on a proximal end side of the first opening to communicate with the lumen.

In the catheter of this aspect, the extended shaft portion is provided with the first opening that communicates with the lumen in the distal end portion of the extended shaft portion and with the second opening that communicates with the lumen in the side face on the proximal end side of the first opening. This configuration enables the proximal end side of the delivery guide wire to be inserted from the first opening into the lumen, to pass through the lumen and to protrude out. The catheter of this aspect can thus be used as a rapid exchangeable-type catheter. When the plasma guide wire is inserted in the lumen in use, protrusion of the distal end portion of the plasma guide wire from the first opening facilitates ablation of biological tissue located in the vicinity of the distal end portion of the catheter. Furthermore, protrusion of the distal end portion of the plasma guide wire from the second opening facilitates ablation of biological tissue located in the vicinity of the side face of the catheter.

(14) According to one aspect of the present disclosure, there is provided a catheter. This catheter comprises a shaft that has a lumen inside thereof and that is provided with an opening in a distal end portion of the shaft to communicate with the lumen; and an electrode that is placed in an outer circumferential surface of the shaft located on a proximal end side of the opening. Plasma is generated between the electrode and a distal end portion of a plasma guide wire that is inserted into the lumen so as to protrude from the opening and is used to perform ablation of biological tissue.

The catheter of this aspect has the electrode that is provided on the outer circumferential surface of the shaft.

This configuration allows for ablation of biological tissue using the plasma flow by insertion of a plasma guide wire into the lumen.

The present disclosure may be implemented by various aspects, for example, a catheter, a manufacturing method or a use method of the catheter, a catheter system including a catheter, a sensor and another device such as a delivery guide wire or a plasma guide wire, or a manufacturing method or a use method of the catheter system.

BRIEF DESCRIPTION OF DRAWINGS

FIG. 2A is a schematic side view illustrating a distal end portion of a plasma catheter;

FIG. 2B is a schematic bottom view illustrating the distal end portion of the plasma catheter;

FIG. 2C is a schematic bottom view illustrating the distal end portion of the plasma catheter;

FIG. 2D is a diagram illustrating a method of integrally forming a first ring, a second ring, a first stabilizer piece and a second stabilizer piece;

FIG. 2E is a diagram illustrating a method of integrally forming a first ring, a second ring, a first stabilizer piece, a second stabilizer piece, a first wire piece and a second wire piece;

FIG. 2F is a diagram illustrating a method of integrally forming a first ring, a second ring, a first stabilizer piece, a second stabilizer piece, a first wire piece and a second wire piece;

FIG. 6A is a diagram illustrating the state in which a false lumen is formed by a delivery guide wire;

FIG. 6B is a diagram illustrating the state in which the plasma catheter is inserted;

FIG. 6C is a diagram illustrating the state in which the plasma catheter is fixed;

FIG. 6D is a diagram illustrating the state in which the plasma catheter reaches a true lumen;

FIG. 7 is a diagram illustrating another example of use of the plasma guide wire CTO system;

FIG. 11 is a schematic diagram illustrating a section of a plasma catheter taken along a line B-B in FIG. 10;

FIG. 13A is a diagram illustrating one example of the expanding contracting portion according to a fifth embodiment;

FIG. 13B is a diagram illustrating another example of the expanding contracting portion according to the fifth embodiment;

FIG. 15A is a diagram illustrating another example of the expanding contracting portion according to the sixth embodiment;

FIG. 15B is a diagram illustrating another example of the expanding contracting portion according to the sixth embodiment;

FIG. 17A is a schematic side view illustrating one example of a distal end portion of a plasma catheter;

FIG. 17B is a schematic bottom view illustrating one example of the distal end portion of the plasma catheter;

FIG. 18 is a schematic diagram illustrating a section of the plasma catheter taken along a line C-C in FIG. 17;

FIG. 19 is a schematic diagram illustrating the general configuration of a plasma guide wire CTO system according to a ninth embodiment;

FIG. 20 is a schematic diagram illustrating a section of a plasma catheter taken along a line D-D in FIG. 19;

DETAILED DESCRIPTION OF EMBODIMENTS

A. First Embodiment

<Background>

Figure 1:
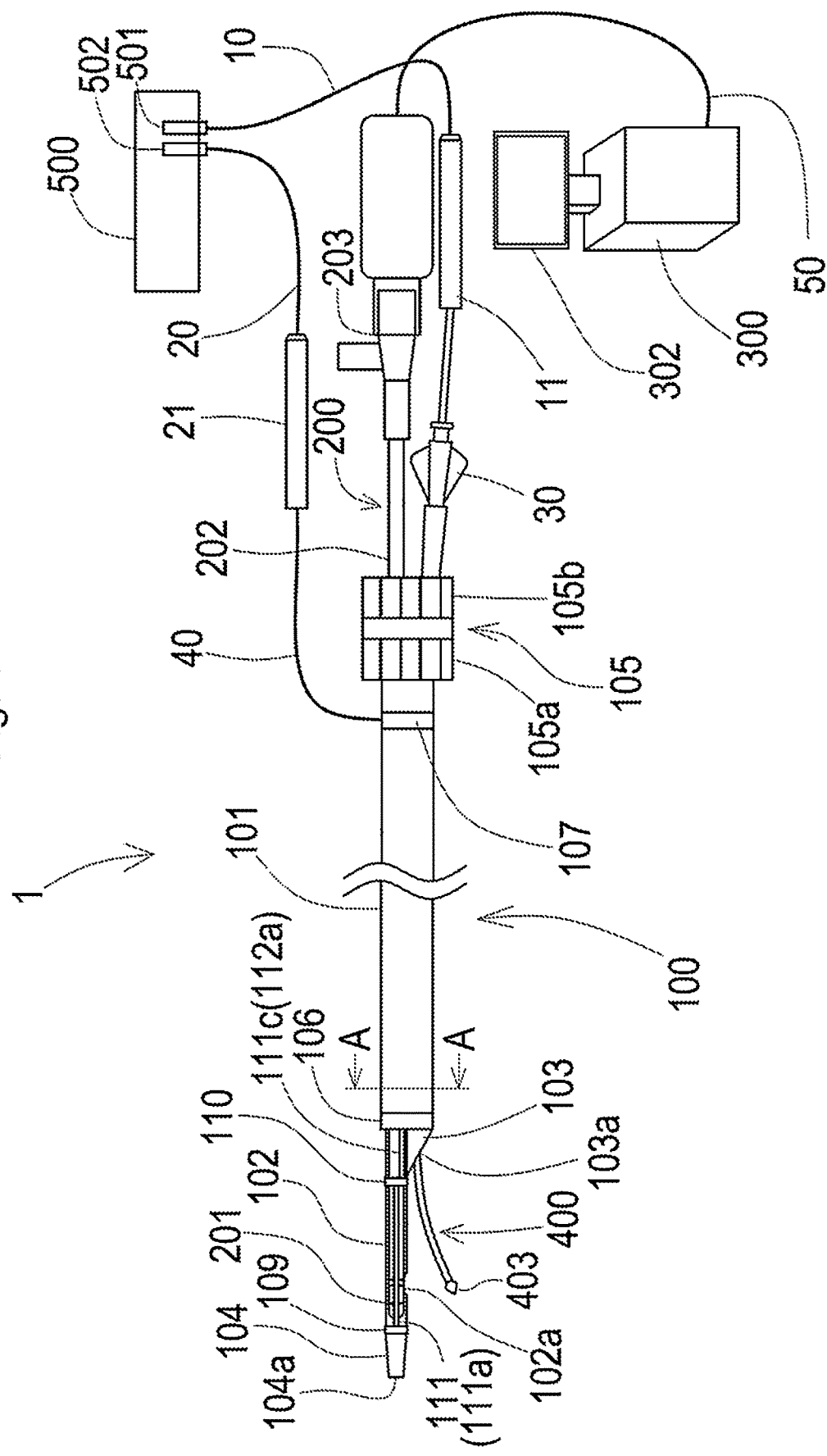
FIG. 1 is a schematic diagram illustrating the general configuration of a plasma guide wire CTO system.

Completion of CART (controlled antegrade and retrograde tracking) technique devised by Kato in 2004 established a chronic total occlusion-percutaneous coronary intervention (hereinafter referred to as CTO-PCI) procedure by a retrograde approach. The establishment of the CTO-PCI procedure based on the CART technique enables certain levels of skilled medical doctors to canalize the CTO. An antegrade approach is, however, to be selected in the case that fails to detect retrograde-approachable collateral circulation.

According to the degree of calcification of CTO and anatomical conditions including the configuration of CTO such as length, bent and fragment geometry of CTO, a false lumen may be readily formed by a guide wire to cause a failure or a complication.

The parallel wire technique is effective in the antegrade approach in these cases. The parallel wire technique enables a true lumen to be retracked even in the case of aberrance of the guide wire into an inner membrane to form a false lumen and accordingly allows for canalization of CTO with the higher probability.

In some cases, however, even the parallel wire technique may cause expansion of the false lumen or formation of hematoma. As a result, this is likely to cause exclusion and collapse of the true lumen. There is accordingly a difficulty in tracking the true lumen.

In these cases, manipulation of the guide wire under IVUS (intravascular ultrasound) guide has been performed especially in Japan. IVUS is an intravascular imaging tool that obtains images of vascular lumen and inside of vascular wall with a relatively high resolution in real time.

In PCI, IVUS has been used for diagnosis. Using IVUS for treatment as a guide for manipulation of the guide wire (IVUS guide) allows for successful treatment in the case that is likely to fail without application of the IVUS guide. No exclusive devices have, however, been developed for this IVUS guide-based procedure. Under existing circumstances, IVUS is separately provided intravascularly from a device for treatment. Position information of each device and each blood vessel identified in an image obtained by IVUS indicates a relative positional relationship to an IVUS catheter. There is accordingly a need to three-dimensionally adapt IVUS information in the brain of the operator, based on position information of each vascular site and vascular bifurcation identified in an X-ray image and the relative positional relationship of the IVUS catheter and the guide wire. Even in an attempt for introduction of the guide wire to an optimal position by IVUS guide and for penetration of the guide wire for the purpose of CTO canalization, the IVUS catheter does not improve the operability of the guide wire in the false lumen. In some cases, the guide wire is likely to slip in or under an inner membrane and expand a false lumen, due to the limited penetration performance of the guide wire conventionally used for CTO. The IVUS guide is a technique that requires a highly sophisticated device manipulation technique and three-dimensional reconstruction of vascular information and has a problem of high dependency on the operator's skill.

By taking into account the above problems, the inventors have proposed an IVUS guide-based plasma guide wire CTO system that allows for canalization of CTO by CTO ablation (excision) using plasma. In this system, a plasma guide wire equipped with a distal-end tip serving as an electrode used for ablation and an IVUS imaging sensor configured to obtain images of vascular lumen and occlusion plaque of CTO are located on an identical device (plasma catheter).

This system enables the state of CTO and the position of the plasma guide wire to be recognized in real time by only a two-dimensional image of the IVUS imaging sensor. There is accordingly no need for separate intravascular manipulation of a plurality of devices and three-dimensional reconstruction of the IVUS-based image and the X-ray image information.

Unlike a conventional device that performs penetration using an ordinary guide wire, this system performs ablation by using the plasma guide wire in combination with the imaging sensor. This allows for reliable penetration of biological tissue around the electrode and ensures canalization of CTP. This system performs heartbeat synchronization and establishes electrical continuity with RF (radio-frequency) having a high voltage and an ultrashort pulse width between a distal end of the plasma guide wire and an electrode placed on a shaft distal side of the plasma catheter for generation of plasma.

The plasma catheter has a torque performance of transmitting a torque on a proximal end side toward a distal end side and is controllable to rotate to ±90 degrees. A distal-end outlet port of the plasma catheter (distal-end outlet port of the lumen in which the plasma guide wire is inserted) is located in a fixed direction (in the same direction as that of the guide wire for delivery) on the IVUS image. This configuration enables the catheter to be controlled by moving in a longitudinal direction and rotating with referring to the IVUS image, such that a target site to be penetrated is located at a center of the IVUS image (at an optimum angle). This eliminates the need for the three-dimensional reconstruction described above. A controllable stabilizer for catheter fixation is mounted to a distal end portion of the plasma catheter. This configuration enables the plasma catheter to be stably fixed in the optimum site described above with obtaining the IVUS image. Fixation of the plasma catheter to the lumen significantly improves the operability of the plasma guide wire in the false lumen or inside of CTO. When the stabilizer is formed from a radiopaque material, the position and the rotating direction of the plasma catheter are readily recognizable in radioscopy. This allows for manipulation of the plasma guide wire in radioscopy with referring to the IVUS image. Simultaneously, moving of the imaging sensor is controllable in the fixed plasma catheter, so that an image obtaining portion is movable. This configuration enables the distal end portion of the plasma guide wire to be traced on the IVUS image with fixation of the catheter. This accordingly allows for manipulation of the guide wire and penetration of the guide wire into a true lumen by ablation only with the IVUS image information without requiring radioscopy.

This type of complex device generally has a large profile and accordingly has difficulty in application to the CTO blood vessel. The plasma catheter of this disclosure, however, employs a common lumen for the guide wire for delivery and the lumen for imaging sensor and has a distal-end profile that is equivalent to that of the conventional IVUS catheter to be readily inserted into the coronary artery and into the CTO.

Even in a case that requires a shift to the retrograde approach for canalization, this system enables stable treatment by only the antegrade approach.

Additionally, this system shortens the manipulation time and allows for manipulation based on only the IVUS guide. This reduces X-ray exposure of the operator and the patient. Such wire manipulation under the IVUS guide is expected to have a significant saving effect of a contrast agent.

Accordingly, this system reduces the contingency of CTO canalization of the conventional CTO guide wires and devices and the recent CTO technique and improves the convenience of the IVUS guide. This is expected to spread the IVUS guide-based procedure in CTO-PCI and thereby contribute to shortening the manipulation time, reducing the radiation exposure and improving the success rate.

Embodiment

FIG. 1 is a schematic diagram illustrating the general configuration of a plasma guide wire CTO system. The plasma guide wire CTO system is mainly used for treatment of CTO by an antegrade approach.

In FIG. 1, the plasma guide wire CTO system 1 is comprised of a plasma catheter 100, an imaging sensor 200, an imaging console 300, a plasma guide wire 400 and an RF generator 500. FIG. 1 illustrates a schematic side view of the plasma catheter 100.

FIG. 2A is a schematic side view illustrating a distal end portion of the plasma catheter 100.

FIG. 2B is a schematic bottom view illustrating the distal end portion of the plasma catheter and illustrates a closed state of a stabilizer 111 comprised of a first stabilizer piece 111a and a second stabilizer piece 111b described later.

FIG. 2C is a schematic bottom view illustrating the distal end portion of the plasma catheter 100 and illustrates an expanded and open state of the stabilizer 111.

FIG. 2D is a diagram illustrating a method of integrally forming a first ring 109, a second ring 110, the first stabilizer piece 111a and the second stabilizer piece 111b described later.

FIG. 2E is a diagram illustrating a method of integrally forming a first wire piece 111c and a second wire piece 111d for opening and closing the stabilizer 111, along with the first ring 109, the second ring 110, the first stabilizer piece 111a and the second stabilizer piece 111b described later.

FIG. 2F is a diagram illustrating a method of integrally forming a first wire piece 120 and a second wire piece 121 for opening and closing the stabilizer 111, along with the first ring 109, the second ring 110, the first stabilizer piece 111a and the second stabilizer piece 111b described later.

Figure 3:
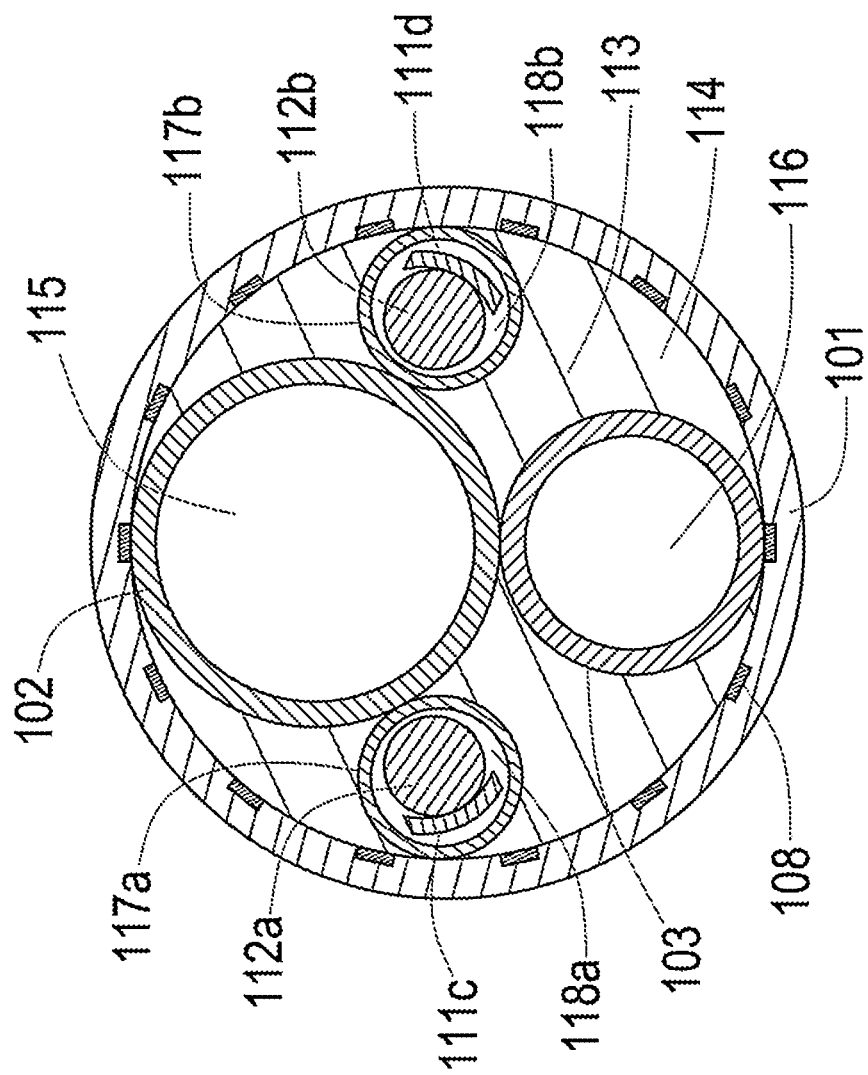
FIG. 3 is a schematic diagram illustrating a section of the plasma catheter taken along a line A-A in FIG. 1.

FIG. 3 is a schematic diagram illustrating a section of the plasma catheter 100, taken on a line A-A in FIG. 1.

Figure 4:
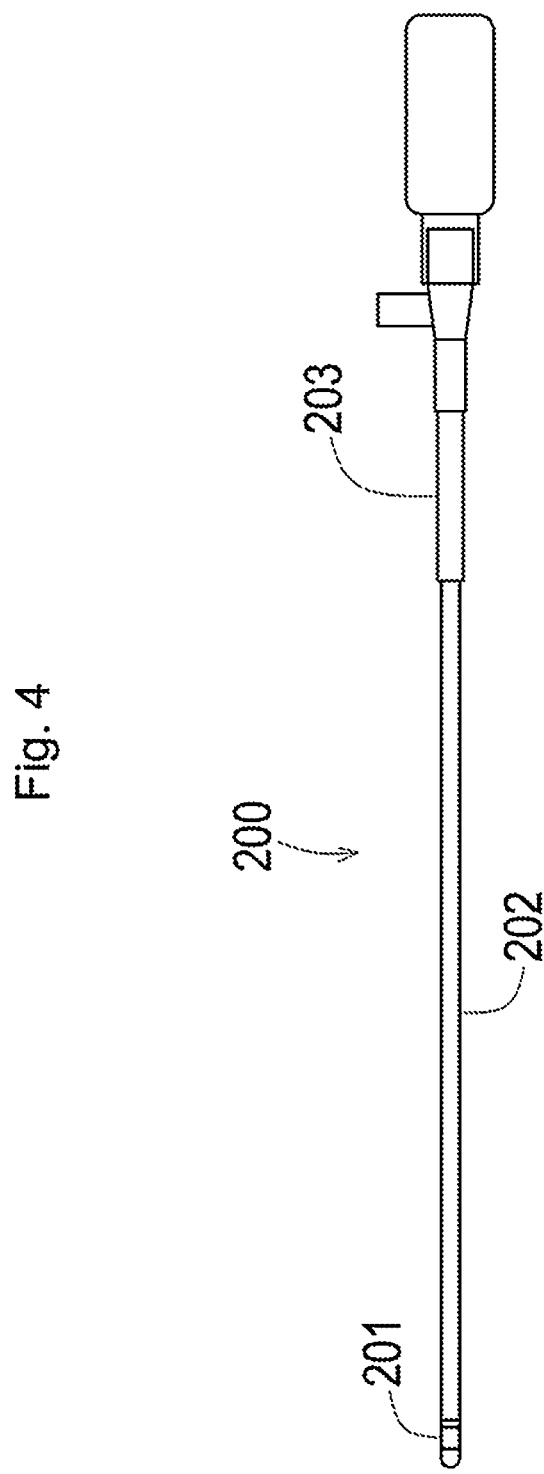
FIG. 4 is a schematic diagram illustrating an imaging sensor.

FIG. 4 is a schematic diagram illustrating the imaging sensor 200.

Figure 5:
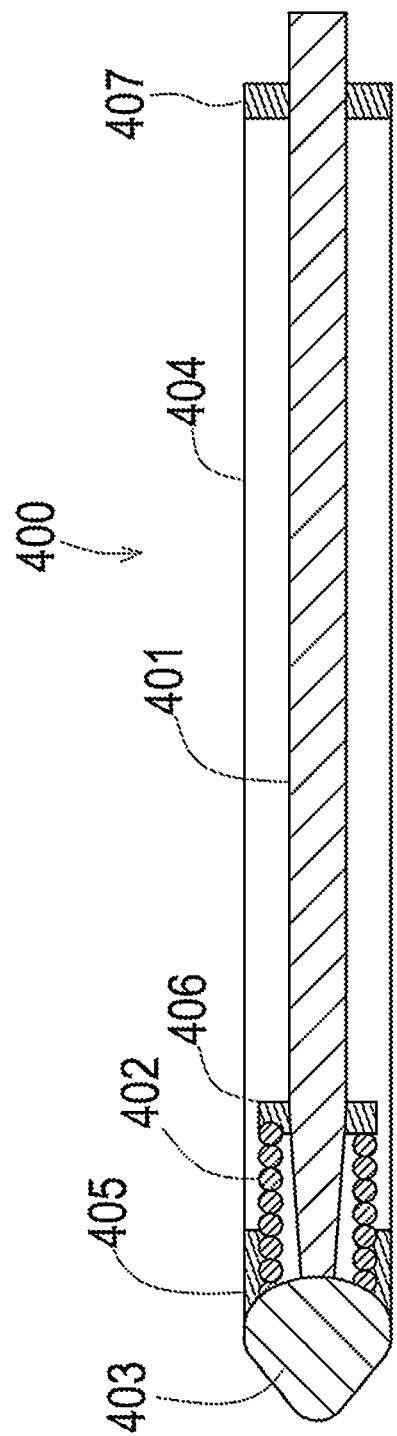
FIG. 5 is a schematic diagram illustrating a plasma guide wire.

FIG. 5 is a schematic diagram illustrating the plasma guide wire 400.

FIGS. 6A to 6D are diagrams illustrating one example of use of the plasma guide wire CTO system 1 in the case where CTO formed in coronary artery is canalized by an antegrade approach.

FIGS. 1 to 6D include illustrations of some parts of respective components at relative size ratios different from the actual conditions for convenience of explanation. FIGS. 1 to 6D also include exaggerated illustrations of some parts of the respective components.

In FIG. 1 to FIG. 6D (except FIG. 3), a left side is called a "distal end side" of each component, and a right side is called a "proximal end side" of each component. With regard to each component, an end located on the distal end side is called "distal end", and an end located on the proximal end side is called "proximal end". A portion located at the distal end and in the vicinity of the distal end is called "distal end portion", and a portion located at the proximal end and in the vicinity of the proximal end is called "proximal end portion".

The plasma catheter 100 includes a hollow outer shaft 101, a hollow first inner shaft 102, a hollow second inner shaft 103 and a hollow distal-end tip 104 continuous with the first inner shaft 102. The outer shaft 101, the first inner shaft 102 and the second inner shaft 103 are long and have approximately circular cross sections. The distal-end tip 104 is tapered to gradually decrease its outer diameter toward its distal end and has an approximately circular cross section.

A first electrode 106 and a second electrode 107 are respectively mounted on an outer circumferential surface of the distal end portion and on an outer circumferential surface of the proximal end portion of the outer shaft 101. The second electrode 107 is connected with a terminal 502 of the RF generator 500 described later via a cable 40, a cable connector 21 and a cable 20. The first electrode 106 and the second electrode 107 are made of metal materials having electrical conductivity.

The first electrode 106 made of, for example, an alloy including a radiopaque material such as gold, platinum or tungsten serves as a radiopaque marker in a body cavity.

Braids 108 (shown in FIG. 3) serving as reinforcing members formed by knitting and braiding element wires are embedded inside of an outer circumferential surface of the outer shaft 101. The element wire forming the braid 108 is made of a metal material having electrical conductivity and may be made of, for example, stainless steel such as SUS 304, a nickel titanium alloy or an alloy including a radiopaque material such as gold, platinum or tungsten. The element wire forming the braid 108 may be made of a known metal material having electrical conductivity other than these examples. The braids 108 are connected with the first electrode 106 and the second electrode 107 to establish electrical continuity with the first electrode 106 and the second electrode 107. Accordingly, the second electrode 107, the braids 108 and the first electrode 106 form one electrical conductor.

Hollow coil bodies (not shown) formed by winding element wires may be embedded inside of the outer circumferential surface of the outer shaft 101, in place of the braids 108. Like the braids 108, the element wire forming the hollow coil body is made of a metal material having electrical conductivity and may be made of, for example, stainless steel such as SUS 304, a nickel titanium alloy or an alloy including a radiopaque material such as gold, platinum or tungsten. The wire forming the hollow coil body may be made of a known metal material having electrical conductivity other than these examples.

Referring to FIG. 3, the first inner shaft 102 and the second inner shaft 103 are inserted into an outer lumen 113 of the outer shaft 101. A hollow first wire shaft 117a and a hollow second wire shaft 117b are also inserted into the outer lumen 113. The first inner shaft 102, the second inner shaft 103, the first wire shaft 117a and the second wire shaft 117b are extended to be approximately parallel to each other along a longitudinal direction of the outer shaft 101.

Inside of the outer lumen 113 of the outer shaft 101 is sealed by a sealing member 114. The sealing member 114 is placed between an inner circumferential surface of the outer shaft 101 and an outer circumferential surface of the first inner shaft 102, an outer circumferential surface of the second inner shaft 103, an outer circumferential surface of the first wire shaft 117a and an outer circumferential surface of the second wire shaft 117b.

The imaging sensor 200 (not shown in FIG. 3) is inserted into a first inner lumen 115 of the first inner shaft 102. The plasma guide wire 400 and an ordinary guide wire for delivery (delivery guide wire 70 described later) (not shown in FIG. 3) are inserted into a second inner lumen 116 of the second inner shaft 103. A first wire 112a and a second wire 112b described later are respectively inserted into a first wire lumen 118a of the first wire shaft 117a and into a second wire lumen 118b of the second wire shaft 117b. The first wire 112a and the second wire 112b are respectively joined with the first wire piece 111c and the second wire piece 111d described later and are inserted into the first wire lumen 118a and into the second wire lumen 118b.

Referring to FIG. 1, an adjuster 105 is mounted on the proximal end of the outer shaft 101 and serves to open and close the stabilizer 111 described later and to move the imaging sensor 200 forward and backward in the first inner lumen 115.

The first inner shaft 102 and the second inner shaft 103 protrude from the distal end of the outer shaft 101. A protruded part of the second inner shaft 103 from the distal end of the outer shaft 101 is configured to be shorter than a protruded part of the first inner shaft 102 from the distal end of the outer shaft 101.

A distal end of the second inner shaft 103 is inclined toward the first inner shaft 102. An opening 103a is provided on the distal end of the second inner shaft 103 to communicate with the second inner lumen 116 of the second inner shaft 103 (shown in FIG. 3).

An opening 102a is provided on the outer circumferential surface of the first inner shaft 102 at a position between the distal end of the outer shaft 101 and a distal end of the first inner shaft 102 to communicate with the first inner lumen 115 of the first inner shaft 102 (shown in FIG. 3). The opening 102a is located on the distal end side to a maximum extent, such as to enable the delivery guide wire 70 to be visualized by the imaging sensor 200 in the process of inserting the plasma catheter 100 into a target site and positioning the plasma catheter 100. The opening 102a is provided on the same side as the second inner shaft 103 and the opening 103a and on extensions of the second inner shaft 103 and the opening 103a in a radial direction of the first inner shaft 102.

The distal-end tip 104 is joined with the distal end of the first inner shaft 102. An opening 104a is provided at a distal end of the distal-end tip 104. The opening 104a is arranged to communicate with an inner lumen (not shown) of the distal-end tip 104 and with the first inner lumen 115 of the first inner shaft 102.

In the inner lumen of the distal-end tip 104 and the first inner lumen 115 of the first inner shaft 102, a proximal end of the delivery guide wire 70 (shown in FIG. 6A) goes into the plasma catheter 100 through the opening 104a, goes out of the plasma catheter 100 through the opening 102a, goes into the second inner lumen 116 of the second inner shaft 103 through the opening 103a, goes through the second inner lumen 116 and goes out of the plasma catheter 100 through the proximal end of the second inner shaft 103.

A third opening (not shown) may be provided on the proximal end side of the opening 103a on the outer circumferential surface of the outer shaft 101 to pass through the second inner shaft 103 and communicate with the second inner lumen 116. In this case, the proximal end of the delivery guide wire 70 may be arranged to go out of the plasma catheter 100 through the third opening.

Instead of the opening 102a, another opening (not shown) may be provided on the outer circumferential surface of the first inner shaft 102. More specifically, another opening may be provided at a position opposed to the opening 102a, i.e., on the opposite side to the second inner shaft 103, in the radial direction of the first inner shaft 102. In this case, the proximal end of the delivery guide wire 70 may be arranged to enter from the opening 104a, to go through the inner lumen of the distal-end tip 104 and the first inner lumen 115 of the first inner shaft 102 and to go out from another opening.

Each of the outer shaft 101, the first wire shaft 117a, the second wire shaft 117b, the sealing member 114, the first inner shaft 102, the second inner shaft 103 and the distal-end tip 104 is made of a resin having insulation properties and may be made of, for example, a polyolefin such as polyethylene, polypropylene, ethylene-propylene copolymer, a polyester such as polyethylene terephthalate, a thermoplastic resin such as polyvinyl chloride, ethylene-vinyl acetate copolymer, crosslinked ethylene-vinyl acetate copolymer or polyurethane, polyamide elastomer, polyolefin elastomer, polyurethane elastomer, silicone rubber, or latex rubber. Each of the outer shaft 101, the first wire shaft 117a, the second wire shaft 117b, the sealing member 114, the first inner shaft 102, the second inner shaft 103 and the distal-end tip 104 may be made of a known material other than these examples.

A transducer 201 and a driving cable 202 of the imaging sensor 200 described later are placed in the protruded part of the first inner shaft 102 from the distal end of the outer shaft 101 or more specifically in a part of the first inner lumen 115 located between the distal end of the first inner shaft 102 and the distal end of the outer shaft 101. The transducer 201 serves to transmit ultrasonic waves to biological tissue via the first inner shaft 102 and receive reflected sound of the ultrasonic waves. The imaging console 300 obtains an image of the biological tissue, based on a difference between the transmitted sound and the received sound by the transducer 201. It is accordingly preferable that the part located between the distal end of the first inner shaft 102 and the distal end of the outer shaft 101 is formed from a resin having a difference of an acoustic impedance from that of the biological tissue, for example, polyethylene.

The distal-end tip 104 is placed on the distal end of the plasma catheter and is preferably made of a resin having the higher flexibility than those of the outer shaft 101, the first inner shaft 102 and the second inner shaft 103, for example, polyurethane elastomer, in order not to damage the biological tissue in the body cavity.

Any method may be employed to join the distal-end tip 104 with the first inner shaft 102. For example, a method using an insulating adhesive such as an epoxy-based adhesive may be employed for joining.

The first ring 109 and the second ring 110 are mounted on the outer circumferential surface of the first inner shaft 102. The first ring 109 is joined with the distal end of the first inner shaft 102. The first ring 109 may be joined with a proximal end of the distal-end tip 104 or may be joined with both the distal end of the first inner shaft 102 and the proximal end of the distal-end tip 104.

Any method may be employed to join the first ring 109 with the distal end of the first inner shaft 102, to join the first ring 109 with the proximal end of the distal-end tip 104, or to join the first ring 109 with the distal end of the first inner shaft 102 and with the proximal end of the distal-end tip 104. For example, a method using an insulating adhesive such as an epoxy-based adhesive may be employed for joining.

The first ring 109 may be placed on the proximal end side of the distal end of the first inner shaft 102.

The second ring 110 is placed on the proximal end side of the first ring 109 to be away from the first ring 109 and is mounted to be slidably movable along the longitudinal direction of the first inner shaft 102 on the outer circumferential surface of the first inner shaft 102. The stabilizer 111 comprised of the first stabilizer piece 111a and the second stabilizer piece 111b is mounted between the first ring 109 and the second ring 110 (the second stabilizer piece 111b is not shown in FIG. 1).

As described above, FIG. 2A is a schematic side view illustrating the distal end portion of the plasma catheter 100, and FIG. 2B and FIG. 2C are schematic bottom views illustrating the distal end portion of the plasma catheter 100. FIG. 2B illustrates the stabilizer 111 in the closed state. FIG. 2C illustrates the stabilizer 111 in the open state.

A distal end and a proximal end of the first stabilizer piece 111a are respectively joined with the first ring 109 and with the second ring 110. Similarly, a distal end and a proximal end of the second stabilizer piece 111b are respectively joined with the first ring 109 and with the second ring 110.

The first stabilizer piece 111a and the second stabilizer piece 111b are located at positions opposed to each other in the radial direction of the first inner shaft 102. More specifically, the first stabilizer piece 111a and the second stabilizer piece 111b are arranged to be placed on an identical virtual plane α as shown in FIG. 2B and FIG. 2C.

In FIG. 2A, on the other hand, the first inner shaft 102 and the second inner shaft 103 are arranged such that a longitudinal axis of the first inner shaft 102 and a longitudinal axis of the second inner shaft 103 are placed on an identical virtual plane β.

It is preferable that the first stabilizer piece 111a and the second stabilizer piece 111b are arranged, such that the virtual plane α and the virtual plane β are approximately orthogonal to each other.

Referring to FIG. 2B, in the closed state, the first stabilizer piece 111a and the second stabilizer piece 111b are extended in a longitudinal axis direction of the first inner shaft 102 between the first ring 109 and the second ring 110 to be approximately parallel to the first inner shaft 102. The second ring 110 is placed at a position on the proximal end side to a maximum extent, i.e., at a position closer to the opening 103a.

Referring to FIG. 2C, the second ring 110 is moved toward the distal end of the first inner shaft 102, so that the first stabilizer piece 111a and the second stabilizer piece 111b are expanded outward in the radial direction of the first inner shaft 102 to be in the open state.

The second ring 110 is placed to be located on the proximal end side of the opening 102a, in both the open state and the closed state of the stabilizer 111.

The first stabilizer piece 111a and the second stabilizer piece 111b may be formed in rectangular cross sectional shapes. In order to minimize the damage of the blood vessel by expansion of the stabilizer, forming the rectangular cross sectional shape reduces the pressure in a direction of expansion of the stabilizer 111 and causes a maximum stress to be applied for catheter fixation in a longitudinal side direction of the cross section.

In order to control the configuration of the stabilizer 111 during expansion, a groove or a cut may be provided in an outer circumferential surface of the first stabilizer piece 111a to be approximately perpendicular to a longitudinal axis direction of the first stabilizer piece 111a. Similarly, a groove or a cut may be provided in an outer circumferential surface of the second stabilizer piece 111b to be approximately perpendicular to a longitudinal axis direction of the second stabilizer piece 111b. Providing such grooves or cuts in the outer circumferential surfaces of the first stabilizer piece 111a and the second stabilizer piece 111b may cause the stabilizer 111 to have, for example, a hexagonal shape in bottom view during expansion of the stabilizer 111 (as shown in FIG. 2C). More specifically, in the bottom view, each of the first stabilizer piece 111a and the second stabilizer piece 111b may be formed in a trapezoidal shape (as shown in FIG. 2C).

Each of the stabilizer 111, the first ring 109 and the second ring 110 is made of a metal material or a resin material. The metal material may be, for example, stainless steel such as SUS 304, a nickel titanium alloy or an alloy including a radiopaque material such as gold, platinum or tungsten. The resin material may be, for example, a polyolefin such as polyethylene, polypropylene, ethylene-propylene copolymer, a polyester such as polyethylene terephthalate, a thermoplastic resin such as polyvinyl chloride, ethylene-vinyl acetate copolymer, crosslinked ethylene-vinyl acetate copolymer or polyurethane, polyamide elastomer, polyolefin elastomer, polyurethane elastomer, silicone rubber, or latex rubber. Each of the stabilizer 111, the first ring 109 and the second ring 110 may be made of a known metal material or a known resin material other than these examples.

When the stabilizer 111 is made of a nickel titanium alloy having shape-memory effect, it is preferable that the closed state of the stabilizer 111 is stored in advance in the nickel titanium alloy. This enables the stabilizer 111 to be relatively readily shifted from the open state to the closed state.

Any method may be employed to join the stabilizer 111 with the first ring 109 and the second ring 110. When the stabilizer 111, the first ring 109 and the second ring 110 are made of resins, when the stabilizer 111 is made of a metal material and the first ring 109 and the second ring 110 are made of resin materials, or when the stabilizer 111 is made of a resin material and the first ring 109 and the second ring 110 are made of metal materials, for example, a method using an adhesive such as an epoxy-based adhesive may be employed for joining. When the stabilizer 111, the first ring 109 and the second ring 110 are made of metal materials, a laser welding technique or a brazing technique using silver solder, gold solder, zinc or metal solder such as Sn—Ag alloy or Au—Sn alloy may be employed for joining.

Referring to FIGS. 2A to 2C, the first wire 112a and the second wire 112b are joined with the second ring 110 (only the first wire 112a is illustrated in FIG. 2A). More specifically, the first wire piece 111c described later is provided on the proximal end of the second ring 110 (as shown in FIG. 2E). The first wire 112a is placed to overlap with and to be joined with this first wire piece 111c (shown in FIG. 2E and FIG. 3) along the longitudinal axis direction of the first inner shaft 102. Similarly, the second wire piece 111d described later is provided on the proximal end of the second ring 110 (as shown in FIG. 2E). The second wire 112b is placed to overlap with and to be joined with this second wire piece 111d (shown in FIG. 2E and FIG. 3) along the longitudinal axis direction of the first inner shaft 102. The first wire piece 111c and the second wire piece 111d respectively pass through the first wire lumen 118a and the second wire lumen 118b described later to be extended to the middle of the outer shaft 101. The first wire 112a and the second wire 112b are respectively extended along outer circumferential surfaces of middle parts of the first inner shaft 102 and the second inner shaft 103 from a proximal end of the second ring 110 toward proximal ends of the first inner shaft 102 and the second inner shaft 103 in the longitudinal axis directions of the first inner shaft 102 and the second inner shaft 103.

The first wire 112a is configured to be longer than the first wire piece 111c, but the first wire 112a and the first wire piece 111c may have identical lengths. Similarly, the second wire 112b is configured to be longer than the second wire piece 111d, but the second wire 112b and the second wire piece 111d may have identical lengths.

Each of the first wire piece 111c and the second wire piece 111d is formed from a thin plate member having an approximately rectangular or circular arc-shaped cross section.

The first wire 112a and the second wire 112b are formed from round element wires of an approximately circular cross section. The first wire 112a is formed such that the outer diameter of a part that overlaps with the first wire piece 111c is smaller than the outer diameter of a part that does not overlap with the first wire piece 111c. Similarly, the second wire 112b is formed such that the outer diameter of a part that overlaps with the second wire piece 111d is smaller than the outer diameter of a part that does not overlap with the second wire piece 111d.

Referring to FIG. 2A, the first wire 112a and the first wire piece 111c are arranged to be approximately parallel to the first stabilizer piece 111a in the closed state. The first wire 112a and the first wire 111c are placed to be shifted to the second inner shaft 103-side relative to the first stabilizer piece 111a in a circumferential direction of the second ring 110 (in other words, in a circumferential direction of the first inner shaft 102). Similarly, the second wire 112b and the second wire piece 111d are arranged to be approximately parallel to the second stabilizer piece 111b in the closed state (not shown in FIG. 2A). The second wire 112b and the second wire piece 111d are placed on the second inner shaft 103-side relative to the second stabilizer piece 111b (not shown in FIG. 2A) in the circumferential direction of the second ring 110 (in other words, in the circumferential direction of the first inner shaft 102).

Referring to FIG. 3, the first wire 112a and the second wire 112b respectively pass through the first wire lumen 118a and the second wire lumen 118b of the outer shaft 101 and are connected with a first dial 105a of the adjuster 105 (shown in FIG. 1). Operation of the first dial 105a moves the second ring 110 on the outer circumferential surface of the first inner shaft 102 via the first wire 112a and the second wire 112b in a distal end direction of the first inner shaft 102, so as to expand the stabilizer 111. Simultaneously, the degree of expansion is adjustable to expand the stabilizer 111 to an optimum size, with using the imaging console described later to observe an image of biological tissue based on an ultrasonic signal from the imaging sensor 200 described later. This configuration minimizes the damage of the blood vessel. In the expanded state of the stabilizer 111, another operation of the first dial 105a uses the shape-memory effect of nickel titanium alloy to move the second ring 110 on the outer circumferential surface of the first inner shaft 102 via the first wire 112a and the second wire 112b toward the proximal end of the first inner shaft 102. This returns the stabilizer 111 to the closed state.

Each of the first wire 112a and the second wire 112b is made of a metal material or a resin material. The metal material may be, for example, chromium molybdenum steel, nickel chromium molybdenum steel, stainless steel such as SUS 304 or a nickel titanium alloy. The resin material may be, for example, super engineering plastic such as polyether ether ketone, polyether imide, polyamide imide, polysulfone, polyimide or polyether sulfone. Each of the first wire 112a and the second wire 112b may be made of a known metal material or a known resin material other than these examples.

The stabilizer 111, the first ring 109 and the second ring 110 may be formed as separate bodies or may be formed integrally. In the case of integral formation, as shown in FIG. 2D, the first ring 109, the second ring 110, the first stabilizer piece 111a and the second stabilizer piece 111b are formed by hollowing out a side wall of a cylindrical hollow pipe 60 that is made of a resin material or a metal material. In the case of FIG. 2D, the first wire 112a and the second wire 112b are directly joined with the second ring. In this case, any method may be employed to join the first wire 112a and the second wire 112b with the second ring 110. When the first wire 112a, the second wire 112b and the second ring 110 are made of resins, when the first wire 112a and the second wire 112b are made of metal materials and the second ring 110 is made of a resin material, or when the first wire 112a and the second wire 112b are made of resin materials and the second ring 110 is made of a metal material, for example, a method using an adhesive such as an epoxy-based adhesive may be employed for joining. When the first wire 112a, the second wire 112b and the second ring 110 are made of metal materials, a laser welding technique or a brazing technique using silver solder, gold solder, zinc or metal solder such as Sn—Ag alloy or Au—Sn alloy may be employed for joining.

As shown in FIG. 2E, when the stabilizer 111, the first ring 109 and the second ring 110 are formed integrally, the first wire piece 111c and the second wire piece 111d, in addition to the first ring 109, the second ring 110, the first stabilizer piece 111a and the second stabilizer piece 111b are formed by hollowing out a side wall of a cylindrical hollow pipe 60 that is made of a resin material or a metal material. The first wire piece 111c is arranged to be approximately parallel to the first stabilizer piece 111a in the closed state and is formed at a position shifted from the first stabilizer piece 111a to the second inner shaft 103-side (shown in FIG. 2A) in a circumferential direction of the second ring 110. Similarly, the second wire piece 111d is arranged to be approximately parallel to the second stabilizer piece 111b in the closed state and is formed at a position shifted from the second stabilizer piece 111b to the second inner shaft 103-side in the circumferential direction of the second ring 110.

In this case, the first wire 112a and the first wire piece 111c may be arranged to overlap with each other in the longitudinal axis direction of the first inner shaft 102 and to be joined with each other as described above. Similarly, the second wire 112b and the second wire piece 111d may be arranged to overlap with each other in the longitudinal axis direction of the first inner shaft 102 and to be joined with each other. The configuration shown in FIG. 2E is illustrated in the plasma catheter 100 in FIG. 1 to FIG. 2C, FIG. 3 and FIG. 6A to FIG. 6D.

As shown in FIG. 2F, when the stabilizer 111, the first ring 109 and the second ring 110 are formed integrally, the first wire piece 120 and the second wire piece 121, in addition to the first ring 109, the second ring 110, the first stabilizer piece 111a and the second stabilizer piece 111b are formed by hollowing out a side wall of a cylindrical hollow pipe 60 that is made of a resin material or a metal material.

The first wire piece 120 is comprised of a first curved portion 120a and a first linear portion 120b that is continuous with the first curved portion 120a. The first curved portion 120a is curved toward the second inner shaft 103 (shown in FIG. 2A), and the first linear portion 120b is extended to be approximately parallel to the first stabilizer piece 111a in the closed state.

The second wire piece 121 is comprised of a second curved portion 121a and a second linear portion 121b that is continuous with the second curved portion 121a. The second curved portion 121a is curved toward the second inner shaft 103 (shown in FIG. 2A), and the second linear portion 121b is extended to be approximately parallel to the second stabilizer piece 111b in the closed state. The first curved portion 120a and the second curved portion 121a may be formed linearly.

In this case, the first wire 112a and the first linear portion 120b of the first wire piece 120 may be arranged to overlap with each other in the longitudinal axis direction of the first inner shaft 102 and to be joined with each other. Similarly, the second wire 112b and the second linear portion 121b of the second wire piece 121 may be arranged to overlap with each other in the longitudinal axis direction of the first inner shaft 102 and to be joined with each other.

Any method may be employed to join the first wire 112a with the first wire piece 111c or with the first linear portion 120b of the first wire piece 120. When the first wire 112a, the first wire piece 111c and the first wire piece 120 are made of resins, when the first wire 112a is made of a metal material and the first wire piece 111c and the first wire piece 120 are made of resin materials, or when the first wire 112a is made of a resin material and the first wire piece 111c and the first wire piece 120 are made of metal materials, for example, a method using an adhesive such as an epoxy-based adhesive may be employed for joining. When the first wire 112a, the first wire piece 111c and the first wire piece 120 are made of metal materials, a laser welding technique or a brazing technique using silver solder, gold solder, zinc or metal solder such as Sn—Ag alloy or Au—Sn alloy may be employed for joining. The same applies to joining of the second wire 112b with the second wire piece 111d or with the second linear portion 121b of the second wire piece 121.

Referring to FIG. 3, the first wire 112a joined with the first wire piece 111c (shown in FIG. 2E) formed by hollowing out the side wall of the hollow pipe 60 is inserted into the first wire lumen 118a. The second wire 112b joined with the second wire piece 111d (shown in FIG. 2E) formed by hollowing out the side wall of the hollow pipe 60 is inserted into the second wire lumen 118b.

When the stabilizer 111, the first ring 109, the second ring 110, the first wire piece 120 and the second wire piece 121 are formed integrally by the method shown in FIG. 2F, the first linear portion 120b of the first wire piece 120 is placed instead of the first wire piece 111c and the second linear portion 121b of the second wire piece 121 is placed instead of the second wire piece 111d in the cross section of FIG. 3.

FIG. 1, FIG. 2A, FIG. 2B and FIG. 2C illustrate the configuration of expanding the stabilizer 111 by fixing the distal end of the stabilizer 111 and pressing the proximal end of the stabilizer 111 in a distal end direction. Another configuration may be employed to expand the stabilizer 111 by fixing the proximal end of the stabilizer 111 and pulling the distal end of the stabilizer 111 in a proximal end direction.

Referring to FIG. 1 and FIG. 4, the imaging sensor 200 is a long medical device and is comprised of the transducer 201 configured to transmit and receive ultrasonic waves, the hollow driving cable 202 and a connector 203. Electric wire (not shown) is connected with the transducer 201 and is connected with a cable 50 through an inner lumen of the hollow driving cable 202 and an inner lumen of the connector 203. The cable 50 is connected with the imaging console 300.

Operation of the imaging console 300 causes the transducer 201 placed on a distal end to transmit ultrasonic waves in a radial direction and to receive ultrasonic waves reflected from biological tissue, while rotating about a longitudinal axis thereof in a body cavity. The transducer 201 also serves to send the received ultrasonic waves through the electric wire and the cable 50 described above to the imaging console 300. In the plasma guide wire CTO system 1, the imaging sensor 200 is inserted in the first inner lumen 115 of the first inner shaft 102 to be used. The imaging sensor 200 is connected with a second dial 105b of the adjuster 105 between a distal end and a proximal end thereof. Operation of the second dial 105b causes the transducer 201 placed on the distal end of the imaging sensor 200 to move back and forth along the longitudinal axis direction of the first inner shaft 102.

The imaging console 300 controls rotation of the transducer 201 and transmission and reception of ultrasonic waves by the transducer 201. The imaging console 300 also serves to convert an ultrasonic signal received from the transducer 201 into an image signal and display the image signal on a display 302.

Referring to FIG. 1 and FIG. 5, the plasma guide wire 400 includes a core shaft 401, a hollow coil body 402, a distal-end tip 403 and a covering layer 404.

The core shaft 401 is made of a metal material having electrical conductivity and may be made of, for example, chromium molybdenum steel, nickel chromium molybdenum steel, stainless steel such as SUS 304 or a nickel titanium alloy. The core shaft 401 may be made of a known metal material other than these examples.

The coil body 402 is arranged to surround a distal end portion of the core shaft 401 and is formed in a cylindrical shape by spirally winding element wires. The element wire forming the coil body 402 is made of a metal material having electrical conductivity and may be made of, for example, stainless steel such as SUS 304, a nickel titanium alloy or an alloy including a radiopaque material such as gold, platinum or tungsten. The element wire forming the coil body 402 may be made of a known metal material other than these examples.

The distal-end tip 403 is a member configured to join a distal end of the core shaft 401 with a distal end of the coil body 402. The distal-end tip 403 is made of a metal material having electrical conductivity and may be made of, for example, chromium molybdenum steel, nickel chromium molybdenum steel, stainless steel such as SUS 304 or a nickel titanium alloy. The distal-end tip 403 is joined with the distal end of the core shaft 401 and the distal end of the coil body 402 by welding such as laser welding. The distal-end tip 403 may be formed by melting the distal end of the core shaft 401. In other words, the distal-end tip 403 and the core shaft 401 may be formed integrally. The distal-end tip 403 has a cone-shaped tapered distal end. In other words, the distal end of the distal-end tip 403 is formed in an arrowhead shape. An apex of the distal-end tip 403 may not be sharp-pointed but may be rounded or flat.

A middle joint portion 406 is a member configured to join the core shaft 401 with a proximal end of the coil body 402. The middle joint portion 406 is formed by brazing the core shaft 401 with the proximal end of the coil body 402 with a hard solder such as silver solder or gold solder. The middle joint portion 406 may be formed by welding, for example, laser welding, the core shaft 401 with the coil body 402.

The covering layer 404 is formed to cover from a proximal end portion of the distal-end tip 403 across the coil body 402 to a proximal end portion of the core shaft 401. The distal end of the distal-end tip 403 is exposed from a distal end of the covering layer 404. A proximal end of the core shaft 401 is exposed from a proximal end of the covering layer 404. The covering layer 404 is made of a resin having insulation properties and may be made of, for example, a polyolefin such as polyethylene, polypropylene, ethylene-propylene copolymer, a polyester such as polyethylene terephthalate, a thermoplastic resin such as polyvinyl chloride, ethylene-vinyl acetate copolymer, crosslinked ethylene-vinyl acetate copolymer or polyurethane, polyamide elastomer, polyolefin elastomer, polyurethane elastomer, silicone rubber, or latex rubber. The covering layer 404 may be made of super engineering plastic such as polyether ether ketone, polyether imide, polyamide imide, polysulfone, polyimide or polyether sulfone. The covering layer 404 may be made of a known material other than these examples.

A distal end joint portion 405 is a member configured to join the distal end of the covering layer 404 with the proximal end portion of the distal-end tip 403 and the distal end portion of the coil body 402 and has insulating properties and heat resistance. The distal end joint portion 405 may be formed, for example, from an adhesive such as an epoxy-based adhesive.

A proximal end joint portion 407 is a member configured to join the proximal end of the covering layer 404 with the proximal end portion of the core shaft 401 and has insulating properties. The proximal end joint portion 407 may be formed, for example, from an adhesive such as an epoxy-based adhesive.

It is preferable to form a bent first curve in a distal end portion of the plasma guide wire 400 (as shown in FIG. 1), prior to the procedure.

The plasma guide wire 400 is inserted through the connector 30 into the second inner lumen 116 of the second inner shaft 103 and is placed in use such that the distal end portion thereof protrudes from the distal end of the second inner shaft 103. The proximal end portion of the core shaft 401 of the plasma guide wire 400 is connected with a terminal 501 of the RF generator 500 described later via a cable connector 11 and a cable 10.

The RF generator 500 outputs high frequency power between the terminal 501 and the terminal 502. The terminal 501 is connected with the plasma guide wire 400 via the cable 10 and the cable connector 11. The terminal 502 is connected with the second electrode 107 of the plasma catheter 100 via the cable 20, the cable connector 21 and the cable 40.

In the state in which the plasma catheter 100 is transported to CTO and the distal end portion of the plasma guide wire 400 protrudes from the distal end of the second inner shaft 103, when high frequency power is output between the terminal 501 and the terminal 502, streamer discharge occurs at the distal-end tip 403, due to a voltage difference between the first electrode 106 of the plasma catheter 100 and the distal-end tip 403 of the plasma guide wire 400. Ablation of CTO is performed by this streamer discharge.

FIGS. 6A to 6D are diagrams illustrating one example of use of the plasma guide wire CTO system 1 in the case where CTO formed in coronary artery is canalized by an antegrade approach. FIGS. 6A to 6D illustrate a coronary artery 80, a CTO 81 occurring in the coronary artery 80, a false lumen 82 formed in or under inner membrane of the coronary artery 80, a fibrous film or plaque 83 (hereinafter simply referred to as fibrous film 83) that is present between the coronary artery 80 and the false lumen 82 and a true lumen, and a true lumen 84. The fibrous film 83 may be formed fibrously on the surface of a CTO lesion.

FIG. 6A illustrates the state in which the delivery guide wire 70 manipulated by the operator strays in the inner membrane of the coronary artery 80 and forms the falser lumen 82 in or under the inner membrane.

Referring to FIG. 6B, the operator inserts the proximal end of the delivery guide wire 70 from the opening 104a of the distal-end tip 104 of the plasma catheter 100 through the inner lumen of the distal-end tip 104, the first inner lumen 115 of the first inner shaft 102 (shown in FIG. 3), and the opening 102a of the first inner shaft 102 into the second inner lumen 116 of the second inner shaft 108. The operator then transports the plasma guide catheter 100 along the delivery guide wire 70 to the false lumen 82 and observes inside of the CTO lesion and inside of the false lumen with the imaging sensor 200. At this moment, the operator transports the plasma catheter 100 in the state in which the transducer 201 of the imaging sensor 200 is located very close to the proximal end side of the opening 102a in the first inner lumen 115 of the first inner shaft 102. This aims to move the observation site of the imaging sensor 200 by moving the plasma catheter 100. The operator checks an image of the coronary artery 80 from the transducer 201 on the display 302 and locates the plasma catheter 100 at an optimum position for penetration into the true lumen by the plasma guide wire 400, while transporting the plasma catheter 100.

After locating the plasma catheter 100 at the optimum position, the operator refers to the position of the delivery guide wire 70 on the display 302 and rotates the plasma catheter 100 such that a target true lumen is mutually opposed across the plasma catheter 100 and that the opening 103a as the outlet of the plasma guide wire 400 is located on the true lumen side and is mutually opposed to the true lumen. Accordingly, the delivery guide wire 70 serves as a landmark of the outlet of the plasma guide wire 400.

The operator operates the first dial 105a of the adjuster 105 to move the second ring 110 in the distal end direction via the first wire 112a and the second wire 112b and expand the stabilizer 111 (the expanded state of the stabilizer 111 is not illustrated in FIG. 6B). The stabilizer 111 is expanded to press the biological tissue in the false lumen and thereby fix the plasma catheter 100. While using the imaging sensor 200 to check the position and the degree of expansion of the stabilizer 111, the operator expands the stabilizer 111 and fixes the plasma catheter 100 at an optimum position where the plasma catheter 100 is fixed without excessively expanding the false lumen.

Referring to FIG. 6C, the operator uses the imaging sensor 200 to confirm successful fixation of the plasma catheter 100 and then removes the delivery guide wire 70. After removal of the delivery guide wire 70, the operator operates the second dial 105b of the adjuster 105 to move the imaging sensor 200 back and forth along the longitudinal axis direction of the first inner shaft 102 and observe and determine a site optimum for penetration into the true lumen.

Referring to FIG. 6D, after expanding the stabilizer 111 and fixing the plasma catheter 100, the operator inserts the plasma guide wire 400 into the second inner lumen 116 of the second inner shaft 103 and causes the plasma guide wire 400 to protrude from the opening 103a at the distal end, while checking the image of the coronary artery 80 from the transducer 201 on the display 302. The operator then guides the distal end of the plasma guide wire 400 to the optimum site for penetration described above, while checking the image of the plasma guide wire 400 from the transducer 201 on the display 302. A second curve may be formed on a distal end side or on a proximal end side of the first curve (shown in FIG. 1) of the plasma guide wire 400 required for such guiding. The operator operates the RF generator 500 to output high frequency power between the first electrode 106 and the distal-end tip 403 of the plasma guide wire 400 via the terminal 501 and the terminal 502. Streamer discharge accordingly occurs at the distal-end tip 403 of the plasma guide wire 400. This performs ablation of the fibrous film 83 and causes the plasma guide wire 400 to reach the true lumen 84.

The method shown in FIGS. 6A to 6D achieves canalization of the CTO 81 by the plasma guide wire CTO system 1.

<Modifications>

(1) In the above embodiment, the stabilizer piece 111a and the stabilizer piece 111b are formed from plate members (as shown in FIGS. 2D to 2F). The stabilizer piece 111a and the stabilizer piece 111b may be formed from mesh members made of a metal material or a resin material, instead of the plate members.

(2) A modification of the above embodiment may be further provided with a balloon configured to cover the stabilizer 111 (shown in FIGS. 2A to 2F) (hereinafter referred to as balloon A) and with a hollow inflation shaft that is connected with the balloon A and that is inserted in the outer lumen 113 of the outer shaft 101 (hereinafter referred to as inflation shaft A).

In this modified configuration, a fluid including a radiopaque material may be injected into the balloon A through the inflation shaft A. This configuration enables opening and closing of the stabilizer to be checked in an X-ray image.

(3) In the above embodiment, the mechanism of opening and closing the stabilizer 111 (hereinafter referred to as stabilizer opening/closing mechanism) is comprised of the first ring 109, the second ring 110, the first stabilizer piece 111a, the second stabilizer piece 111b, the first wire 112a and the second wire 112b (as shown in FIG. 2B and FIG. 2C).

A modification may employ an expandable and contractible balloon (hereinafter referred to as balloon B), in place of the stabilizer 111 and may employ a balloon B expansion/contraction mechanism to expand and contract the balloon B, in place of the stabilizer opening/closing mechanism. The balloon B expansion/contraction mechanism is connected with the balloon B and is configured by a hollow inflation shaft B that is inserted into the outer lumen 113 of the outer shaft 101. Injecting a fluid into the balloon B through the inflation shaft B expands the balloon B, whereas discharging the fluid from the balloon B contracts the balloon B. The balloon B preferably has a cross section in an elliptical shape.

(4) In the above embodiment, the imaging sensor 200 is inserted into the first inner lumen 115 of the first inner shaft 102 to obtain an image of intravascular biological tissue (as shown in FIGS. 6A to 6D). A modification may insert an OCT (optical coherence tomography) or a camera, in place of the imaging sensor 200, to obtain an image of intravascular biological tissue. In the case of using the OCT or the camera, a physiological saline solution is injected into the first inner lumen 115.

(5) In a modification of the above embodiment, the stabilizer 111 (shown in FIGS. 2A to 2F) may be formed from a member having a large difference of an acoustic impedance from that of the biological tissue. In another modification, the surface of the stabilizer 111 may be formed to have concavity and convexity, in order to facilitate reflection of ultrasonic waves from the transducer 201 of the imaging sensor 200.

In these modifications, the stabilizer 111 may serve as an orientation marker to check the orientation and the direction of the plasma catheter 100 on an image obtained by the imaging sensor 200. The stabilizer 111 may be in the open state or may be in the closed state when serving as the orientation marker.

(6) The above embodiment employs the stabilizer 111 comprised of the two stabilizer pieces (the first stabilizer piece 111a and the second stabilizer piece 111b) (as shown in FIGS. 2A to 2E).

A stabilizer comprised of three or more stabilizer pieces (hereinafter referred to as stabilizer A) may be employed in place of the stabilizer 111. The three or more stabilizer pieces may be arranged as follows in a cross section of the stabilizer A (hereinafter referred to as cross section A). In the cross section A, two stabilizer pieces (hereinafter referred to as stabilizer piece a and stabilizer piece b) out of the three or more stabilizer pieces are arranged to be opposed to each other. The remaining stabilizer pieces are arranged only in one of two areas that are adjacent to each other across a virtual line connecting the stabilizer piece a with the stabilizer piece b (hereinafter referred to as virtual line L) as the boundary.

The stabilizer A including the three or more stabilizer pieces arranged as described above may serve as an orientation marker of the higher accuracy to check the orientation and the direction of the plasma catheter 100 on an image obtained by the imaging sensor 200. In this application, it is preferable that the opening 103a of the second inner shaft 103 (shown in FIG. 1) is placed in one area or in the other area out of the two areas adjacent to each other across the virtual line L as the boundary in the cross section A.

(7) In the above embodiment, the stabilizer opening/closing mechanism (described above in Modification (3)) employs the configuration of moving the second ring 110 in the distal end direction by means of the first wire 112a and the second wire 112b to expand the stabilizer 111 (as shown in FIG. 2B and FIG. 2C).

A modification may be configured to move the second ring 110 in the distal end direction by utilizing a fluid-based pressing force, in place of the first wire 112a and the second wire 112b. For example, a balloon (hereinafter referred to as balloon C) may be mounted to the first inner shaft 102, and the proximal end of the second ring 110 may be mounted to a distal end of the balloon C.

In this modified configuration, injection of a fluid into the balloon C expands the balloon C and moves the second ring 110 in the distal end direction of the first inner shaft 102 by using a force of expanding the balloon C in the longitudinal axis direction of the first inner shaft 102, so as to expand the stabilizer 111. Discharge of the fluid from the balloon C moves the second ring 110 in the proximal end direction by using a force of contracting the balloon C in the longitudinal axis direction of the first inner shaft 102, so as to return the stabilizer 111 to the closed state.

In another modified configuration, the first ring 109 may be mounted to the outer circumferential surface of the first inner shaft 102 to be slidably movable in the longitudinal axis direction of the first inner shaft 102, and the second ring 110 may be fixed to the outer circumferential surface of the first inner shaft 102. This modified configuration moves the first ring 109 in the proximal end direction of the first inner shaft 102 by utilizing a fluid-based pressing force. In this modification, the first ring 109 is placed on the proximal end side of the distal end of the first inner shaft 102. For example, a balloon (hereinafter referred to as balloon D) may be mounted to the outer circumferential surface of the first inner shaft 102, and the distal end of the first ring 109 may be mounted to a proximal end of the balloon D.

In this modified configuration, injection of a fluid into the balloon D expands the balloon D and moves the first ring 109 in the proximal end direction of the first inner shaft 102 by using a force of expanding the balloon D in the longitudinal axis direction of the first inner shaft 102, so as to expand the stabilizer 111. Discharge of the fluid from the balloon D moves the first ring 109 in the distal end direction by using a force of contracting the balloon D in the longitudinal axis direction of the first inner shaft 102, so as to return the stabilizer 111 to the closed state.

(8) In the above embodiment, the stabilizer opening/closing mechanism (described above in Modification (3)) employs the configuration of moving the second ring 110 in the distal end direction by means of the first wire 112a and the second wire 112b to expand the stabilizer 111 (as shown in FIG. 2B and FIG. 2C).

A modification may employ a stabilizer that stores in advance the shape in the open state of the stabilizer 111 (hereinafter referred to as stabilizer B), in place of the stabilizer 111 and may employ a hollow outer sheath in a cylindrical shape to cover the outer circumference of the first inner shaft 102 and the stabilizer B in the open state and thereby forcibly set the stabilizer B in the closed state, in place of the first wire 112a and the second wire 112b.

In this modification, in place of the first wire shaft 117a and the second wire shaft 117b (shown in FIG. 3), a hollow outer sheath shaft is inserted into the outer lumen 113 of the outer shaft 101 to surround the first inner shaft 102. The outer sheath is configured to be movable in the longitudinal axis direction of the first inner shaft 102 between the outer circumferential surface of the first inner shaft 102 and an inner circumferential surface of the outer sheath shaft.

This modified configuration releases the stabilizer B to the open state by moving the outer sheath along the outer circumferential surface of the first inner shaft 102 to a proximal end side of the stabilizer B.

(9) In some cases, the stabilizer 111 may be caught by calcified tissue of CTO or by a stent placed in a blood vessel, so that the plasma catheter 100 may be stuck.

The stabilizer opening/closing mechanism (described above in Modification (3)) may be provided with a mechanism to release the plasma catheter 100 from the stuck state. For example, two slits may be formed in the first ring 109 in the longitudinal axis direction of the plasma catheter 100, so that the first ring 109 is separable into two. In another example, a fragile portion such as a cut may be provided in the distal end of each of the first stabilizer piece 111a and the second stabilizer piece 111b (shown in FIGS. 2D to 2F). Even when the stabilizer 111 is caught, this modified configuration cuts off the first ring 109 and readily releases the plasma catheter 100 by operating the first dial 105a of the adjuster 105 of the plasma catheter 100 (shown in FIG. 1) to pull the first wire 112a and the second wire 112b toward the proximal end side. In this modified configuration, the first ring 109 is joined with the first inner shaft 102 by crimping.

When the first ring 109 is not cut off by pulling the first wire 112a and the second wire 112b, another guide wire may be inserted from the opening 102a into the first inner lumen 115 of the first inner shaft 102 under guiding of the imaging sensor 200 to be placed in periphery from the opening 104a of the distal-end tip 104. A small-diameter balloon may be inserted along this guide wire into the first inner lumen 115 of the first inner shaft 102 and expanded, to cut off the first ring 109.

Providing the cut at the distal end of the first stabilizer piece 111a and/or the second stabilizer piece 111b enables the first stabilizer piece 111a and/or the second stabilizer piece 111b to be readily cut off from the first ring 109 and thereby readily releases the plasma catheter 100.

(10) In the embodiment described above, the first stabilizer piece 111a and the second stabilizer piece 111b are formed in the straight shape extended in the longitudinal axis direction of the inner shaft 102 (as shown in FIGS. 2D to 2F).

Instead of this straight shape, the first stabilizer piece 111a may be configured to have a large width portion between a distal end and a proximal end thereof. Similarly, the second stabilizer piece 111b may be configured to have a large width portion between a distal end and a proximal end thereof. The respective large width portions of the first stabilizer piece 111a and the second stabilizer piece 111b may have a circular arc shape, a rectangular shape or a trapezoidal shape.

Instead of this straight shape, the first stabilizer piece 111a and the second stabilizer piece 111b may be respectively configured to be curved.

The first stabilizer piece 111a and the second stabilizer piece 111b may be respectively provided with slits. Providing the slits enables the first stabilizer piece 111a and the second stabilizer piece 111b to be readily opened and closed.

(11) In the above embodiment, the shape of the first stabilizer piece 111a in the open state in the bottom view (hereinafter referred to as "bottom view open shape) is half the hexagonal shape (as shown in FIG. 2C). More specifically, the first stabilizer piece 111a and the second stabilizer piece 111b are respectively in the trapezoidal shape in bottom view (as shown in FIG. 2C).

Instead of the trapezoidal shape, the bottom view open shape of the first stabilizer piece 111a may be an arc shape such that a point present on the first stabilizer piece 111a and farthest from the first inner shaft 102 is located at a position closer to the distal end than the proximal end of the first stabilizer piece 111a. Similarly, the bottom view open shape of the second stabilizer piece 111b may be an arc shape such that a point present on the second stabilizer piece 111b and farthest from the first inner shaft 102 is located at a position closer to the distal end than the proximal end of the second stabilizer piece 111b.

Each of the bottom view open shapes of the first stabilizer piece 111a and the second stabilizer piece 111b may be a rectangular shape (half of an oblong shape or a square shape) or a circular arc shape (approximately semicircular shape), instead of the trapezoidal shape of the above embodiment or the above arc shape.

FIG. 7 is a diagram illustrating another example of use of the plasma guide wire CTO system 1 in the case where CTO formed in coronary artery is canalized by an antegrade approach. The operator first delivers the delivery guide wire 70 to the true lumen 84 on the proximal end side (proximal side) of the CTO 81. As in the example of FIG. 6B, the operator subsequently inserts the proximal end of the delivery guide wire 70 into the plasma catheter 100 and transports the plasma catheter 100 along the delivery guide wire 70 to the true lumen 84 on the proximal end side (proximal side) of the CTO 81. At this moment, the operator transports the plasma catheter 100 in the state in which the transducer 201 of the imaging sensor 200 is located near to the proximal end side of the opening 102a in the first inner lumen 115. The operator checks an image of the coronary artery 80 from the transducer 201 on the display 302 and locates the plasma catheter 100 at an optimum (or suitable) position for penetration by the plasma guide wire 400, while transporting the plasma catheter 100. The operator then refers to the position of the delivery guide wire 70 on the display 302 and rotates the plasma catheter 100 such that the opening 103a as the outlet of the plasma guide wire 400 is mutually opposed to a target site of ablation. Accordingly, like the example of FIG. 6B, in the example of FIG. 7, the delivery guide wire 70 serves as a landmark to locate the plasma catheter 100 at the optimum position.

The operator subsequently operates the first dial 105a of the adjuster 105 to move the second ring 110 in the distal end direction via the first wire 112a and the second wire 112b and expand the stabilizer 111 (the expanded state of the stabilizer 111 is not illustrated in FIG. 7). The stabilizer 111 is expanded to press the biological tissue (for example, blood vessel wall or CTO) and thereby fix the plasma catheter 100.

As in the example of FIG. 6C, the operator subsequently uses the imaging sensor 200 to confirm successful fixation of the plasma catheter 100, removes the delivery guide wire 70, and moves the imaging sensor 200 back and forth along the longitudinal axis direction of the first inner shaft 102 to observe and determine a site optimum for penetration into the CTO 81. After that, as shown in FIG. 7, the operator causes the plasma guide wire 400 to protrude from the opening 103a of the second inner lumen 116 and guides the distal end of the plasma guide wire 400 to the target site of ablation, while checking the image of the coronary artery 80 from the transducer 201 on the display 302.

As in the example of FIG. 6D, the operator subsequently operates the RF generator 500 to output high frequency power between the first electrode 106 and the distal-end tip 403 of the plasma guide wire 400 and performs ablation of the CTO 81 with the fibrous film 83 formed on the distal end side or other words, the CTO 81 with fibrosis of the distal end side (hereinafter the CTO 81 with the fibrous film 83 formed on the distal end side is simply referred to as CTO 81). The operator continuously performs ablation from the proximal end side (proximal side) to the distal end side (distal side) of the CTO 81 to connect the true lumen 84 on the proximal end side with the true lumen 84 on the distal end side and thereby canalize the CTO.

The plasma guide wire CTO system 1 of the first embodiment is not limitedly used for the approach from the false lumen 82 to the true lumen 84 (subintimal approach) described above with reference to FIGS. 6A to 6D but is also used for the approach to pass through the CTO 81 in the true lumen 84. This configuration enables the operator to perform ablation, while checking the target site of ablation on the image of the imaging sensor 200. This configuration suppresses the blood vessel wall from being mistakenly damaged especially at a start of ablation in the vicinity of an end face of the CTO 81 and improves the safety. This configuration also enables a target site optimum for ablation, for example, a soft portion of CTO, to be found at the start of ablation, thus allowing for efficient procedure and shortening the manipulation time. In the plasma guide wire CTO system 1 of the first embodiment, for example, the process of rotating the plasma catheter 100 for positioning and the process of expanding the stabilizer 111 to fix the plasma catheter 100 may be omitted.

In the first embodiment described above, the plasma guide wire CTO system 1 is one example of the "recanalization catheter system". The plasma catheter 100 is one example of the "catheter". The first inner lumen 115 is one example of the "first lumen", and the second inner lumen 116 is one example of the "second lumen". The outer shaft 101, the first inner shaft 102 located on the proximal end side of a distal end face of the outer shaft 101, the second inner shaft 103, the first and the second wire shafts 117a and 117b, and the sealing member 114 are one example of the "shaft". The first inner shaft 102 located on the distal end side of the distal end face of the outer shaft 101 is one example of the "extended shaft portion". The imaging sensor 200 is one example of the "sensor". The imaging sensor 200, the delivery guide wire 70 and the plasma guide wire 400 are one example of the "medical device". The opening 104a is one example of the "first opening", the opening 102a is one example of the "second opening", and the opening 103a is one example of the "third opening". The first ring 109, the second ring 110 and the stabilizer 111 are one example of the "expanding contracting portion". The first and the second wires 112a and 112b and the first and the second wire pieces 111c and 111d are one example of the "actuating portion". The braids 108 are one example of the "reinforcing member". The first electrode 106 is one example of the "electrode". The false lumen herein denotes any isolated cavity formed by the guide wire, other than the true lumen.

Examples of Advantageous Effects

As described above, in the plasma guide wire CTO system 1 of the first embodiment, the plasma catheter 100 (catheter) is provided with the shaft including the first inner lumen 115 (first lumen) and the second inner lumen 116 (second lumen) arranged to be adjacent to the first inner lumen 115. As shown in FIG. 6B and FIG. 6D, this configuration enables the imaging sensor 200 (sensor) and the medical device such as the delivery guide wire 70 and the plasma guide wire 400 (guide wire) to be simultaneously held in one catheter (in the plasma catheter 100).

The plasma catheter 100 of the first embodiment (catheter) is provided with the first inner shaft 102 (extended shaft portion) having the distal end portion that is extended toward the distal end side from the distal end portion of the second inner lumen 116 (second lumen). For example, as shown in FIGS. 6B to 6D, this configuration enables the distal end portion of the medical device inserted into the second inner lumen 116 (for example, the delivery guide wire 70 shown in FIG. 6B or the plasma guide wire 400 shown in FIG. 6D) to be observed with the imaging sensor 200 by inserting the imaging sensor 200 into the first inner lumen 115 (first lumen) and placing the transducer 201 of the imaging sensor 200 (portion configured to transmit and receive ultrasonic waves to and from biological tissue) in the first inner lumen 115 in the first inner shaft 102. This configuration enables the operator to recognize in real time the state of the inside of a biological lumen (for example, CTO) and the position of the distal end portion of, for example, the delivery guide wire 70 or the plasma guide wire 400 by only using a two-dimensional image formed by the imaging sensor 200. Accordingly, the plasma catheter 100 of the first embodiment allows for a procedure under guiding of the imaging sensor 200 without requiring the skill of separate intravascular manipulation of a plurality of devices and the skill of three-dimensional reconstruction of an IVUS image (imaging sensor image) and an X-ray image, which are conventionally required in the procedure under guiding of the imaging sensor 200 (for example, IVUS guide). Furthermore, the plasma catheter 100 of the first embodiment allows for a procedure only by referring to the image of the imaging sensor 200 and thereby reduces the frequency of obtaining X-ray images. This is expected to reduce the radiation exposure of the operator and the patient in X-ray photography and to reduce the use amount of a contrast agent in X-ray photography.

The plasma catheter 100 of the first embodiment (catheter) is provided with the first electrode 106 (electrode) that is placed on the surface of the outer shaft 101. As shown in FIG. 6D, this configuration allows for ablation of biological tissue using the plasma flow by insertion of the plasma guide wire 400 into the second inner lumen 116 (second lumen). This configuration allows for more reliable penetration of the biological tissue, compared with penetration of the biological tissue using an ordinary guide wire and is thus expected to improve the success rate of CTO canalization. In other words, even in the case that conventionally requires a shift to a retrograde approach for canalization, the combined use of the plasma catheter 100 of the first embodiment with the plasma guide wire 400 enables stable treatment by only an antegrade approach. Additionally, this antegrade approach is expected to shorten the manipulation time, compared with the retrograde approach.

As a result, the plasma catheter 100 of the first embodiment (catheter) improves the convenience of the procedure under guiding of the imaging sensor 200 (sensor) and is expected to reduce the radiation exposure, to reduce the use amount of the contrast agent, to improve the success rate of the procedure by the antegrade approach and to shortens the manipulation time.

In the plasma catheter 100 of the first embodiment (catheter), the opening 104a (first opening) that communicates with the first inner lumen 115 (first lumen) in the distal end portion and the opening 102a (second opening) that communicates with the first inner lumen 115 in a side face on the proximal end side of the opening 104a and on the side opposed to the second inner lumen 116 (second lumen) are respectively formed in the first inner shaft 102 (extended shaft portion). The opening 103a (third opening) that communicates with the second inner lumen 116 in the distal end portion is formed in the shaft. As shown in FIG. 6B, the delivery guide wire 70 is inserted from the opening 104a into the first inner lumen 115, is led out from the opening 102a, and is then inserted from the opening 103a into the second inner lumen 116, so as to be fixed in the distal end portion of the shaft. Fixation of the delivery guide wire 70 causes the delivery guide wire 70 to be continuously located in a fixed direction on the image of the imaging sensor 200 (sensor). As described above with reference to FIG. 6B, the operator moves the plasma catheter 100 in the longitudinal direction and rotates the plasma catheter 100 relative to the delivery guide wire 70 as the basis, while referring to the image of the imaging sensor 200. This controls the position of a target site for ablation by the plasma guide wire 400, relative to the plasma catheter 100 to an optimum position (optimum angle).

In the plasma catheter 100 of the first embodiment (catheter), the distal end portion of the first inner lumen 115 (first lumen) for the imaging sensor 200 (sensor) is used for fixation of the delivery guide wire 70 as shown in FIG. 6B. In other words, the first inner lumen 115 is shared by the delivery guide wire 70 and the imaging sensor 200. This configuration allows for reduction of the diameter of the plasma catheter 100 and enables the plasma catheter 100 to be readily inserted into a biological lumen (for example, inside of the coronary artery or inside of the CTO), compared with a configuration of providing a separate lumen for fixation of the delivery guide wire 70.

Furthermore, the plasma catheter 100 of the first embodiment (catheter) is also provided with the stabilizer 111 (expanding contracting portion) that is expandable and contractible in the radial direction. After the plasma catheter 100 is moved in the longitudinal direction and rotated to be positioned, the stabilizer 111 is expanded, so that the plasma catheter 100 is fixed at the position as shown in FIG. 6C. Fixing the plasma catheter 100 prior to ablation by the plasma guide wire 400 (shown in FIG. 6D) improves the operability of the plasma guide wire 400 in a biological lumen.

The stabilizer 111 (expanding contracting portion) is placed in the first inner shaft 102 (extended shaft portion) having the first inner lumen 115 (first lumen). Accordingly, when the stabilizer 111 is made of a material having a difference of an acoustic impedance from the acoustic impedance of the biological tissue, for example, the process of expanding the stabilizer 111 is more clearly observable by the imaging sensor 200 (sensor) inserted into the first inner lumen 115. This configuration enables the stabilizer 111 to be expanded safely, while reducing a potential damage in a biological lumen caused by excessive expansion of the stabilizer 111. Furthermore, even after fixation of the plasma catheter 100 shown in FIG. 6C, the imaging sensor 200 is movable in the first inner lumen 115 to move an image obtaining portion. Accordingly, this configuration enables a positional relationship between the distal-end tip 403 (distal end portion 9 of the plasma guide wire 400 and a target site for ablation to be observed by adjusting the image obtaining portion (transducer 201) to the distal end portion of the plasma guide wire 400. This allows for penetration of the target site, while reducing the frequency of obtaining X-ray images.

Moreover, in the plasma catheter 100 of the first embodiment (catheter), when the stabilizer 111 (expanding contracting portion) is made of a material having a larger acoustic impedance than the acoustic impedance of the biological tissue, the stabilizer 111 may serve as an orientation marker to check the orientation and the direction of the plasma catheter 100. When the stabilizer 111 is made of a radiopaque material, the stabilizer 111 may serve as an orientation marker to check the orientation and the direction of the plasma catheter 100 by imaging of the stabilizer 111 on an X-ray image obtained by X-ray photography.

Additionally, in the plasma catheter 100 of the first embodiment (catheter), the diameter of the first inner lumen 115 (first lumen) is larger than the diameter of the second inner lumen 116 (second lumen) as shown in FIG. 3. In general, the imaging sensor 200 (sensor) inserted into the first inner lumen 115 has a larger diameter than the diameter of the medical device (for example, the delivery guide wire 70 or the plasma guide wire 400) inserted into the second inner lumen 116. In the plasma catheter 100 of the first embodiment, the diameter of the first inner lumen 115 is larger than the diameter of the second inner lumen 116. The respective diameters of the first inner lumen 115 and the second inner lumen 116 may be determined according to the diameters of the respective devices inserted into the respective lumens. This configuration reduces potential errors in insertion of the devices and reduces the diameter of the plasma catheter 100, compared with a configuration that includes lumens of an identical diameter.

Furthermore, the plasma catheter 100 of the first embodiment (catheter) is provided with the braids 108 (reinforcing member) placed in a thick wall portion of the shaft as shown in FIG. 3. This configuration improves the torque transmission performance of the plasma catheter 100. The braids 108 are made of a material having electrical conductivity and are connected with the first electrode 106 (electrode) to establish electrical continuity with the second electrode 107. This configuration reduces the diameter of the plasma catheter 100, compared with a configuration provided with a separate member to establish electrical continuity with the first electrode 106. Additionally, when the braids 108 (reinforcing member) are made of a radiopaque material, this allows for imaging of the braids 108 on an X-ray image obtained by X-ray photography.

B. Second Embodiment

Figure 8:
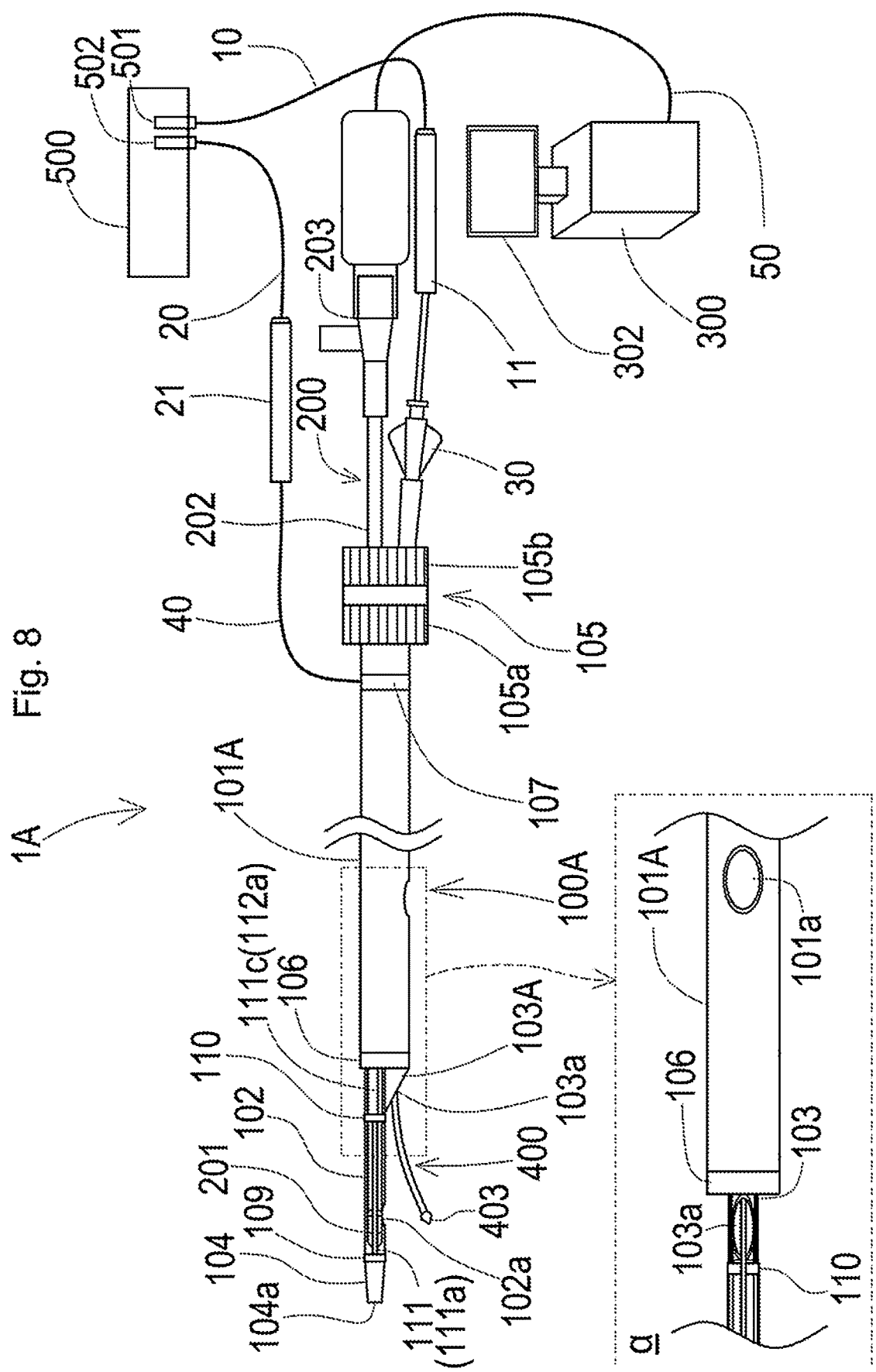
FIG. 8 is a schematic diagram illustrating the general configuration of a plasma guide wire CTO system according to a second embodiment.

FIG. 8 is a schematic diagram illustrating the general configuration of a plasma guide wire CTO system 1A according to a second embodiment. A lower part of FIG. 8 is a schematic bottom view illustrating a portion surrounded by a broken line frame in an upper part thereof. The plasma guide wire CTO system 1A of the second embodiment is provided with a plasma catheter 100A usable as a rapid exchangeable-type. The plasma catheter 100A differs from the plasma catheter 100 described in the first embodiment by an outer shaft 101A provided in place of the outer shaft 101 and a second inner shaft 103A provided in place of the second inner shaft 103. As shown in the lower part of FIG. 8, in the outer shaft 101A and the second inner shaft 103A, an opening 101*a* that communicates with the second inner lumen 116 is formed in a side face on a proximal end side of an opening 103*a*. The opening 101*a* is one example of the "fourth opening". The opening 101*a* is formed on an identical side with an opening 102*a* and is open to an approximately identical direction. In the bottom view of the lower part of FIG. 8 and the bottom views of FIG. 2B and FIG. 2C, the opening 102*a*, the opening 103*a* and the opening 101*a* are formed to be located on a virtual straight line that is extended in an approximately identical direction with longitudinal axis directions of the first inner shaft 102 and the outer shaft 101A.

Figure 9:
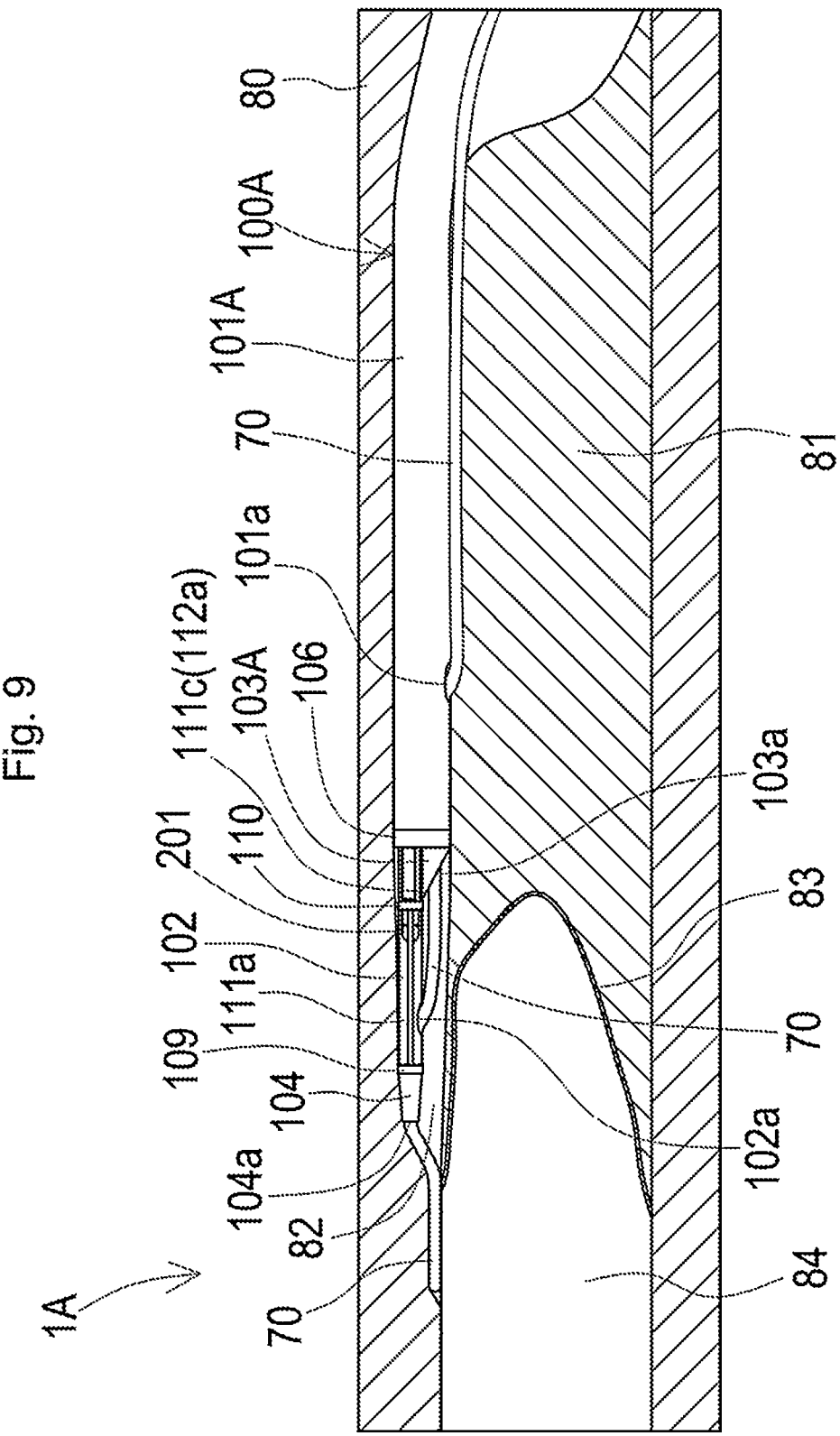
FIG. 9 is a diagram illustrating one example of use of the plasma guide wire CTO system according to the second embodiment.

FIG. 9 is a diagram illustrating one example of use of the plasma guide wire CTO system 1A according to the second embodiment. The plasma guide wire CTO system 1A of the second embodiment may be used by a similar procedure to that of FIG. 6B in the state in which the proximal end side of the delivery guide wire 70 inserted into the second inner lumen 116 further protrudes out from the opening 101*a*. The plasma catheter 100A may be provided with the opening 101*a* (fourth opening) that is formed in the side face on the proximal end side of the opening 103*a* (third opening) and that communicates with the second inner lumen 116 (second lumen) for a medical device such as the delivery guide wire 70. This configuration has similar advantageous effects to those of the first embodiment. The plasma catheter 100A of the second embodiment may be used as the rapid exchangeable-type catheter. This extends the applicable range of the procedure and further improves the usability.

C. Third Embodiment

Figure 10:
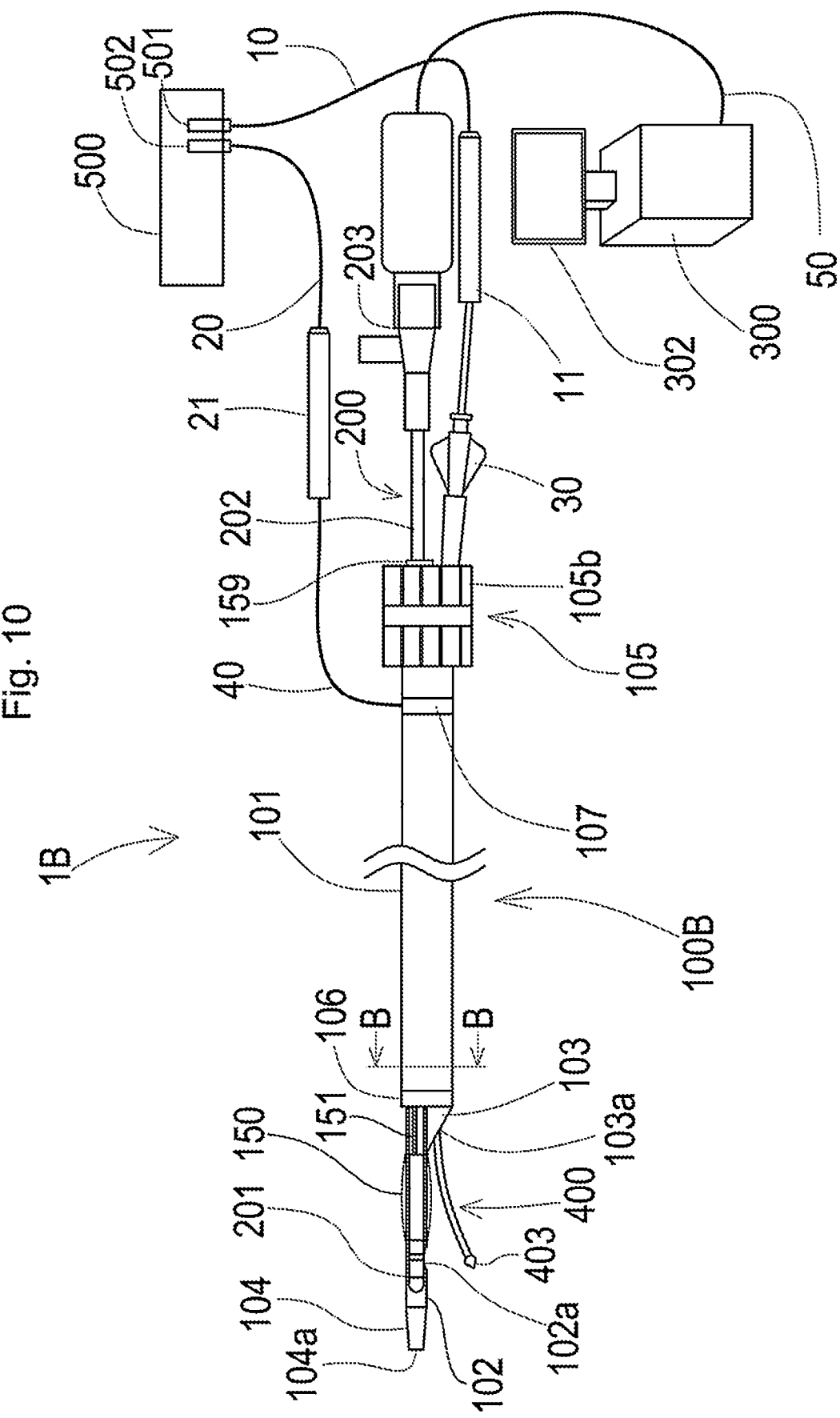
FIG. 10 is a schematic diagram illustrating the general configuration of a plasma guide wire CTO system according to a third embodiment.

FIG. 10 is a schematic diagram illustrating the general configuration of a plasma guide wire CTO system 1B according to a third embodiment. FIG. 11 is a schematic diagram illustrating a section of a plasma catheter 100B taken along a line B-B in FIG. 10. The plasma guide wire CTO system 1B of the third embodiment includes the plasma catheter 100B having a balloon as an expanding contracting portion. The plasma catheter 100B differs from the plasma catheter 100 described in the first embodiment by a balloon 150 serving as the expanding contracting portion and an inflation shaft 151 and a fill port 159 serving as the actuating portion, in place of the first ring 109, the second ring 110, the first and the second stabilizer pieces 111*a* and 111*b*, the first and the second wire pieces 111*c* and 111*d*, the first and the second wires 112*a* and 112*b*, the first and the second wire shafts 117*a* and 117*b* and the first dial 105*a* of the adjuster 105.

The balloon 150 is a tubular member that is expandable and contractible in a radial direction (direction perpendicular to a longitudinal direction) of the plasma catheter 100B. Like the first wire shaft 117*a* of the first embodiment, the inflation shaft 151 is a hollow long member having an approximately circular cross section and is inserted into the outer shaft 101. As shown in FIG. 10, a distal end side of the inflation shaft 151 is placed inside of the balloon 150, and a proximal end side of the inflation shaft 151 is connected with the fill port 159 that is provided in a proximal end face of the adjuster 105. The balloon 150 has a distal end portion that is joined with the first inner shaft 102 and a proximal end portion that is joined with the first inner shaft 102 and the inflation shaft 151, so as to be internally sealed. The balloon 150 is made of a material that is expandable and contractible with a change in internal pressure and that has flexibility for suppressing a potential intravascular damage and hardness for fixing the plasma catheter 100B. The balloon 150 may be made of, for example, a polyolefin such as polyethylene, polypropylene, ethylene-propylene copolymer, a polyester such as polyethylene terephthalate, a thermoplastic resin such as polyvinyl chloride, ethylene-vinyl acetate copolymer, crosslinked ethylene-vinyl acetate copolymer or polyurethane, polyamide elastomer, polyolefin elastomer, polyurethane elastomer, silicone rubber, or latex rubber.

In the plasma guide wire CTO system 1B of the third embodiment, the operator injects a fluid from the fill port 159 to expand the balloon 150 and thereby fixes the plasma catheter 100B in the coronary artery 80, instead of operating the first dial 105*a* of the adjuster 105 to expand the stabilizer 111. The cross sectional shape of the balloon 150 in the expanded state is preferably an approximately elliptical shape. The plasma catheter 100B may have an expanding contracting portion that has a different configuration from that of the stabilizer pieces. For example, the balloon 150 may be formed in a self-expandable type and may be provided with a sleeve configured to cover the balloon 150 and thereby keep the balloon 150 in the contracted state, in place of the inflation shaft 151 and the fill port 159. In this configuration, the operator causes the balloon 150 to be exposed from the sleeve and thereby fixes the plasma catheter 100B in the coronary artery 80, instead of expanding the stabilizer 111. This configuration also has similar advantageous effects to those of the first embodiment.

D. Fourth Embodiment

Figure 12A:
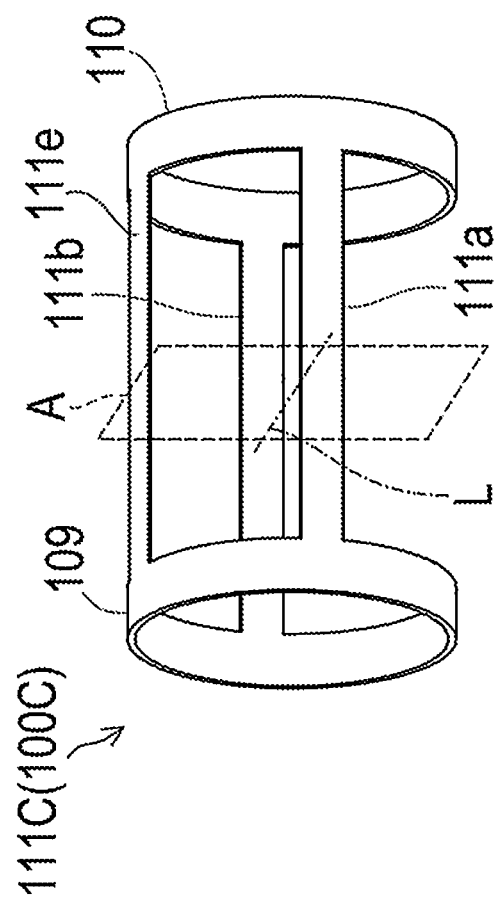
FIG. 12A is a diagram illustrating one example of an expanding contracting portion according to a fourth embodiment.
Figure 12B:
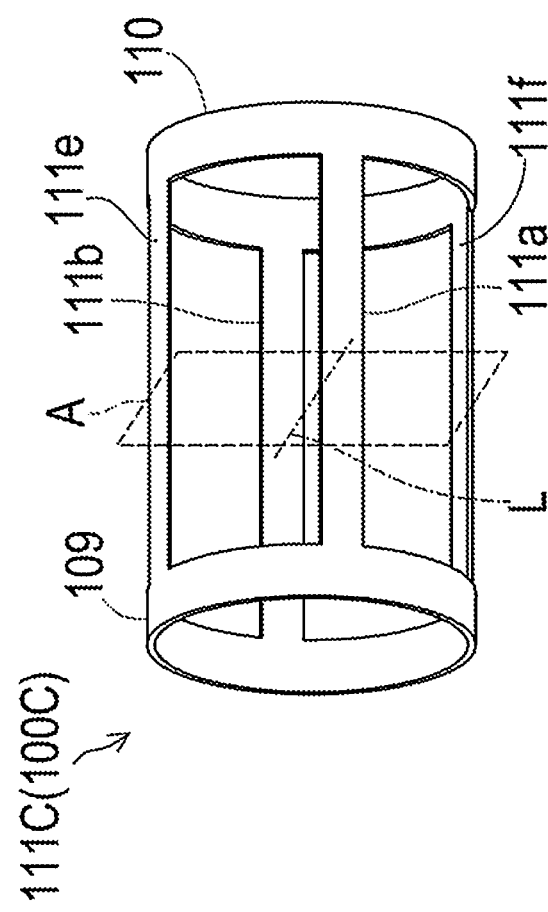
FIG. 12B is a diagram illustrating another example of the expanding contracting portion according to the fourth embodiment.

FIGS. 12A and 12B are schematic diagrams illustrating expanding contracting portions according to a fourth embodiment. FIG. 12A illustrates one example of the expanding contracting portion according to the fourth embodiment. A plasma catheter 100C of the fourth embodiment is provided with a stabilizer 111C in a different configuration from that of the first embodiment.

The stabilizer 111C shown in FIG. 12A includes a third stabilizer piece 111*e*, in addition to a first stabilizer piece 111*a* and a second stabilizer piece 111*b* described in the first embodiment. In a cross section A of the stabilizer 111C shown by the broken line, the first stabilizer piece 111*a* and the second stabilizer piece 111*b* are arranged to be opposed to each other. A virtual line L (one-dot chain line) connecting respective centers of the first and the second stabilizer pieces 111*a* and 111*b* is defined on the cross section A. The third stabilizer piece 111*e* is placed in one area out of two areas that are adjacent to each other across the virtual line L as the boundary (these areas are called "upper area" and "lower area" for descriptive purposes). More specifically, in the illustrated example, the third stabilizer piece 111*e* is placed in the upper area on the cross section A and is arranged at a position that has approximately identical lengths from the first stabilizer piece 111*a* and the second stabilizer piece 111*b*. This configuration enables the stabilizer 111C to serve as an orientation marker of the higher accuracy for checking the orientation and the direction of the plasma catheter 100C on an image of the imaging sensor 200.

The stabilizer 111C shown in FIG. 12B further includes a fourth stabilizer piece 111*f*, in addition to the third stabilizer piece 111*e* described above. The fourth stabilizer piece 111*f* is placed in the other area out of the two areas adjacent to each other across the virtual line L as the boundary. More specifically, in the illustrated example, the fourth stabilizer piece 111f is placed in the lower area on the cross section A and is arranged at a position that has approximately identical lengths from the first stabilizer piece 111a and the second stabilizer piece 111b. The number of stabilizer pieces provided in the stabilizer 111C is determined arbitrarily and may be one or may be three or more. These configurations have similar advantageous effects to those of the first embodiment.

E. Fifth Embodiment

FIGS. 13A and 13B are schematic diagrams illustrating expanding contracting portions according to a fifth embodiment. FIG. 13A illustrates one example of the expanding contracting portion according to the fifth embodiment. A plasma catheter 100D of the fifth embodiment is provided with a stabilizer 111D in a different configuration from that of the first embodiment.

The stabilizer 111D shown in FIG. 13A includes a first ring 109D, in place of the first ring 109 described in the first embodiment. The first ring 109D has two separating portions 109s provided in a longitudinal axis direction of the plasma catheter 100D. During the procedure described above with reference to FIGS. 6A to 6D, the stabilizer 111d may be caught by calcified tissue of the CTO 81 or by a stent placed in a blood vessel, so that the plasma catheter 100D is likely to be stuck in the coronary artery 80. In this case, the separating portions 109s serve to separate the stabilizer 111D as shown on the right side of FIG. 13A, so as to release the plasma catheter 100D. The separating portions 109s may be configured as cuts (slits) provided in a thick wall portion of the first ring 109D. The separating portions 109s may also be configured as fragile portions by reducing the wall thickness of part of the first ring 109D, by providing through holes or by changing the material.

When the stabilizer 111D is caught, the operator operates the first dial 105a of the adjuster 105 (shown in FIG. 1) of the plasma catheter 100D to pull the first and the second wires 112a and 112b toward the proximal end side. This causes tears at the separating portions 109s to separate the first ring 109D as shown on the right side of FIG. 13A. As a result, the operator can readily release the plasma catheter 100D. Providing the respective separating portions 109s at illustrated positions causes the respective parts of the torn first ring 109D to be attached to the first and the second stabilizer pieces 111a and 111b. This configuration suppresses any part of the torn first ring 109D from being left in the body.

FIG. 13B illustrates another example of the expanding contracting portion according to the fifth embodiment. In the stabilizer 111D shown in FIG. 13B, two separating portions 111s are formed at boundaries between the first ring 109D and the first and the second stabilizer pieces 111a and 111b. The first ring 109D is joined with the surface of the first inner shaft 102, for example, by pressure bonding or by using an adhesive. Like the separating portions 109s, the separating portions 111s may be configured by cuts or by fragile portions. As in the case of FIG. 13A, when the stabilizer 111D is caught, the operator pulls the first and the second wires 112a and 112b toward the proximal end side. This causes tears at the separating portions 111s to separate the first ring 109D as shown on the right side of FIG. 13B. The first ring 109D is joined with the surface of the first inner shaft 102. This configuration suppresses any part of the torn first ring 109D from being left in the body.

The expanding contracting portion may have various modified configurations and may have a configuration other than those described in the first embodiment. Such configurations also have similar advantageous effects to those of the first embodiment. Even when the plasma catheter 100D is stuck in the coronary artery 80, the expanding contracting portions of the fifth embodiment can readily release the plasma catheter 100D.

F. Sixth Embodiment

Figure 14B:
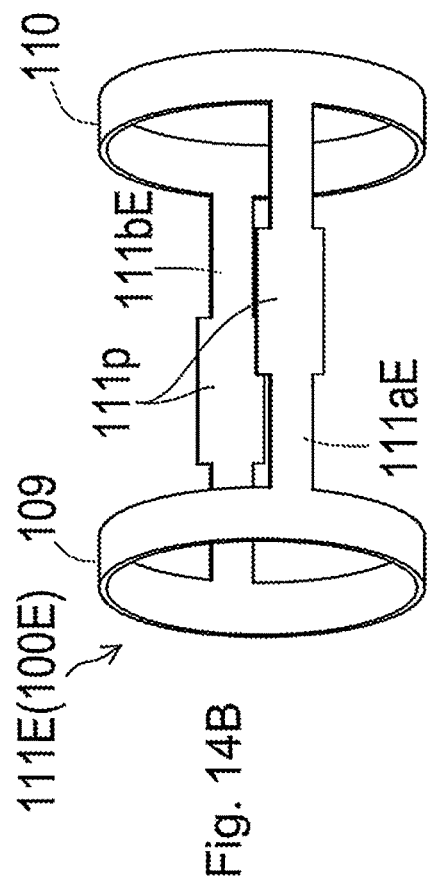
FIG. 14B is a diagram illustrating another example of the expanding contracting portion according to the sixth embodiment.
Figure 14A:
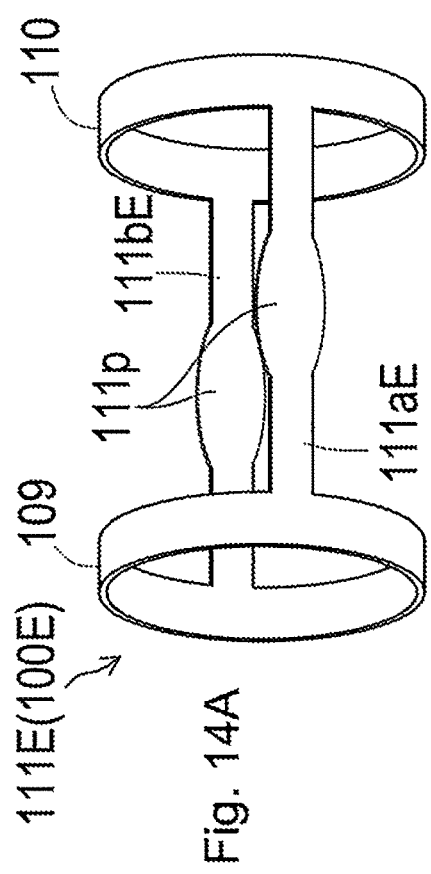
FIG. 14A is a diagram illustrating one example of the expanding contracting portion according to a sixth embodiment.
Figure 14C:
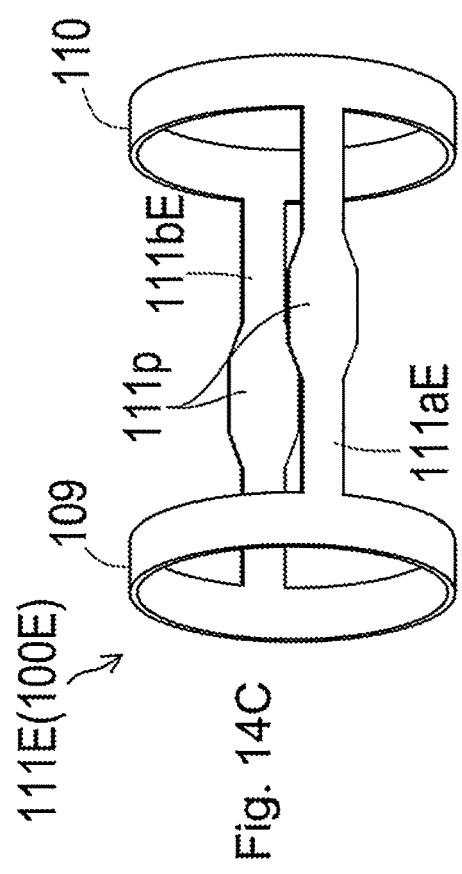
FIG. 14C is a diagram illustrating another example of the expanding contracting portion according to the sixth embodiment.

FIGS. 14A to 14C are schematic diagrams illustrating expanding contracting portions according to a sixth embodiment. FIG. 14A illustrates one example of the expanding contracting portion according to the sixth embodiment. FIG. 14B and FIG. 14C illustrate other examples of the expanding contracting portion according to the sixth embodiment. A plasma catheter 100E of the sixth embodiment is provided with a stabilizer 111E in a different configuration from that of the first embodiment. The stabilizer 111E of the sixth embodiment includes first and second stabilizer pieces 111aE and 111bE, in place of the first and the second stabilizer pieces 111a and 111b described in the first embodiment. Each of the first and the second stabilizer pieces 111aE and 111bE shown in FIGS. 14A to 14C has a wide portion 111p that is formed wide between a distal end portion and a proximal end portion. The wide portion 111p may be formed in a circular arc shape (approximately elliptical shape) shown in FIG. 14A, in a rectangular shape shown in FIG. 14B or in a trapezoidal shape shown in FIG. 14C.

FIGS. 15A and 15B are schematic diagrams illustrating expanding contracting portions according to the sixth embodiment. FIGS. 15A and 15B illustrate other examples of the expanding contracting portion according to the sixth embodiment. Each of the first stabilizer piece 111aE and the second stabilizer piece 111bE shown in FIG. 15A has a curved portion 111w that is formed by bending the stabilizer piece in an approximately S shape between a distal end portion and a proximal end portion. The curved portion 111w may be formed in any of various shapes, for example, an approximately C shape or an approximately O shape. Each of the first stabilizer piece 111aE and the second stabilizer piece 111bE shown in FIG. 15B has a cut (slit) 111s that is extended in a longitudinal direction of the plasma catheter 100E. In the example of FIG. 15B, when the first and the second wires 112a and 112b are pushed in toward the distal end portion by operation of the first dial 105a of the adjuster 105 (shown in FIG. 1), the first and the second stabilizer pieces 111aE and 111bE are bent in the vertical direction from the respective cuts 111s to be expanded as shown on the right side of the drawing.

The expanding contracting portion may have various modified configurations and may have a configuration other than those described in the first embodiment. Such configurations also have similar advantageous effects to those of the first embodiment. In the expanding contracting portions of the sixth embodiment, the wide portions 111p as shown in FIGS. 14A to 14C, the curved portions 111w as shown in FIG. 15A or the first and the second stabilizer pieces 111aE and 111bE bent in the vertical direction as shown in FIG. 15B engage with the biological tissue and thereby more reliably fix the plasma catheter 100E in the coronary artery 80.

G. Seventh Embodiment

Figure 16A:
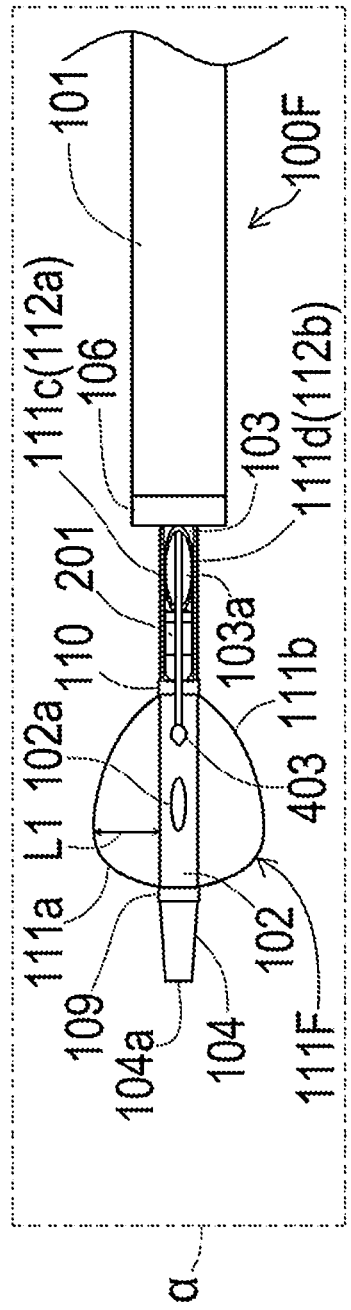
FIG. 16A is a schematic bottom view illustrating one example of a distal end portion of a plasma catheter.
Figure 16B:
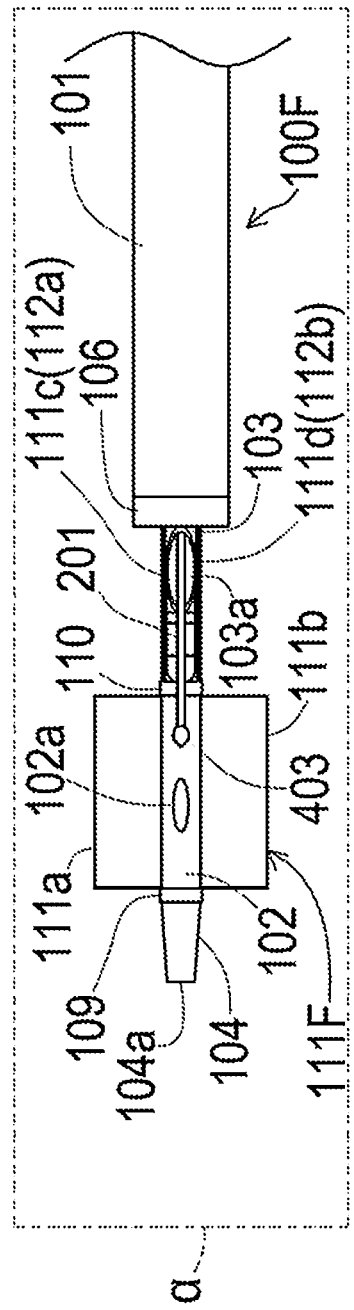
FIG. 16B is a schematic bottom view illustrating another example of the distal end portion of the plasma catheter.
Figure 16C:
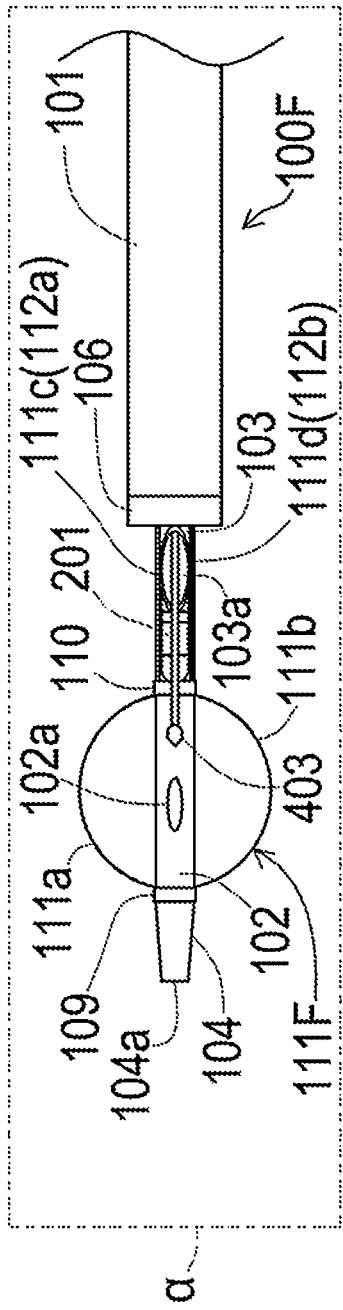
FIG. 16C is a schematic bottom view illustrating another example of the distal end portion of the plasma catheter.

FIGS. 16A to 16C are schematic diagrams illustrating distal end portions of a plasma catheter 100F according to a seventh embodiment. FIG. 16A is a schematic bottom view illustrating one example of the distal end portion of the plasma catheter 100F. FIGS. 16B and 16C are schematic bottom views illustrating other examples of the distal end portion of the plasma catheter 100F. The plasma catheter 100F of the seventh embodiment is provided with a stabilizer 111F that is expanded in different shapes from that of the first embodiment. A bottom view shape of the stabilizer 111F in the expanded state may be an approximately teardrop shape as shown in FIG. 16A, an approximately rectangular shape as shown in FIG. 16B or an approximately circular shape as shown in FIG. 16C. In the case of the approximately teardrop shape shown in FIG. 16A, it is preferable that a portion having a longest distance L1 from the surface of the first inner shaft 102 to the stabilizer 111F (first and second stabilizer pieces 111a and 111b) is located on a distal end side of the middle of the stabilizer 111F. The expanding contracting portion in the expanded state may have various modified configurations and may have a configuration other than those described in the first embodiment. Such configurations also have similar advantageous effects to those of the first embodiment.

H. Eighth Embodiment

FIGS. 17A and 17B are schematic diagrams illustrating a distal end portion of a plasma catheter 100G according to an eighth embodiment. FIG. 17A is a schematic side view illustrating one example of the distal end portion of the plasma catheter 100G. FIG. 17B is a schematic bottom view illustrating one example of the distal end portion of the plasma catheter 100G. FIG. 18 is a schematic diagram illustrating a cross section of the plasma catheter 100G taken along a line C-C in FIG. 17A. The plasma catheter 100G of the eighth embodiment has an integral shaft of an outer shaft and first and second inner shafts.

More specifically, in place of the outer shaft 101, the first inner shaft 102, the second inner shaft 103 and the sealing member 114 described in the first embodiment, the plasma catheter 100G includes an integrally molded shaft 101G (shown in FIG. 18). As shown in FIG. 18, a first inner lumen 115 for insertion of the imaging sensor 200 and a second inner lumen 116 for insertion of the delivery guide wire 70 and the plasma guide wire 400 are formed inside of the shaft 101G. An electrically conductive element wire 108G is also embedded inside of the shaft 101G to connect the first electrode 106 with the second electrode 107 such as to establish electrical continuity.

A distal end portion of the shaft 101G is provided with an extended shaft portion 102G that includes the first inner lumen 115 and that is extended toward a distal end side of the distal end portion of the second inner lumen 116. An opening 104a is formed in a distal end face of the extended shaft portion 102G. An opening 102a is formed in a side face of the extended shaft portion 102G on a side opposed to the second inner lumen 116. An opening 103a that communicates with the second inner lumen 116 is formed in a distal end face of the shaft 101G. The extended shaft portion 102G may be integrally molded with the shaft 101 or may be separately formed and joined with a distal end portion of the shaft 101G.

The plasma catheter 100G of the eighth embodiment may be provided or may not be provided with the stabilizer 111 (first and second stabilizer pieces 111a and 111b), the first and the second rings 109 and 110, the first and the second wire pieces 111c and 111d, the first and the second wires 112a and 112b, the first and the second wire shafts 117a and 117b, the first dial 105a, the distal-end tip 104 and the braids 108 described in the first embodiment, other than the outer shaft 101, the first inner shaft 102, the second inner shaft 103 and the sealing member 114 described above. The element wire 108G may not be embedded in the shaft 101G but may be placed on the surface of the shaft 101G. The plasma catheter 100G may have various modified configurations and may have a configuration other than those described in the first embodiment. Such configurations also have similar advantageous effects to those of the first embodiment.

I. Ninth Embodiment

FIG. 19 is a schematic diagram illustrating the general configuration of a plasma guide wire CTO system 1H according to a ninth embodiment. FIG. 20 is a schematic diagram illustrating a section of a plasma catheter 100H taken along a line D-D in FIG. 19. The plasma guide wire CTO system 1H of the ninth embodiment includes the plasma catheter 100H, in place of the plasma catheter 100 described in the first embodiment. For convenience of illustration, the plasma guide wire 400 connected with the cable connector 11 is omitted from the illustration in FIG. 19. As shown in FIG. 20, the plasma catheter 100H is not provided with the second inner shaft 103 described in the first embodiment. Accordingly, the plasma catheter 100H is configured without the second inner lumen 116 and the opening 103a that are formed by the second inner shaft 103 and is configured to have only the first inner lumen 115 used for insertion of a medical device.

The plasma guide wire CTO system 1H of the ninth embodiment achieves canalization of CTO as follows. The proximal end of the delivery guide wire 70 is inserted from an opening 104a to pass through the inner lumen of the distal-end tip 104 and the first inner lumen 115 of the first inner shaft 102 (shown in FIG. 20) and protrudes out from an opening 102a of the first inner shaft 102. The plasma catheter 100H is transported along the delivery guide wire 70 to the false lumen 82. At this moment, the operator places the plasma catheter 100H at an optimum position for penetration into the true lumen by the plasma guide wire 400, while checking the image of the coronary artery 80 by the imaging sensor 200 inserted into the first inner lumen 115. After placing the plasma catheter 100H at the optimum position, the operator rotates the plasma catheter 100H as needed with regard to the position of the delivery guide wire 70 on the image by the imaging sensor 200 as the indication.

The operator subsequently operates the first dial 105a to expand the stabilizer 111. Expansion of the stabilizer 111 fixes the plasma catheter 100H. The operator then removes the delivery guide wire 70 and the imaging sensor 200 and newly inserts the plasma guide wire 400 into the first inner lumen 115. The operator transports the distal end portion of the plasma guide wire 400 to a distal end portion of the plasma catheter 100H and causes the distal end portion of the plasma guide wire 400 to protrude out from the opening 102a or from the opening 104a. When the optimum site for penetration is located near to the distal end portion of the plasma catheter 100H, it is preferable to protrude the plasma guide wire 400 from the opening 104a. When the optimum site for penetration is located near to a side face of the plasma catheter 100H, on the other hand, it is preferable to protrude the plasma guide wire 400 from the opening 102a. The operator then operates the RF generator 500 to cause streamer discharge at the distal-end tip 403 of the plasma guide wire 400 and performs ablation of the CTO 81.

The plasma catheter 100H may have various modified configurations. For example, the number of lumens for insertion of a medical device may be one or may be three or more. In the plasma guide wire CTO system 1H of the ninth embodiment, the plasma catheter 100H (catheter) is provided with one first inner lumen 115 (lumen, shown in FIG. 20) for insertion of a medical device. This configuration reduces the diameter of the plasma catheter 100H. The distal end portion of the shaft is provided with the first inner shaft 102 (extended shaft portion) having the distal end portion that is extended toward the distal end side of the distal end portion of the outer shaft 101. This configuration enables inside of the false lumen 82 to be observed with the higher accuracy by inserting the imaging sensor 200 (sensor) into the first inner lumen 115 and placing the transducer 201 of the imaging sensor 200 in the first inner lumen 115 in the first inner shaft 102. The first electrode 106 (electrode) is provided on the outer circumferential surface of the outer shaft 101. This configuration allows for ablation of biological tissue using the plasma flow by insertion of the plasma guide wire 400 into the first inner lumen 115. Additionally, after the plasma catheter 100H is moved in the longitudinal direction and is rotated to be positioned, the stabilizer 111 (expanding contracting portion) that is expandable and contractible in the radial direction is expanded, so that the plasma catheter 100H is fixed at the position.

The plasma catheter 100H of the ninth embodiment is provided with the opening 104a (first opening) formed in the distal end portion of the first inner shaft 102 (extended shaft portion), which is extended toward the distal end side of the distal end portion of the outer shaft 101, to communicate with the first inner lumen 115 (lumen) and with the opening 102a (second opening) formed in a side face on a proximal end side of the opening 104a to communicate with the first inner lumen 115. This configuration enables the proximal end side of the delivery guide wire 70 to be inserted from the opening 104a into the first inner lumen 115, to pass through the first inner lumen 115 and to protrude out. The plasma catheter 100H can thus be used as a rapid exchangeable-type catheter. When the plasma guide wire 400 is inserted in the first inner lumen 115 in use, protrusion of the distal end portion of the plasma guide wire 400 from the opening 104a facilitates ablation of biological tissue located in the vicinity of the distal end portion of the plasma catheter 100H. Furthermore, protrusion of the distal end portion of the plasma guide wire 400 from the opening 102a facilitates ablation of biological tissue located in the vicinity of the side face of the plasma catheter 100H.

J. Tenth Embodiment

Figure 21:
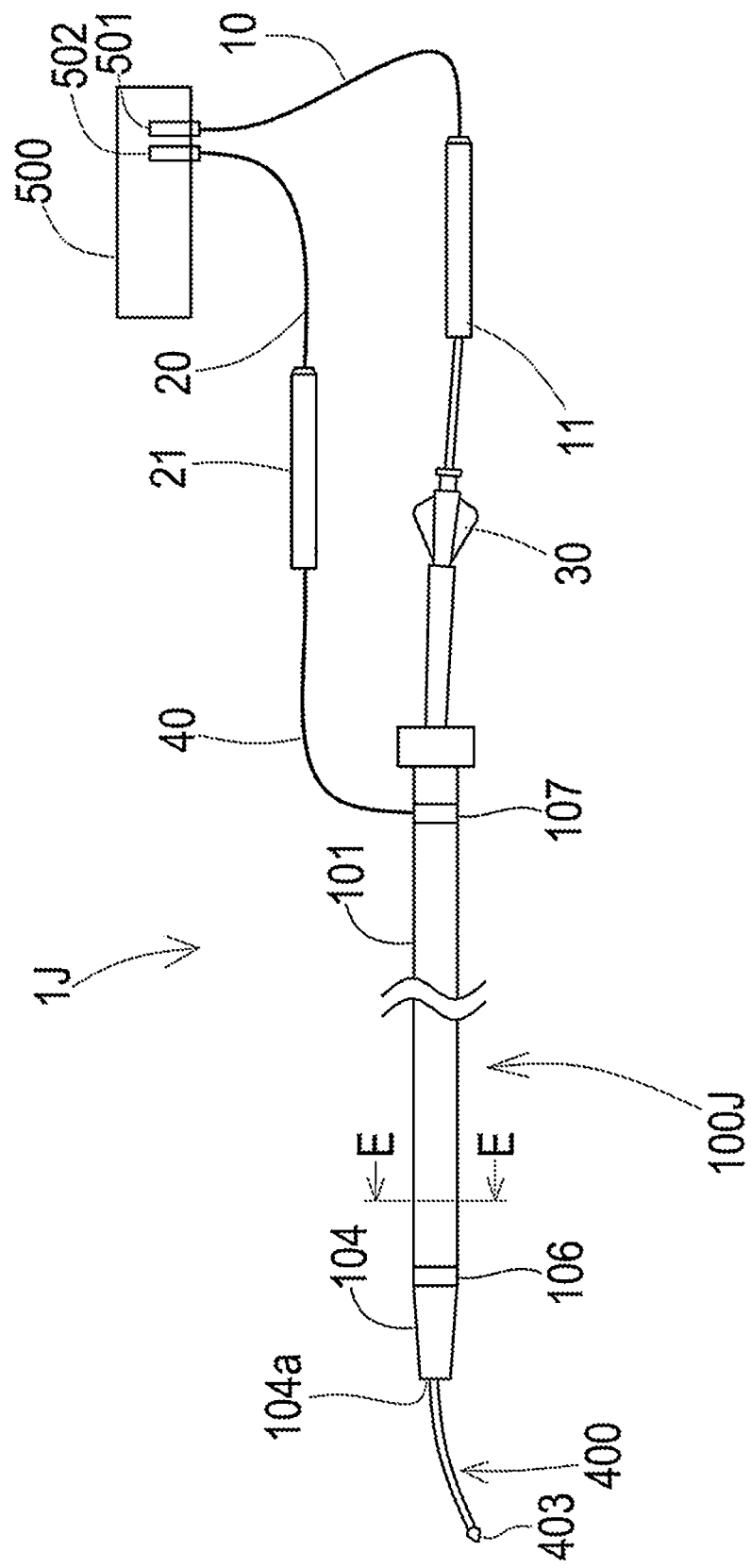
FIG. 21 is a schematic diagram illustrating the general configuration of a plasma guide wire CTO system according to a tenth embodiment.
Figure 22:
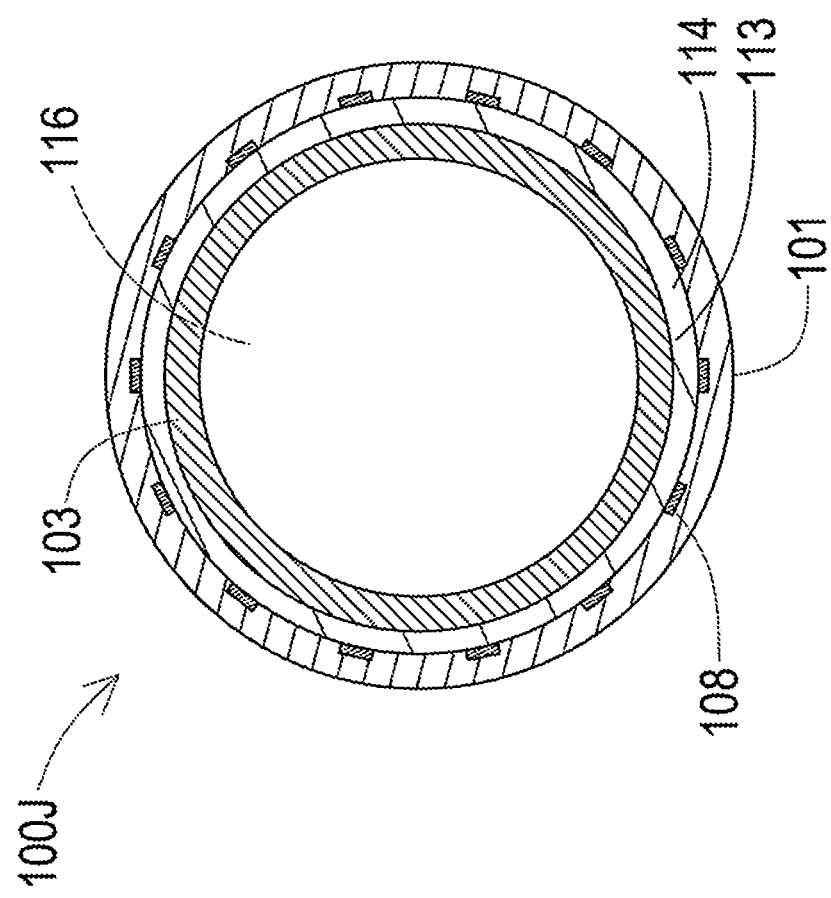
FIG. 22 is a schematic diagram illustrating a section of a plasma catheter taken along a line E-E in FIG. 21.

FIG. 21 is a schematic diagram illustrating the general configuration of a plasma guide wire CTO system 1J according to a tenth embodiment. FIG. 22 is a schematic diagram illustrating a section of a plasma catheter 100J taken along a line E-E in FIG. 21. The plasma guide wire CTO system 1J of the tenth embodiment is provided with the plasma catheter 100J in place of the plasma catheter 100 described in the first embodiment and with omission of the imaging sensor 200 and the imaging console 300. As shown in FIG. 21, the plasma catheter 100J is configured without the respective components corresponding to the expanding contracting portion and the actuating portion described in the first embodiment, i.e., without the first ring 109, the second ring 110, the first and the second stabilizer pieces 111a and 111b, the first and the second wire pieces 111c and 111d, the first and the second wires 112a and 112b and the first and the second wire shafts 117a and 117b. The plasma catheter 100J is also configured without the first inner shaft 102, the opening 102a and the adjuster 105 described in the first embodiment.

As shown in FIG. 22, in the plasma catheter 100J, only the second inner shaft 103 is inserted into the outer lumen 113 of the outer shaft 101, and an outer circumferential surface of the second inner shaft 103 is sealed by the sealing member 114. As shown in FIG. 21, a distal end of the second inner shaft 103 does not have the inclined shape described in the first embodiment. A distal-end tip 104 is joined with a distal end of the outer shaft 101 and the distal end of the second inner shaft 103. An opening 104a of the distal-end tip 104 is arranged to communicate with the second inner lumen 116 of the second inner shaft 103. Accordingly, the plasma catheter 100J is configured with the opening 102a and the opening 103a to use only the second inner lumen 116 for insertion of a medical device.

The plasma guide wire CTO system 1J of the tenth embodiment achieves canalization of CTO as follows. The proximal end of the delivery guide wire 70 is inserted from the opening 104a to pass through the second inner lumen 116 and protrudes out from a proximal end portion of the second inner lumen 116. The plasma catheter 100J is then transported along the delivery guide wire 70 to the false lumen 82. The operator subsequently places a distal end portion of the plasma catheter 100J at an optimum position for penetration into the true lumen, for example, by X-ray photography with injection of a contrast agent through the second inner lumen 116. After placing the plasma catheter 100J at the optimum position, the operator removes the delivery guide wire 70 and newly inserts the plasma guide wire 400 into the second inner lumen 116. The operator transports the distal end portion of the plasma guide wire 400 to the distal end portion of the plasma catheter 100J and causes the distal end portion of the plasma guide wire 400 to protrude out from the opening 104a. The operator then operates the RF generator 500 to cause streamer discharge at the distal-end tip 403 of the plasma guide wire 400 and performs ablation of the CTO 81.

For example, after removal of the delivery guide wire 70, the imaging sensor 200 described in the first embodiment may be inserted into the second inner lumen 116 to adjust the position of the plasma catheter 100J based on an image by the imaging sensor 200, in place of X-ray photography. In another example, when an opening communicating with the second inner lumen 116 is provided in a side face of the outer shaft 101, the proximal end portion of the delivery guide wire 70 may protrude out from this opening. This enables the plasma catheter 100J to be used as a rapid exchangeable-type catheter. In this case, two devices may be inserted simultaneously into the second inner lumen 116. For example, the delivery guide wire 70 may be inserted into a distal end side of the opening in the second inner lumen 116, and the imaging sensor 200 may be inserted into a proximal end side of the opening.

The plasma catheter 100J may have various modified configurations. For example, the plasma catheter 100J may be configured without the second inner shaft 103 in addition to the first inner shaft 102. In this modification, the outer lumen 113 of the outer shaft 101 may not be sealed but may be used as the second inner lumen 116. The plasma catheter 100J of the tenth embodiment (catheter) is provided with one second inner lumen 116 (lumen, shown in FIG. 22) for insertion of a medical device. This configuration reduces the diameter of the plasma catheter 100J. The first electrode 106 (electrode) is provided on the outer circumferential surface of the outer shaft 101 (shaft). This configuration allows for ablation of biological tissue using the plasma flow by insertion of the plasma guide wire 400 into the second inner lumen 116 (lumen).

K. Eleventh Embodiment

Figure 23:
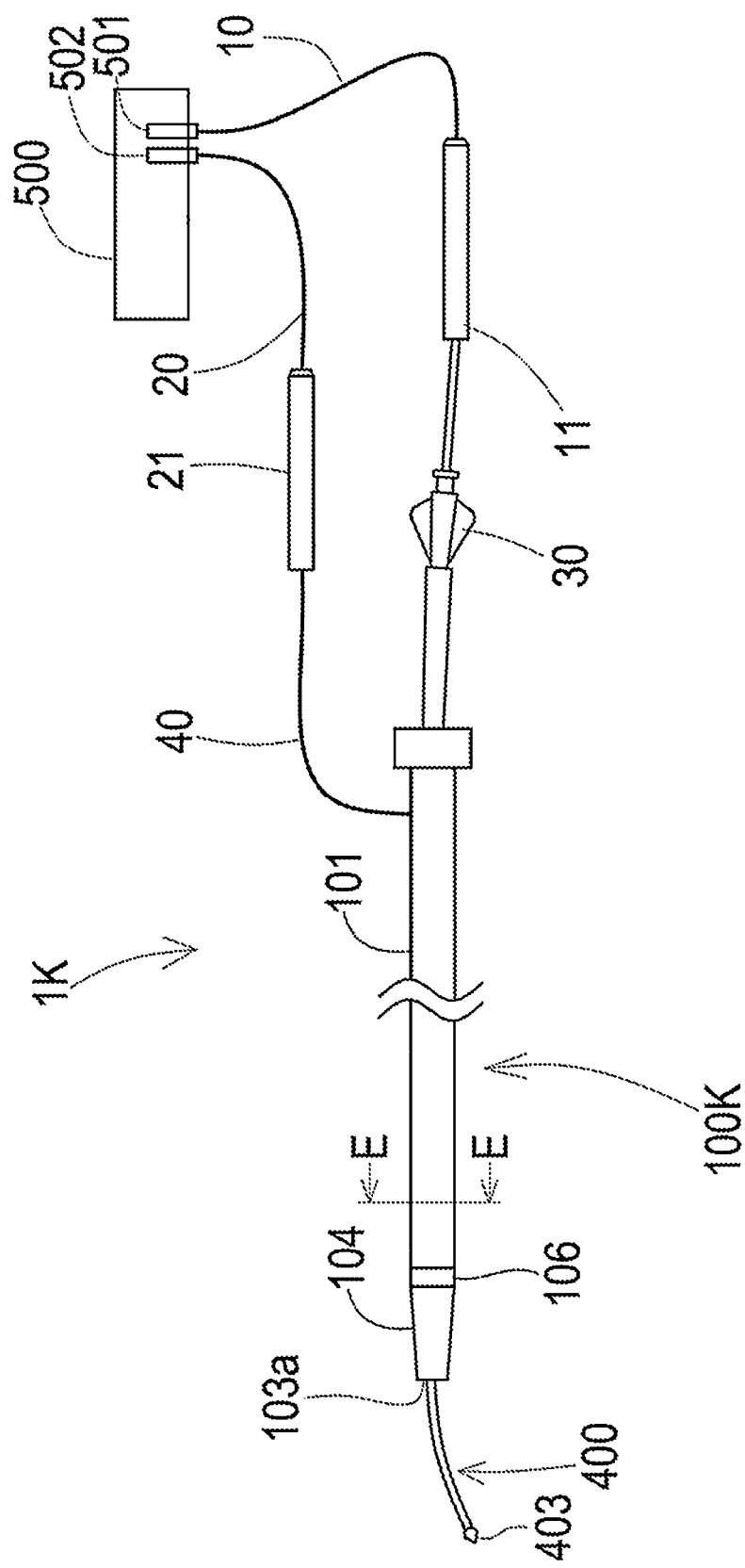
FIG. 23 is a schematic diagram illustrating the general configuration of a plasma guide wire CTO system according to an eleventh embodiment.

FIG. 23 is a schematic diagram illustrating the general configuration of a plasma guide wire CTO system 1K according to an eleventh embodiment. The plasma guide wire CTO system 1K of the eleventh embodiment is provided with a plasma catheter 100K in place of the plasma catheter 100J described in the tenth embodiment. The plasma catheter 100K is configured without the second electrode 107 described in the tenth embodiment. In the plasma catheter 100K, a cable 40 connected with the RF generator 500 is embedded in the outer shaft 101 and is electrically connected with part of a proximal end side of the braids 108 in the outer shaft 101. The plasma guide wire CTO system 1K achieves canalization of CTO by the same procedure as that of the tenth embodiment. The plasma catheter 100K may have various modified configuration. For example, the plasma catheter 100K may be configured without the second electrode 107. The configuration of the eleventh embodiment has similar advantageous effects to those of the tenth embodiment.

L. Modifications of Embodiments

The present disclosure is not limited to the embodiments described above but may be implemented by various aspects without departing from the scope of the disclosure. Examples of modifications are given below.

Modification 1

The first to the eleventh embodiments described above illustrate the exemplified configurations of the plasma guide wire CTO systems 1, 1A, 1B, 1H, 1J and 1K. The configurations of the plasma guide wire CTO systems 1, 1A, 1B, 1H, 1J and 1K may, however, be modified in various ways. For example, a sensor configured to obtain an image of biological tissue by a technique other than transmission and reception of ultrasonic waves may be employed as the imaging sensor 200. In another example, the plasma guide wire CTO system may be configured as a system that does not use the plasma guide wire 400 but uses a penetration guide wire for canalization of CTO.

Modification 2

The first to the eleventh embodiments described above show examples of use of the plasma guide wire CTO systems 1, 1A, 1B, 1H, 1J and 1K. The plasma guide wire CTO systems 1, 1A, 1B, 1H, 1J and 1K may, however, be used by a method other than those described above. For example, the plasma guide wire CTO system may be used for a blood vessel other than the coronary artery (for example, brain blood vessel) and may be used in a biological lumen other than the blood vessel. For example, the plasma guide wire CTO system may be used for another treatment other than canalization of CTO or for inspection.

Modification 3

The first to the eleventh embodiments described above illustrate the exemplified configurations of the plasma catheters 100 and 100A to 100K. The configurations of the plasma catheters 100 and 100A to 100K may, however, be modified in various ways. For example, the first inner lumen 115 (first lumen) and the second inner lumen 116 (second lumen) of the plasma catheter may have approximately the same diameters. In another example, the first inner lumen may be configured to have a smaller diameter than the diameter of the second inner lumen. For example, the plasma catheter may be provided with another lumen for a medical device such as a penetration guide wire, in addition to the first lumen and the second lumen.

For example, the opening 104a (first opening) communicating with the first inner lumen 115 may be provided at a position other than the distal end face of the distal-end-tip 104 (for example, in a side face of the distal-end tip 104). Similarly, the opening 102a (second opening) communicating with the first inner lumen 115 may be provided at a position other than the side face of the first inner shaft 102 on the side opposed to the second inner lumen 116. Similarly, the opening 103a (third opening) communicating with the second inner lumen 116 may be provided at a position other than the distal end face of the first inner shaft 102 (for example, in a side face of the second inner shaft 103). For example, part of the opening 104a, the opening 102a, the opening 103a and the opening 101a may be omitted, and another non-illustrated opening may be formed.

For example, it is preferable that the portion of the first inner shaft 102 that is extended toward the distal end side of the distal end portion of the second inner lumen 116 (second lumen), i.e., the extended shaft portion, is made of polyamide, in terms of satisfying both the ultrasonic transmission of the imaging sensor 200 and the sufficient wall thickness. It is preferable, on the other hand, that the portion of the first inner shaft 102 that is extended toward the proximal end side of the distal end portion of the second inner lumen 116, the outer shaft 101, the second inner shaft 103, the sealing member 114 and the like are made of polytetrafluoroethylene (PTFE), polyimide, tetrafluoroethylene-perfluoroalkoxy ethylene copolymer (PFA), or the like, in terms of providing the sufficient rigidity. It is preferable that the distal-end tip 104 is made of polyurethane, in terms of providing the sufficient flexibility.

It is preferable that the portion of the first inner shaft 102 that is extended toward the proximal end side of the distal end portion of the second inner lumen 116 has a wall thickness of not less than 20 microns, in terms of insulation from the braids 108 having electrical conductivity. The distal end of the second inner shaft 103 may not be inclined toward the first inner shaft 102 but may have a flat distal end face. For example, the plasma catheter may be provided with coil bodies made of a metal material having electrical conductivity as the reinforcing member, in place of the braids 108. The plasma catheter may be provided with both the braids 108 and the coil bodies. For example, the stabilizer 111 may be coated with a resin having insulating properties or may have a surface coated with a medical agent.

The configurations of the plasma catheters 100 and 100A to 100K of the first to the eleventh embodiments and the configurations of the plasma catheters 100 and 100A to 100K of Modifications 1 to 3 described above may be combined appropriately. For example, the expanding contracting portion of the configuration described in any of the second embodiment and the fourth to the seventh embodiments may be combined with the plasma catheter of the second embodiment having the fourth opening, the plasma catheter of the eighth embodiment having the shaft, or the plasma catheter of the ninth embodiment without the second inner shaft 103. In another example, the expanding contracting portion of the configuration described in any of the modifications of the first embodiment may be combined with the plasma catheter of the second embodiment having the fourth opening, the plasma catheter of the eighth embodiment having the shaft, or the plasma catheter of the ninth embodiment without the second inner shaft 103. For example, the configuration without the second electrode 107 described in the eleventh embodiment may be employed in the plasma catheter described in any of the first to the ninth embodiments.

Various aspects of the present disclosure are described above with reference to some embodiments and modifications. These embodiments and modifications are, however, provided for the purpose of facilitating understanding the aspects of the present disclosure and do not limit the present disclosure in any sense. These embodiments and modifications may be changed, altered and further modified without departing from the scope of the present disclosure, and equivalents thereof are also included in the present disclosure. Any of the technical features may be omitted appropriately unless the technical feature is described as essential in the description hereof.

The invention claimed is:

1. A catheter comprising:
an outer shaft;
a first inner shaft having a first lumen;
a second inner shaft having a second lumen arranged adjacent to the first lumen in a radial direction of the outer shaft,
a plasma guide wire configured to be inserted into the second lumen and slidably disposed therein, and including a distal-end tip made of a metal material having electrical conductivity; wherein
an extended shaft portion of the first inner shaft that is provided on a distal end side of a distal end face of the outer shaft extends in a longitudinal direction of the first inner shaft, the extended shaft portion including (i) the first lumen and (ii) a distal end portion located on a distal end side of a distal end portion of the second lumen; and
an electrode disposed on an outer circumferential surface of the outer shaft, wherein
the electrode generates plasma between the electrode and the distal-end tip of the plasma guide wire, and
the surface area of the electrode is larger than the surface area of the distal-end tip of the plasma guide wire.

2. The catheter according to claim 1, wherein
the extended shaft portion further comprises:
a first opening formed in the distal end portion of the extended shaft portion, the first opening communicating with the first lumen; and
a second opening formed on a proximal end side of the first opening in the extended shaft portion and in a side face of the extended shaft portion on a side opposed to the second lumen, the second opening communicating with the first lumen, and
the second inner shaft comprises a third opening formed in the distal end portion of the second inner shaft, the third opening communicating with the second lumen.

3. The catheter according to claim 2, wherein
the outer shaft further comprises a fourth opening formed in a side face of the outer shaft on a proximal end side of the third opening, the fourth opening communicating with the second lumen.

4. The catheter according to claim 2, further comprising
an expanding/contracting portion disposed in the extended shaft portion, the expanding/contracting portion being configured to expand and contract in a radial direction of the extended shaft portion; and
an actuating portion configured to expand and contract the expanding/contracting portion.

5. The catheter according to claim 4, wherein
the expanding/contracting portion is made of a material having an acoustic impedance that is larger than an acoustic impedance of biological tissue.

6. The catheter according to claim 4, wherein
the expanding/contracting portion is made of a radiopaque material.

7. The catheter according to claim 2, wherein
the first lumen has a diameter that is larger than a diameter of the second lumen.

8. The catheter according to claim 2, further comprising
a reinforcing member disposed in a thick wall portion of the outer shaft, wherein
the reinforcing member is made of a material having electrical conductivity and is connected with the electrode so as to have electrical continuity with the electrode.

9. The catheter according to claim 1, further comprising
an expanding/contracting portion disposed in the extended shaft portion, the expanding/contracting portion being configured to expand and contract in a radial direction of the extended shaft portion; and
an actuating portion configured to expand and contract the expanding/contracting portion.

10. The catheter according to claim 9, wherein
the expanding/contracting portion is made of a material having an acoustic impedance that is larger than an acoustic impedance of biological tissue.

11. The catheter according to claim 9, wherein
the expanding/contracting portion is made of a radiopaque material.

12. The catheter according to claim 1, wherein
the first lumen has a diameter that is larger than a diameter of the second lumen.

13. The catheter according to claim 1, further comprising
a reinforcing member disposed in a thick wall portion of the outer shaft, wherein
the reinforcing member is made of a material having electrical conductivity and is connected with the electrode so as to have electrical continuity with the electrode.

14. The catheter according to claim 13, wherein
the reinforcing member is made of a radiopaque material.

15. A recanalization catheter system comprising:
the catheter according to claim 1; and
a sensor configured to obtain information for generation of an image of biological tissue, wherein
the plasma guide wire is configured to perform ablation of the biological tissue by using the plasma.

16. The recanalization catheter system according to claim 15, wherein
the sensor is configured to obtain the information in the first lumen, and
the plasma guide wire is disposed in the second lumen such that a distal end portion of the plasma guide wire protrudes from a distal end of the second lumen, the plasma guide wire being configured to perform the ablation of the biological tissue by using the generated plasma.

17. The catheter according to claim 1, wherein the electrode is provided at a distal end of the outer shaft.

18. A catheter comprising:
a shaft having a first lumen and a second lumen arranged adjacent to the first lumen in a radial direction of the shaft;
an extended shaft portion that is provided on a distal end portion of the shaft and extends in a longitudinal direction of the shaft, the extended shaft portion having the first lumen and a distal end portion located on a distal end side of a distal end portion of the second lumen in the shaft;
a plasma guide wire configured to be inserted into the second lumen and slidably disposed therein, and including a distal-end tip made of a metal material having electrical conductivity; and
an electrode disposed on an outer circumferential surface of the shaft, wherein
the electrode is located on a proximal end side of the extended shaft portion and generates plasma between the electrode and a distal end portion of the plasma guide wire, and
the surface area of the electrode is larger than the surface area of the distal-end tip of the plasma guide wire.

19. A catheter comprising:
a shaft having a first lumen and a second lumen arranged adjacent to the first lumen in a radial direction of the shaft, the shaft having an opening that is provided at a distal end of the shaft and communicates with the second lumen;
an extended shaft portion that is provided on a distal end portion of the shaft and extends in a longitudinal direction of the shaft, the extended shaft portion having the first lumen and a distal end portion located on a distal end side of a distal end portion of the second lumen in the shaft; and
an electrode located on a proximal end side of the extended shaft portion and disposed on an outer circumferential surface of the shaft, wherein
the second lumen is configured such that a plasma guide wire is inserted into the second lumen and protrudes from the opening of the shaft,
the first lumen of the extended shaft portion is configured such that a sensor is slidably movable in the first lumen of the extended shaft portion to obtain information for generation of an image of biological tissue of a target site, and
the plasma guide wire includes a distal-end tip made of a metal material having electrical conductivity to generate plasma between the electrode and the distal-end tip to cause ablation of the target site.

20. The catheter according to claim 19, wherein
the sensor is configured to obtain information for generation of an image of the plasma guide wire protruding from the opening of the shaft.

\* \* \* \* \*